US008206907B2

(12) United States Patent
Milstein et al.

(10) Patent No.: US 8,206,907 B2
(45) Date of Patent: Jun. 26, 2012

(54) SCD FINGERPRINTS

(75) Inventors: Cesar Milstein, Cambridge (GB); Celia Prilleltensky-Milstein, legal representative, Cambridge (GB); Charles Nicholas Hales, Cambridge (GB); Margaret Hales, legal representative, Cambridge (GB); Adrian Woolfson, Cambridge (GB)

(73) Assignees: Medical Research Council, London (GB); Cambridge Enterprise Limited, Cambridge (GB)

( * ) Notice: Subject to any disclaimer, the term of this patent is extended or adjusted under 35 U.S.C. 154(b) by 352 days.

(21) Appl. No.: 12/237,915

(22) Filed: Sep. 25, 2008

(65) Prior Publication Data

US 2009/0181863 A1 Jul. 16, 2009

Related U.S. Application Data

(63) Continuation of application No. 12/070,312, filed on Feb. 15, 2008, now abandoned, which is a continuation-in-part of application No. 10/506,906, filed as application No. PCT/GB03/00974 on Mar. 7, 2003, now abandoned.

(30) Foreign Application Priority Data

| Mar. 4, 2002 | (GB) | .................................. 0205394 |
| Apr. 3, 2002 | (GB) | .................................. 0207746 |
| Dec. 3, 2002 | (GB) | .................................. 0228195 |

(51) Int. Cl.
*C12Q 1/68* (2006.01)
*G01N 33/53* (2006.01)
*G01N 33/543* (2006.01)
*G01N 33/574* (2006.01)
*G01N 33/68* (2006.01)

(52) U.S. Cl. ...... 435/6.1; 435/6.11; 435/6.14; 435/7.23; 435/7.24; 436/501; 436/518; 436/86

(58) Field of Classification Search .................. None
See application file for complete search history.

(56) References Cited

U.S. PATENT DOCUMENTS

| 5,292,636 A * | 3/1994 | Kung et al. ....................... 435/5 |
| 6,916,628 B1 * | 7/2005 | Furusako et al. ............ 435/7.94 |
| 2009/0181863 A1 * | 7/2009 | Milstein et al. ................. 506/18 |

OTHER PUBLICATIONS

Nasu et al, Int. Jour. Oncol., vol. 13, pp. 525-530, 1998. Serum soluble CD44 levels for monitoring disease states in acute leukemia and myelodysplastic syndromes.*
Belov et al., "Immunophenotyping of Leukemias Using a Cluster of Differentiation Antibody Microarray." Cancer Research, vol. 61, pp. 4483-4489, Jun. 1, 2001.
Perez-Encinas et al., "Tumor burden and serum level of soluble CD25, CD8, CD23, CD54 and CD44 in non-Hodgkin's lymphoma." Haematologica, vol. 83, No. 3, pp. 752-754, 1998.
Beguin et al., "Soluble CD23 and Other Receptors (CD4, CD8, CD25, CD71) in Serum of Patients with Chronic Lymphocytic Leukemia." Leukemia, vol. 7, No. 12, pp. 2019-2025, 1993.
European Search Report in EP 10012418.9, dated Feb. 15, 2011.
Biglino et al., Clinical Immunology and Immunopathology, 78(1):61-69 (1996).
Knauf et al., Leukemia and Lymphoma, 27(5/6):523-532 (1997).
Malaise et al., Arthritis & Rheumatism, 36(9):S128 (1993).
Ribbens et al., Clin. Exp. Immunol., 120(1):194-199 (2000).
Swaak et al., Clin. Rheumatology, 14(3):293-300 (1995).
Woolfson et al., Proc. Natl. Acad. Sci. USA, 91(14):6683-6687 (1994).
Zajkowska et al., Infection, Urban Und Vogel Medien Und Medizin Verlagsgesellschaft MBH, 29(2):71-74 (2001).

* cited by examiner

*Primary Examiner* — David A Saunders
(74) *Attorney, Agent, or Firm* — McAndrews, Held & Malloy Ltd.

(57) ABSTRACT

This invention relates to methods of testing, diagnosing, monitoring, prognostically stratifying and classifying disease, disorders and other medical conditions and physiological states through the detection and analysis of soluble CD antigens in a body fluid sample.

29 Claims, 16 Drawing Sheets

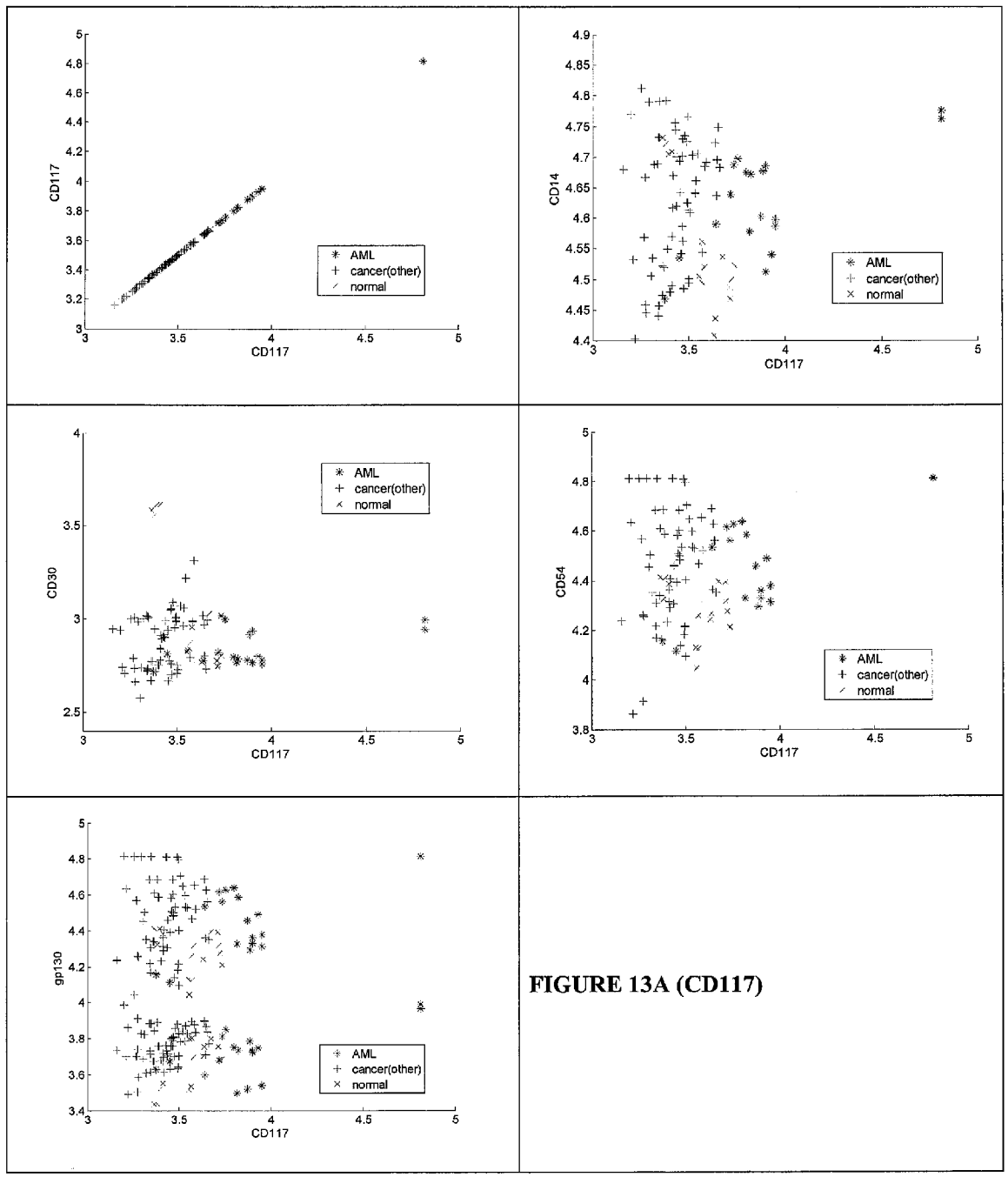
FIGURE 13A (CD117)

FIGURE 13B (CD14)
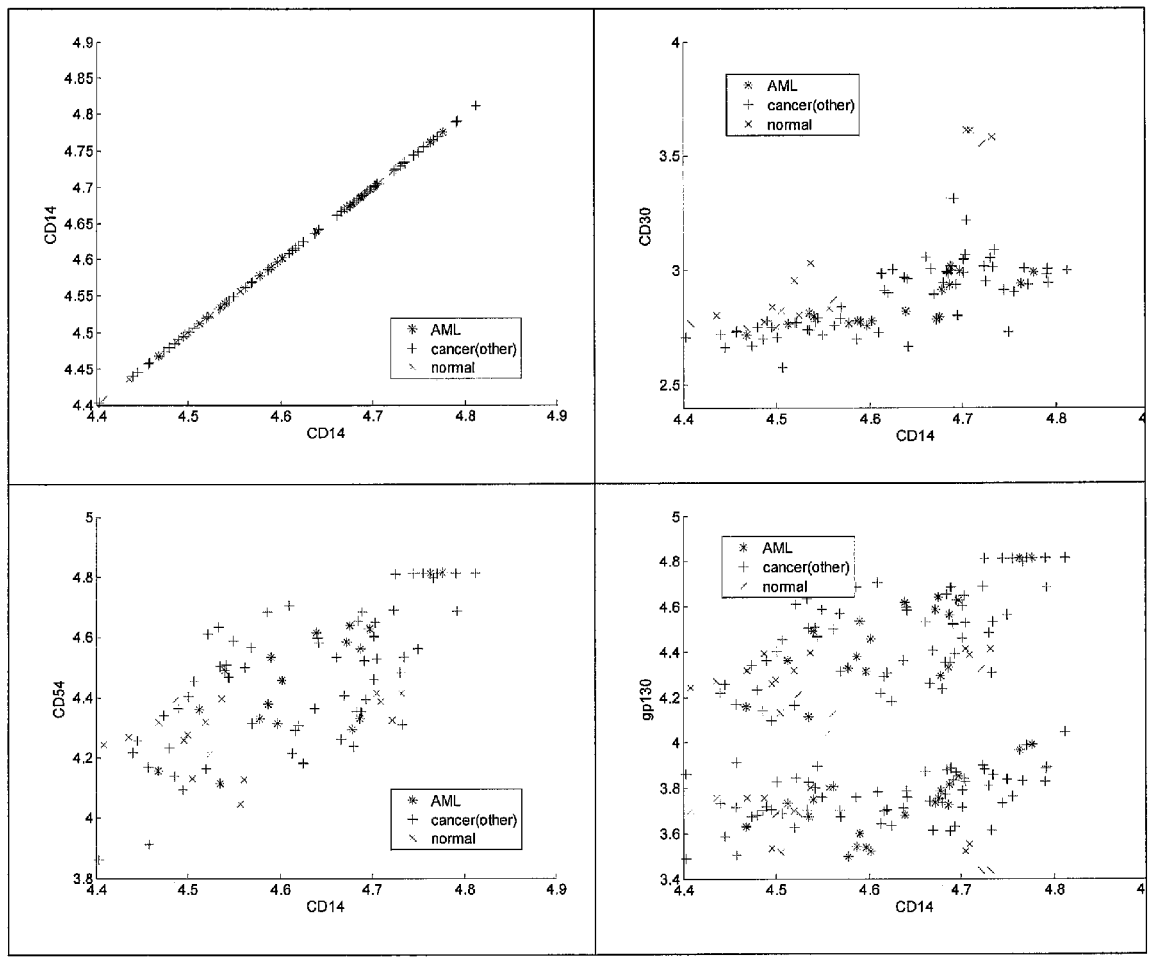

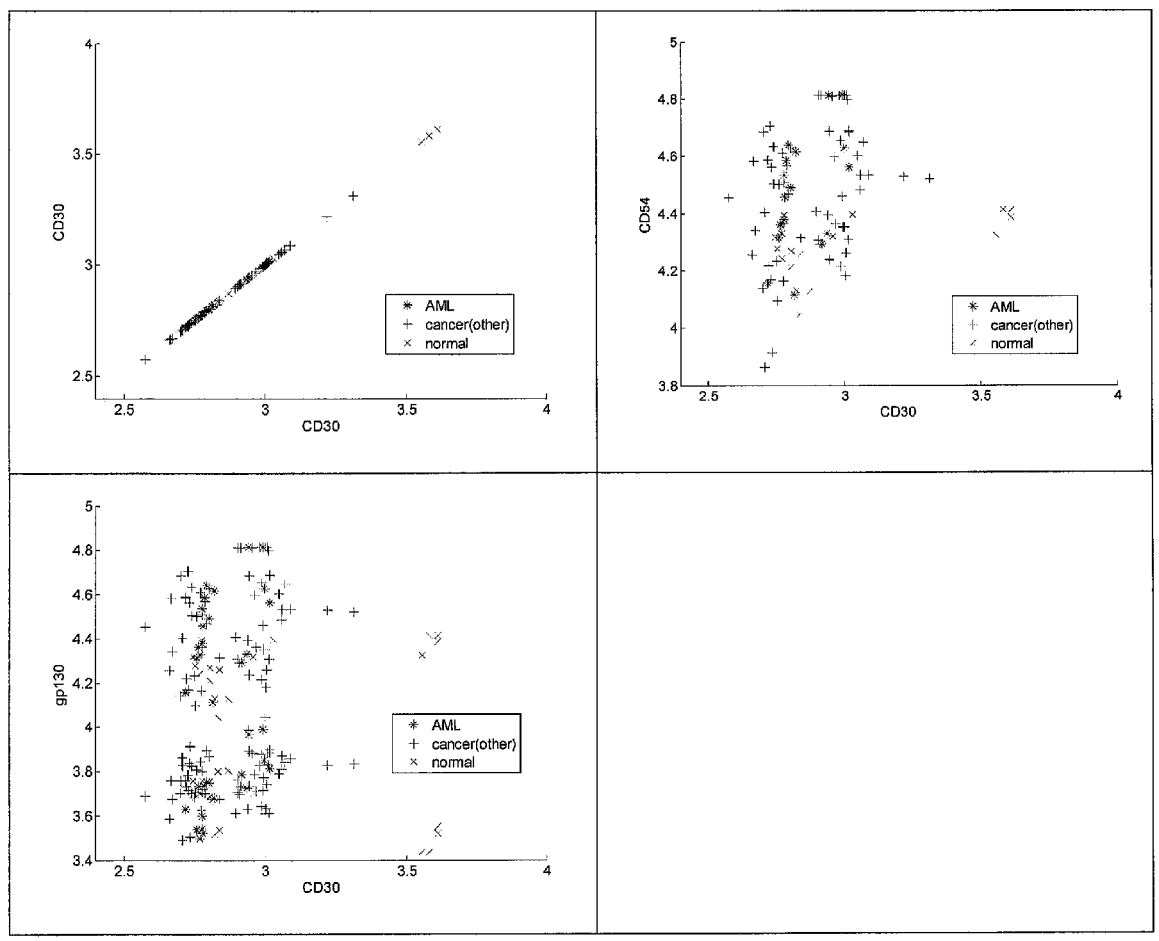
FIGURE 13C (CD30)

FIGURE 13D (CD54)
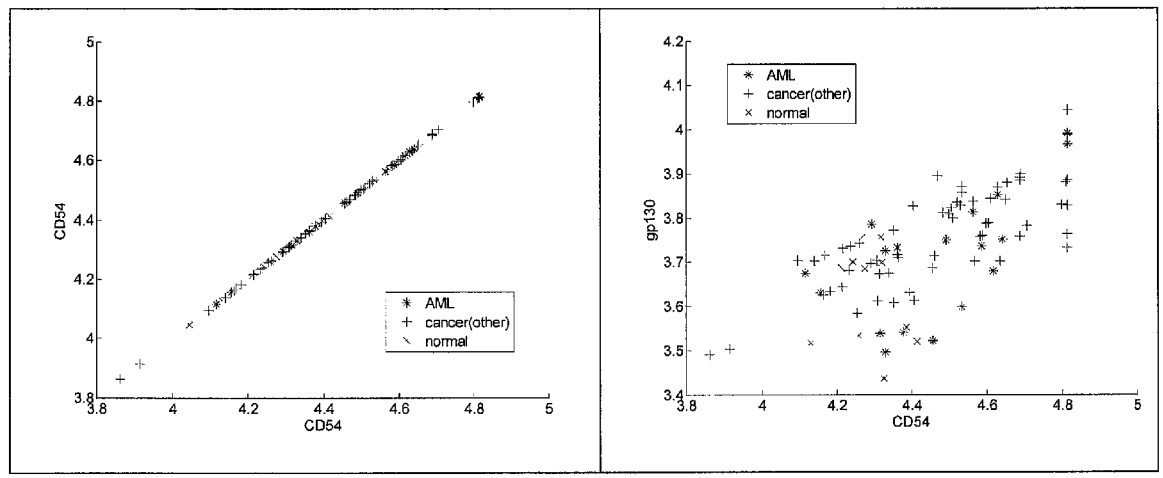
FIGURE 13E (Gp130)
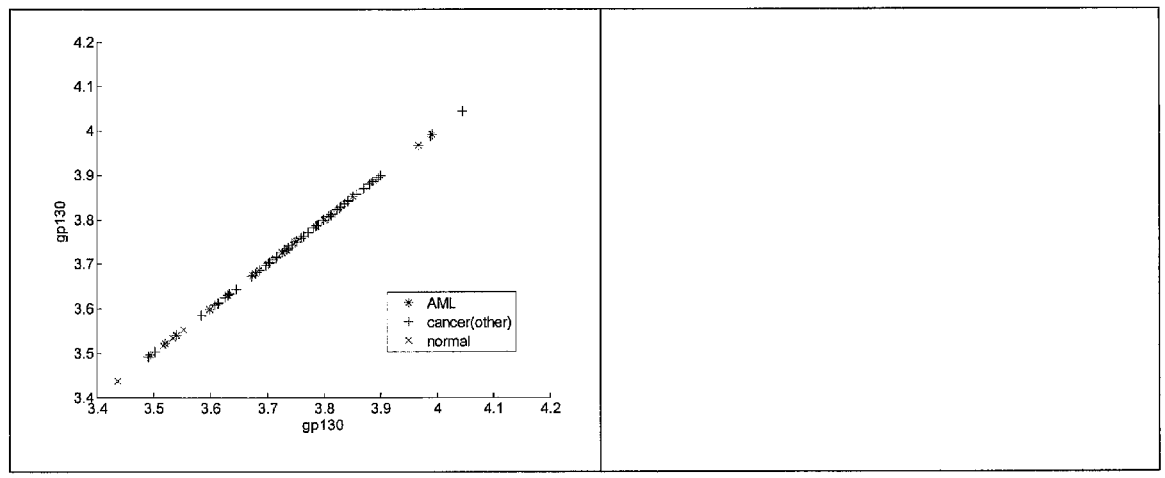

SCD FINGERPRINTS

This application is a continuation of U.S. patent application Ser. No. 12/070,312, which was filed Feb. 15, 2008, now abandoned which is a CIP of U.S. patent application Ser. No. 10/506,906, filed Jun. 27, 2006 (now abandoned), which is a 371 national phase application of PCT/GB03/00974 filed Mar. 7, 2003, which claims the benefit of GB0205394.0 filed Mar. 7, 2002; GB027746.9 filed Apr. 3, 2002; and G130228195.4, filed Dec. 3, 2002. Each of these applications in their entirety is incorporated by reference herein.

FIELD OF THE INVENTION

This invention relates to methods of testing, diagnosing, monitoring, prognostically stratifying and classifying disease, disorders and other medical conditions and physiological states through the detection and analysis of soluble CD antigens in a body fluid sample.

BACKGROUND OF THE INVENTION

Early, rapid and accurate diagnosis facilitates the timely and appropriate treatment of diseases, conditions and disorders, and enables selection of the most appropriate therapeutic interventions. The diagnosis and staging of diseases often involves many different diagnostic procedures, which in some cases have the disadvantages of being invasive, and/or prone to errors both due to limited sensitivity, and/or specificity, sampling variability, and technician variability. In the case of invasive testing may result in morbidity and occasionally even mortality. Genetic based diagnosis has been developed for a variety of diseases, to assess the presence, or the predisposition to, likelihood of remission and achievement of remission, response to therapeutic intervention or reoccurrence of such a disease. Such tests may also enable prognostic stratification, so as to determine those patients that need more aggressive therapeutic interventions and more intensive monitoring. Although there are several genetic assays available to identify the presence of gene mutations and chromosomal abnormalities, including polymerase chain reaction analysis, FISH and cytogenetic analysis, the identification of specific genetic changes is not always a direct indicator of a disease or a disorder and the likely aggressiveness of the underlying pathological process or indeed its likely responsiveness to therapy and it cannot thus be relied upon as an accurate prognostic indicator. However, changes in the overall patterns and/or expression levels of various genes and their corresponding proteins in a tissue or body fluid sample relative to a pre-disease-state, other stages of the disease or relative to negative and/or normal controls, can also be used to diagnose, stage and monitor disease and disorders. Such patterns of gene expression or protein expression may also be useful for prognostic stratification.

Therefore, there is a pressing need in the art to identify a differential gene expression pattern of a plurality of genes in a bodily sample that is reliably indicative of a particular disease, disorder and condition, or stage thereof, or predilection for. There is also a pressing need for such a display or fingerprint to be easily obtained from the patient, test or control individual. Such a fingerprint or 'picture' would be of use in diagnosing, predicting and/or detecting the presence or absence of a disease, disorder or condition, in assessing the response to a particular therapeutic intervention, in predicting the likelihood of a response to a particular therapeutic intervention or procedure, for predicting the extent and aggressiveness of any necessary therapeutic intervention, for the selection of a specific treatment from a selection of potential of therapeutic interventions, for prognostic stratification to determine the likely progression of the disease or disorder, or of disease-free survival with and without treatment for any individual with a particular disease or a condition, and in monitoring the progression of a disease process, and/or the impact of treatment on disease states or conditions.

Such gene expression patterns though are cumbersome to produce as they involve the preparation of RNA from a tissue sample and furthermore gene expression arrays are subject to technical problems including the fact that such arrays are not optimised for individual genes and that representation of the mRNA species population can be adversely influenced by the amplification procedures that are sometimes necessary if only a small amount of mRNA is present. There is consequently a need for a method that enables diagnostic patterns to be derived from body fluids. The measurement of soluble proteins released from cells by processes such as secretion of protein isoforms that are usually cell membrane associated and the derivation of patterns of such proteins therein, provides a simple method for diagnosing, predicting and/or detecting the presence or absence of a disease, disorder or condition, in assessing the response to a particular therapeutic intervention, in predicting the likelihood of a response to a particular therapeutic intervention or procedure, for predicting the extent and aggressiveness of any necessary therapeutic intervention, for the selection of a specific treatment from a selection of potential of therapeutic interventions, for prognostic stratification to determine the likely progression of the disease or disorder, or of disease-free survival with and without treatment for any individual with a particular disease or a condition, and in monitoring the progression of a disease process, and/or the impact of treatment on disease states or conditions.

In some instances where the power of an individual test is limited, gene expression signatures or patterns may be combined with protein expression signatures or patterns to derive nested genomic/proteomic patterns that may be used in diagnosing, predicting and/or detecting the presence or absence of a disease, disorder or condition, in assessing the response to a particular therapeutic intervention, in predicting the likelihood of a response to a particular therapeutic intervention or procedure, for predicting the extent and aggressiveness of any necessary therapeutic intervention, for the selection of a specific treatment from a selection of potential of therapeutic interventions, for prognostic stratification to determine the likely progression of the disease or disorder, or of disease-free survival with and without treatment for any individual with a particular disease or a condition, and in monitoring the progression of a disease process, and/or the impact of treatment on disease states or conditions.

CD Antigens:

Lymphocytes and other leukocytes express large numbers of different cell surface antigens that are associated with the cell surface membrane. This cell membrane anchoring is often achieved through the presence of a hydrophobic transmembrane domain that spans the cell membrane although other mechanisms for cell surface linkage also exist. The differential expression of such cell surface associated molecules can be used to identify distinct leukocyte cellular subsets that perform different functions. These cell surface molecules or 'antigens' are known to serve a broad range of critically important cellular functions (many of which are related to immune function) and include: receptors for growth factors, molecules that mediate cell-to-cell interactions, receptors for viral adhesion, (such as CD4, CD112 and CD5 155), immunoglobulins, cell adhesion molecules, mediators of complement stimulation, enzymes and ion channels. These cell surface antigens can be identified with monoclonal antibodies or other ligands, each of which recognises with a varying degree of specificity a different cell surface antigen (or sub-determinant on any individual cell surface antigen). An international workshop was established to derive a systematic nomenclature for the monoclonal antibodies that recognised antigens present on the cell surface of human leukocytes (The cluster of differentiation (CD) antigens defined by the First International Workshop on Human Leukocyte Differentiation Antigens. Hum Immunol. 1984 September; 11(1): 1-10). As a result of the statistical 'cluster analysis' method used to rationalize and map these monoclonal antibodies to specific antigens, these molecules came to be known as cluster of differentiation (CD) antigens, or CD molecules/antigens (Kishimoto et 20 al., 1996 Proceedings of the Sixth International Workshop and Conference held in Kobe, Japan. 10-14 Garland Publishing Inc. New York, USA).

The discovery of CD antigens and the monoclonal antibody technology used to define them was a direct result of the work of one of the inventors of the present application (Dr. César Milstein) who invented monoclonal antibody technology with his colleague Georges Kohler (Kohler and Milstein). In their classic paper (Continuous cultures of fused cells secreting antibody of defined specificity Nature 1975, Aug. 7, 256 (5517), 495-7) Kohler and Milstein described how monoclonal antibodies of a single defined specificity could be produced by the fusion of myeloma cells with plasma cells. Kohler and Milstein were awarded the Nobel Prize for Medicine and Physiology for this work. In collaboration with Andrew McMichael in Oxford, Milstein subsequently raised and identified monoclonal antibodies to the first non-human (CD4) and human (CD1) CD antigens (McMichael et al. A human thymocyte antigen defined by a hybrid myeloma monoclonal antibody, Eur. J. Immunol. 1979 March; 9(3): 205-10).

The criteria necessary to assign a CD status to any given cell surface leukocyte molecule has changed as a result of technological advances achieved since the 1970s. At that time, clustering depended exclusively on the statistical revelation of similarities in the staining pattern of two or more antibodies that had been analysed on multiple different tissues and cell lines. However, presently a CD molecule is additionally also typically classified on the basis of its molecular characteristics, and structure (Bernard and Boumsell). A current list of CD antigen markers as of the last international workshop has been compiled (Table 43). This list was downloaded from the URL: hcdm.org/CD1toCD350.htm on Nov. 6, 2007, and is updated at regular intervals. The number of CD antigens has been increasing exponentially, but this exponential increase is likely to tail off eventually as the highly expressed antigens are discovered and only the rarer, lower-expressing molecules remain to be discovered and assigned a CD number. Eventually the list of CD antigens should be complete and this will then encompass all human cell surface leukocyte differentiation antigens and their homologues in other mammalian and non-mammalian species.

It should be noted that although CD antigens were initially defined and characterised on the basis of the fact that they are expressed on the cell surface where they are associated with the cell membrane of human leukocytes, including lymphocytes (e.g., T cells, B cells), monocytes (e.g., macrophages) and granulocytes (e.g., neutrophils, eosinophils and basophils), CD antigens have also been found on the surface of other blood borne cells, such as stem cells, erythrocytes and megakaryocytes, Furthermore there are CD antigens that are expressed on the cell surface of cells and tissues which are not typically part of the immune system, and include cells from tissues such as the brain, liver, kidney, epithelial cells, etc. A subset of the cell surface CD antigens expressed in non-immune tissues are tissue specific CD antigens that are expressed predominantly in a specific tissue or tissues. Thus, CD molecules are ubiquitous and are expressed in differing amounts in every tissue in the body.

Historically, cell surface CD antigens have been used as diagnostic markers. Indeed, leukemias are diagnosed on the basis of cell morphology, the expression of particular cell surface CD antigens, enzyme activities and cytogenetic abnormalities such as chromosome translocations. The expression of at least three cell surface CD antigens on leukaemia cells can be determined using labelled antibodies to particular CD antigens using flow cytometric analysis.

Significantly, however, it has been observed that the CD antigens usually expressed at the cell surface may also be found as a soluble (sCD) form that is released into the blood (serum, plasma or whole blood) and into other body fluids including, for example, cerebrospinal fluid (CSF), urine, saliva, ascitic fluid, peritoneal fluid, uveal fluid, synovial fluid, pleural fluid. These CD molecules can be secreted from cells as a result of "active" processes such as alternative splicing (Woolfson and Milstein, PNAS, 91 (14) 6683-6687 (1994)) or by "passive" processes, such as cell surface shedding. Thus, CD molecules can be found in three different forms, (i) cell surface (membrane associated) CD molecules, (ii) secreted (shed or soluble) CD molecules, (sCD) produced by alternative splicing or other mechanisms and (iii) intracellular CD molecules (that remain within the cell cytoplasm). Each of these three classes of CD molecules can be complete molecules or fragments derived from them as a result of alternative splicing. These different isoforms may also have differential post-translational modifications, such as glycosylation.

Recent studies (see WO 00/39580) have described a system for the diagnosis of haematological malignancies, whereby immunoglobulins are immobilized on a solid support and used to detect cell-surface CD antigen levels, in particular cell-surface CD antigen levels in samples of whole cells. Using this approach, a pattern of expression of cell surface bound CD antigens is generated, which one of the inventors (Dr Adrian Woolfson) and others have shown to be indicative of the presence of various defined leukemias in a patient. However, this cell-surface based system of diagnosis is burdened with several disadvantages that are also applicable to the diagnosis of diseases and disorders that are not hematological. First, because the technique is cell-based, it has the associated disadvantages of having an undesirable amount of background noise and difficulty in measuring antigen levels accurately. Such methods furthermore only allow semi-quantitative determination of the relative densities of sub-populations of cells of distinct immunophenotypes, indeed absolute quantification using this method may not be possible, even in principle. Another problem with this cell-based method is that at equilibrium, the number of cells captured by the immobilised CD ligand dot, (antibody dot), depends not only on the affinities of the interactions, but also on the concentration of the CD ligand, (antibody), on the dot and the level of expression of the CD antigen on the cell surface. And in addition to this, there is the issue of the stereochemical availability and accessibility of the CD ligand, (monoclonal antibody), immobilized on the nitrocellulose membrane of the CD antibody array.

Furthermore, computerized quantification of the cell density as indicated by the pixel intensity corresponding to each dot of arrayed antibody depends not only on the number of cells in the test sample, but also on cell size and morphology. In addition to all these factors, the absolute requirement for purification of cells from whole blood, and the possible need to fractionate blood cells still further, makes such a cell-based approach both labor intensive and time consuming. Importantly though, a cell-based approach only provides a pattern of CD antigens expressed on the cell surface and does not take into account soluble CD antigens that are secreted from the cell or shed from the cell surface (sCD antigens). Therefore, there exists a need in the art for a simple method for diagnosis of a disease, disorder or condition, in which the limitations of the above described cell-surface based system are overcome, and for a complete, sensitive and specific profile of a disease which is obtained from an individual in a reliable and practical manner.

SUMMARY OF THE INVENTION

The present inventors have surprisingly found that particular disease states and disorders can be characterized by specific patterns of expression levels of a plurality of shed/soluble/secreted CD antigens (sCD) (as herein defined) derived from a body fluid sample taken from an individual. That is, the present inventors have found that a profile or 'sCD print' or 'fingerprint' or 'barcode' or 'pattern' of the levels of a plurality of sCD antigens correlates with a particular disease or disorder (such as cancers, autoimmune diseases, cardiovascular diseases and so on), or a combination of diseases and/or disorders, or physiological states (such as those induced by administration of a drug or toxin). By developing fingerprints comprising soluble CD (sCD) antigens from readily available bodily fluids, the present inventors have overcome the limitations of diagnostic techniques using cell surface CD molecules discussed above.

The present inventors have furthermore surprisingly found that the sCD profile or 'sCD finger print' can comprise one or both of the following two components: (1) a 'stromal' component and (2) a cellular component. The stromal component represents the expression level of one or more of a plurality of sCD molecules expressed in a bodily fluid that reflects the immune system's homeostasis or 'steady state', which is specific to a particular disease, disorder or condition. In essence, the composite expression level of a plurality of immunologically related sCD molecules produces a fingerprint specific to the particular physiological state induced by the disease, disorder or condition of interest. The second component of a sCD profile or sCD fingerprint, the cellular component, represents the expression level of one or more of a plurality of sCD molecules expressed in a bodily fluid, and reflects the secretion or shedding of tissue-specific soluble CD antigens, e.g., including from the diseased tissue. Thus, the inventors have designated three types of sCD fingerprints useful in assessing a disease, disorder or condition: 1) a stromal sCD fingerprint, 2) a cellular sCD fingerprint, and 3) a composite of a stromal and a cellular sCD fingerprint.

The inventors have found that each of these three types of sCD fingerprints can be encompassed in a yet broader fingerprint that further includes a profile of expression levels of one or more of soluble MHC Class I proteins, cytokines and/or chemokines specific to a particular disease, disorder or condition.

Further still, the inventors have described herein that each of these three types of sCD fingerprints, either alone, or encompassed within the broader fingerprint described just above, can further be encompassed in an extended fingerprint that further includes a gene expression signature and/or a micro-RNA signature. Thus the following fingerprints may in summary be envisaged: (i) a sCD 'stromal' fingerprint, (ii) a sCD 'cellular' or 'tissue-specific' fingerprint, (iii) a composite 'stromal' sCD/sMHC Class I/cytokine/chemokine fingerprint, (iv) a composite 'cellular' sCD/sMHC Class I/cytokine/chemokine fingerprint, and (v) any of the above combined with a gene expression fingerprint or pattern.

The characterization of a disease or a condition according to a "sCD fingerprint" or to a fingerprint that includes a sCD fingerprint" can be used in many applications, including, but preferably not limited to: diagnosis, early diagnosis, prognostic stratification, the predisposition of an individual to a disease or disorder, the exclusion of a specific disease or disorder, staging of the severity of a disease or disorder, the detection of early relapse, defining complete remission, the detection of minimal residual disease, monitoring the progression of a disease or disorder, and monitoring the response to therapeutic intervention, whether medical or surgical.

In one embodiment, the disease includes, but is not limited to: an infectious disease, an inflammatory disease, an autoimmune disease and an oncological disease. In another embodiment, the infectious disease includes, but is not limited to: hepatitis, tuberculosis (TB), HIV, meningococcal infection, pneumonia and necrotizing enterocolitis. In another embodiment, the inflammatory disease includes, but is not limited to: inflammatory bowel diseases such as ulcerative colitis and Crohn's disease, appendicitis, endometriosis and chronic lung disease. In another embodiment the autoimmune disease includes, but is not limited to: Multiple sclerosis, uveitis, lupus, vasculitis and Behcet's disease. In another embodiment, the oncological disease includes, but is not limited to: haematological malignancies such as Myeloma (Bence Jones Proteinuria), Lymphoma, Chronic Myeloid Leukaemia (CML), Acute Myeloid Leukemia (AML), Chronic Lymphocytic Leukemia (CLL), Acute Lymphocytic Leukemia (ALL), Myelodysplastic syndromes, bone marrow failure, myelodysplastic syndrome, juvenile myelomonocytic leukaemia, T-cell chronic lymphocytic leukaemia, prolymphocytic leukaemia, hairy cell leukaemia, follicular lymphoma, lymphoplasmocytic immunocytoma, plasma cell leukaemia, T prolymphocytic leukaemia, mycosis fungicides, large granular lymphocyte leukaemia, and adult T cell leukaemia. In another embodiment, the oncological disease includes, but is not limited to solid tumours such as: colorectal cancer, breast cancer, vulval cancer, and pancreatic cancer, brain tumours such as glioma, cervical carcinoma, melanoma, ovarian cancer and prostate cancer.

In another embodiment, the disease includes, but is not limited to, a metabolic disease, a degenerative disease, a psychological disease, a psychiatric disease, an iatrogenic disease, a drug or toxin related disorder, a cardiovascular disease or disorder, a dietary disorder, a disease or disorder resulting from trauma and an endocrine disease or disorder. In one embodiment, the metabolic disease includes, but is not limited to, diabetes, diabetic nephropathy, chronic renal failure (for example that resulting from diabetic kidney disease), renal transplantation of a diseased kidney, and liver damage that results from a metabolic disease such as Wilson's disease. In one embodiment, the cardiovascular disease includes, but is not limited to deep vein thrombosis (DVT), pulmonary embolism (PE) or cardiac pathology such as that resulting from atherosclerosis. In one embodiment, the psychiatric disease includes, but is not limited to, schizophrenia. In one embodiment, the dietary disease includes, but is not limited to, macrocytic anemia (due to vitamin B12 deficiency). In one embodiment, the drug related disease includes, but is not limited to, liver damage resulting from a paracetamol or another drug overdose.

Described herein is a composition comprising a collection of a plurality of isolated ligands, one or more of which specifically binds a sCD antigen. These isolated ligands can be used to identify a sCD fingerprint of a sample from an individual with disease or without disease, or from a test or control individual. In one embodiment, the plurality of sCD antigens that are shed or secreted from the cell surface or intracellular compartment as a result of processes that include, but are not limited to, alternative splicing, are derived from the entirety or any subgroup of the CD antigens listed in Table 43. Although this list comprises surface or membrane-associated CD antigens, it should be clear that the present invention encompasses the corresponding soluble isoform of the cell surface associated CD antigens, produced as a result of shedding, alternative splicing, and/or secretion. As such, each defined cell surface CD antigen in this list stands as an ambassador for its soluble counterpart. In another embodiment, a plurality of sCD antigens includes any grouping of soluble isoforms of the CD antigens listed in Table 44 and/or Table 45 or subgroup thereof.

In yet another embodiment of a composition comprising a collection of a plurality of isolated ligands that specifically binds a plurality of corresponding sCD antigens, the subgroup or plurality of sCD antigens includes one or more or all of the following soluble CD antigens: sCD14, sCD30, sCD54, sCD117 and sCD130. In one aspect of this embodiment, the plurality of sCD antigens includes a sCD antigen of the cellular type (CD117) and one or more sCD antigens of the 'stromal' type (CD14 (LPS receptor), sCD30 (present on T cells), sCD54 (ICAM-1), and sCD130 (a class 1 cytokine receptor). This composition can be used to generate a sCD fingerprint that is indicative of or classifies with a sample obtained from an individual with disease, and a fingerprint from an individual without disease, such as a sample taken from a healthy, individual. In one embodiment the disease is AML.

In yet another embodiment of a composition comprising a plurality of isolated ligands that specifically binds a plurality of corresponding sCD antigens, where the plurality of sCD antigens includes one or more or all of the following soluble CD antigens: sCD14, sCD30, sCD54, sCD117 and sCD130, the composition further comprises a plurality of isolated ligands that specifically binds to (a) one or more isolated ligands that selectively bind to a soluble isoform of a major histocompatibility (MHC) class I antigen, and/or (b) one or more isolated ligands that selectively bind to a chemokine and/or a cytokine, and/or (c) one or more isolated ligands that selectively bind to an over-expressed surface antigen associated with a specific pathology. Like the soluble CD antigens, soluble MHC class I molecules may be formed as a result of shedding from the cell surface or by an active process of secretion. These active processes of secretion include, but are not limited to, processes of alternative splicing that generate soluble isoforms of molecules that are also found anchored to the cell membrane. This composition can be used to generate a fingerprint reflecting the expression levels of one or more of the above mentioned sCD antigens and soluble MHC Class I antigens, that is indicative of/or classifies with a sample obtained from an individual with disease, and a fingerprint from an individual without disease, such as a sample form a healthy, individual. In one embodiment the disease is AML.

In yet another embodiment of a composition comprising a plurality of isolated ligands which specifically binds a plurality of sCD antigens, where the plurality of sCD antigens includes one or more or all of the following soluble CD antigens: sCD14, sCD30, sCD54, sCD117 and sCD130, and where the composition optionally further comprises one or more isolated ligands which specifically binds to (a) one or more isolated ligands that selectively bind to a soluble isoform of a major histocompatibility (MHC) class I antigen, and/or (b) one or more isolated ligands that selectively bind to a chemokine and/or a cytokine, and/or (c) one or more isolated ligands that selectively bind to an over-expressed surface antigen associated with a specific pathology, the composition further comprises ligands capable of identifying a gene signature and/or a micro-RNA signature. This composition can be used to generate a fingerprint reflecting the expression levels of one or more of the above mentioned sCD antigens and optionally one or more of soluble MHC Class I antigens, cytokines, chemokines, micro-RNAs and other genes, that is indicative of or classifies with a sample obtained from an individual with disease, and a fingerprint from an individual without disease, such as a sample form a healthy, individual. In one embodiment the disease is AML.

As used herein, the terms "gene signature" or "gene expression profile" or "gene expression fingerprint" are interchangeable and refer to the pattern of gene expression modulation in a plurality of genes, including an increase or decrease of gene expression in a sample from an individual with a disease or disorder of interest relative to that of a control, e.g. where the control individual does not have the disease or disorder of interest, and/or is a healthy individual. For example, for a plurality of 10 genes, possibly genes 1-6 are reduced in expression and genes 7-10 are increased in expression in the sample of the diseased individual relative to the control individual. The profile or fingerprint of a diseased state will include the relative degree of increase or decrease of expression of the genes of the set in a sample when compared to the same sample type from a negative control, e.g. a control individual without the disease such as a healthy control. For example, expression of gene 1 may be reduced by half, gene 2 by ⅔ gene 3 not expressed at all, gene 7 doubled in expression, gene 10 increased 3 fold in expression, and so on in response to each of the compounds of the set and relative to the steady state levels of said genes). In the typical case, the comparison is between a sample from an individual with disease versus one without the disease, or a comparison between samples obtained before and after therapy, or a comparison between different stages of a disease. The result is a gene expression profile, or gene expression fingerprint, or expression fingerprint. The fold increase or decrease in expression can range from up to 0.2 fold, 0.3 fold, 0.4 fold, 0.5 fold, 0.6 fold, 0.7 fold, 0.8 fold, 0.9 fold, up to 1 fold, 1.1 fold, 1.2 fold, 1.3 fold, 1.4 fold, 1.5 fold, 1.6 fold, 1.7 fold, 1.8 fold, 1.9 fold up to 2 fold, 2.1 fold, 2.2 fold, 2.3 fold, 2.4 fold, 2.5 fold, 2.6 fold, 2.7 fold, 2.8 fold, 2.9 fold, up to 3 fold, up to a 4 fold or more.

Micro-RNA expression profiles can be used to distinguish a sample from individual(s) with the disease of interest vs. those without the disease of interest. Micro-RNAs (miRs) are naturally-occurring 19 to 25 nucleotide transcripts found in over one hundred distinct organisms, including fruit flies, nematodes and humans. The miRs are typically processed from 60- to 70-nucleotide foldback RNA precursor structures, which are transcribed from the miR gene. The miR precursor processing reaction requires Dicer RNase III and Argonaute family members (Sasaki et al. (2003), Genomics 82, 323-330). The miR precursor or processed miR products are easily detected, and an alteration in the levels of these molecules within a cell can indicate a perturbation in the chromosomal region containing the miR gene, as described in US20060106360.

In one embodiment, a diagnostic method comprises the following steps: in a sample obtained from a subject suspected of having a disease such as AML, the status of one or more miR genes is evaluated by measuring the level of each miR gene product from the miR gene in the sample. An alteration in the level of miR gene product in the sample relative to the level of miR gene product in a control sample is indicative of the presence of the disease, (AML) in the subject. In a related embodiment, the invention provides a method of diagnosing a disease, particularly cancer, and including AML, in a subject, comprising reverse transcribing total RNA from a sample from the subject to provide a set of labeled target oligodeoxynucleotides; hybridizing the target oligodeoxynucleotides to a microarray comprising micro-RNA-specific probe oligonucleotides to provide a hybridization profile for the sample; and comparing the sample hybridization profile to the hybridization profile generated from a control sample, such as a healthy person or a person without disease, where an alteration in the micro-RNA in the subject relative to the control profile is indicative of the subject either having, or being at risk for developing, the disease of interest, e.g. AML. The microarray of micro-RNA-specific probe oligonucleotides preferably comprises micro-RNA-specific probe oligonucleotides for one or more, or a substantial portion of the human miRNome, or the full complement of micro-RNA genes in a cell. The microarray more preferably comprises at least about 60%, 70%, 80%, 90%, or 95% of the human miRNome.

A gene signature can be identified or confirmed using many techniques, including but preferably not limited or confirmed using the microarray technique. Thus, the gene signature of a plurality of disease-associated genes can be measured in a bodily sample using microarray technology. In this method, polynucleotide sequences of interest are plated, or arrayed, on a microchip substrate. The arrayed sequences are then hybridized with specific DNA probes from cells or tissues of interest. Just as in the RT-PCR method, the source of mRNA typically is total RNA isolated from the sample, and corresponding normal or 'healthy' sample(s).

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pair wise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to obtain gene signatures specific to a disease, disorder or condition of interest, often in many cases enabling diagnosis, staging, therapy and outcome prediction in a variety of diseases, disorders and conditions.

In one embodiment, one or more of the ligands used to capture the soluble CD antigens, the soluble MHC class I molecules, the chemokines and the cytokines is a protein. In another embodiment, one or more of the ligands contains one or more antibody CDR regions, and further comprises an immunoglobulin or non-immunoglobulin scaffold. In another embodiment, one or more of the ligands is an antibody. The antibody includes, but is not limited to, a monoclonal antibody, a polyclonal antibody, an Fv, scFv, Fab, (Fab)$_2$, an Fd, and a single domain antibody.

In one embodiment, the composition comprising a collection of plurality of isolated ligands that bind selectively to a plurality of sCD antigens and optionally comprising one or more ligands that selectively bind to one or more soluble MHC class I antigens, is bound to a solid support, which can be optionally formatted as an array. The plurality of isolated ligands in the array preferably is positioned in identifiable areas of the array and optionally in replicate. Solid supports include, but are not limited to, nitrocellulose, chips, beads, and silica based supports. The manner of linking a wide variety of compounds to various surfaces is well known and is amply illustrated in the literature. (See also, for example, Immobilized Enzymes, Ichiro Chibata, Halsted Press, New York, 1978, and Cuatrecasas, J. Biol. Chem. 1970 June; 245 (12):3059-65, the disclosures of which are incorporated herein by reference).

Reagents may be applied to the membrane materials in a variety of ways that are well known in the art. Various 'printing' techniques are suitable for application of liquid reagents to the membranes, such as micro-syringes, pens using metered pumps, direct printing, ink-jet printing, air-brush, and contact (or filament) methods and any of these techniques can be used in the present context. To facilitate manufacture, the membrane can be treated with the reagents and then subdivided into smaller portions (for example small narrow strips each embodying the required reagent-containing zones) to provide a plurality of identical carrier units.

Also described herein are kits comprising a collection of individual isolated ligands that bind selectively to individual sCD antigens and optionally comprising kits that contain ligands that selectively bind soluble MHC class I antigens, cytokines or chemokines. Although in isolation these kits are able to measure only individual sCD antigens, soluble MHC Class I molecules, cytokines or chemokines, if multiple kits are used then the levels of multiple soluble antigens, be they sCD antigens, soluble MHC class I antigens, cytokines or chemokines can be measured, so as to define a pattern in a manner analogous to a chip or bead based multiplexed method.

Also described herein are methods of diagnosing or prognosing or monitoring a disease or disorder, or predicting response to a therapeutic intervention, or detecting remission or detecting a relapse of the disease process or determining sensitivity to a given therapeutic intervention in advance of that intervention being commenced by analysing the levels of sCD antigens in a body fluid sample from a test individual, and comparing them to respective samples from one or more controls, where the controls can be positive and/or negative controls, and/or comparing them to databases containing reference fingerprints from positive and/or negative controls. Negative controls include healthy individuals, that is individuals with no documented pathology. Negative controls also includes individuals who do not have the disease or condition of interest, for example, AML. The sample can be, but is not limited to, a body fluid sample such as: whole blood, serum, plasma, saliva, urine, lymphatic fluid, cerebrospinal fluid, pleural fluid, follicular fluid, seminal fluid, amniotic fluid, milk, ascites, sputum, tears, perspiration, mucus, synovial fluid uveal fluid, and peritoneal fluid. the method covers tissue culture supernatants as well as body fluids. In another embodiment, the sample can be an in vitro tissue culture sample from one or more cell lines i.e. tissue culture supernatants. The cell lines can be an established cell line, or a cell line from the subject being tested. One embodiment described herein is a method of diagnosing or prognosing, or predicting response to a therapeutic intervention, or detecting minimal residual disease, or detecting remission or detecting a relapse of the disease process or determining sensitivity to a given therapeutic intervention in advance of that intervention being commenced for acute myeloid leukemia (AML) in a test individual who optionally may have been previously diagnosed as having leukaemia, where the method comprises: (a) determining the level of each of a plurality of soluble CD (sCD) antigens, including one or more of the following sCD antigens: sCD14, sCD30, sCD54, sCD117 and sCD130 in a serum or plasma sample from the test individual, and then (b) comparing the level of each said sCD antigen of step (a) with the level of each of the sCD antigens in a serum or plasma sample or whole blood sample taken from control individuals that are either healthy individuals with no documented pathology or who have one of the following leukemias: chronic myeloid leukemia (CML), non-Hodgkin's lymphoma (NHL), chronic lymphocytic leukemia (CLL), where detecting a statistically significant difference in the level of the sCD antigens in the comparison of step or defining a unique pattern of sCD antigen expression using a mathematical algorithm, such as the application of neural network analysis (b), is indicative of AML in the test individual.

Also described herein are methods of diagnosing or prognosing or monitoring or predicting response to a therapeutic intervention, or detecting remission or detecting a relapse of the disease process or determining sensitivity to a given therapeutic intervention in advance of that intervention being commenced, for leukemia in a test individual, where the method comprises determining the level (using a mathematical algorithm such as the application of neural network analysis, able to discern patterns) of each of the sCD antigens sCD14, sCD30, sCD54, sCD117 and sCD130, in a serum/plasma sample from the test individual, and comparing the level of each sCD antigen with the level of each of the sCD antigens in a serum/plasma sample from one or more representative healthy control individuals not having leukemia, where detecting a statistically significant difference in the level of each of the sCD antigens in the test individual, or deriving a disease state specific pattern using a mathematical algorithm such as neural network analysis, is indicative of leukemia in said test individual. In a preferred embodiment, the leukemia is acute myeloid leukemia, (AML), chronic myeloid leukemia (CML), non-Hodgkin's lymphoma (NHL) or chronic lymphocytic leukemia (CLL). In a further preferred embodiment, the leukemia is acute myeloid leukemia (AML).

Also described herein are methods of diagnosing or prognosing or predicting the response to a therapeutic intervention, or detecting remission or detecting a relapse of the disease process or determining sensitivity to a given therapeutic intervention in advance of that intervention being commenced, for acute myeloid leukemia (AML) in a test individual diagnosed as having leukemia, comprising: (a) determining the level of each of sCD14, sCD30, sCD54, sCD54, sCD117 and sCD130, in a serum or plasma sample or whole blood taken from a test individual, (b) comparing the level of each sCD antigen of step (a) with the level of each of said sCD antigens in a serum/plasma sample from healthy individuals or control individuals having a leukemia selected from the group consisting of, but not limited to: acute myeloid leukemia (AML), chronic myeloid leukemia (CML), non-Hodgkin's lymphoma (NHL) and chronic lymphocytic leukemia (CLL), (c) comparing the level of each of the sCD antigens of step (a) with the level of each of the sCD antigens in a serum sample or plasma sample or whole blood from control individuals having AML, (d) determining whether the level of each of the sCD antigens of step (a) corresponds with the level of each of the sCD antigens of the control individuals having either CML, NHL, or CLL, of step b) or healthy individuals, or with the level of each of said sCD antigens in serum/plasma from said control individuals having AML of step (b), wherein a determination in step (d) that said level of each of the sCD antigens of step (a) corresponds with the level of each of the sCD antigens in serum, or plasma or whole blood from said control individuals having AML of step (b) is indicative of AML in the test individual. A fingerprint or expression pattern comprising the levels of a plurality of sCDs where the sCD fingerprint represents one or more disease states can be generated using the above comparisons by means of the application of pattern recognition algorithms including, but not limited to genetic algorithms or neural network analysis.

Also described herein are methods of diagnosing or prognosing (by the prognostic stratification of patients into different prognostic groups), or predicting the response to a therapeutic intervention, or detecting minimal residual disease, or detecting remission or detecting a relapse of the disease process or determining sensitivity to a given therapeutic intervention in advance of that intervention being commenced, leukemia in an individual, comprising the steps of: (a) determining the level of a plurality of sCD antigens expressed in a serum, plasma or whole blood sample obtained from the individual, wherein the plurality of sCD antigens are soluble isoforms of the CD antigens listed in Table 43, Table 44, or Table 45, and (b) comparing the level of each of said plurality of sCD antigens in the serum/plasma sample according to step (a) with the level of each of said plurality of sCD antigens in serum/plasma from one or more individuals having leukemia, (c) comparing the level of each of said five or more sCD antigens in said blood according to step (a) with the level of each of said plurality of sCD antigens in blood from one or more individuals not having leukemia, (d) determining whether the level of said five or more sCD antigens of step (a) corresponds with the levels of said plurality of sCD antigens in step (b) as compared with levels of said plurality of sCD antigens in step (c), wherein said determination is indicative of said individual of step (a) having leukemia. The above method can be modified to distinguish between different subgroups of AML.

Also described herein are methods of developing a classifier (Duda 2001) useful for diagnosing or prognosing (by the prognostic stratification of patients into different prognostic groups), or predicting response to a therapeutic intervention, or detecting minimal residual disease, or detecting remission or detecting a relapse of the disease process or determining sensitivity to a given therapeutic intervention in advance of that intervention being commenced, for a leukemia selected from the group consisting of AML, CML, CLL and NHL, comprising: (a) measuring the level of sCD antigens selected from the group consisting of the soluble isoforms of the CD antigens listed in Tables 43, 44 and/or 45, in a training population wherein said training population is comprised of two subgroups, a first subgroup diagnosed as having a first leukemia selected from the group consisting of AML, CML, CLL and NHL, and a second subgroup diagnosed as having said leukemias other than said first leukemia, (b) apply one or more mathematical models to the levels of expression of step (a) to develop one or more classifiers which differentiate between said first subgroup and said second subgroup. In one embodiment, the leukemia of the first group is AML.

Also described herein are methods of diagnosing or prognosing (by the prognostic stratification of patients into different prognostic groups), or detecting minimal residual disease, or predicting response to a therapeutic intervention, or detecting remission or detecting a relapse of the disease process or determining sensitivity to a given therapeutic intervention in advance of that intervention being commenced of a leukemia in an individual, comprising determining the level of plurality of sCD antigens expressed in a serum/plasma sample obtained from said individual, where said plurality of sCD antigens are selected from the group consisting of the soluble isoforms of the CD antigens listed in Table 43, 44 and/or 45, and (b) using the results from step (a) in combination with a classifier designed to differentiate samples from an individual having AML from samples from individuals having CML or CLL or NHL (or controls or differentiation among AML subgroups) so as to determine a diagnosis with respect to AML (or specific subgroup).

In another embodiment of the methods described herein, the step of determining the level of each of said sCD antigens in the sample comprises contacting the sample with ligands specific for the sCD antigens. In one embodiment of the methods and products described herein, one or more of the ligands specific for the sCD antigens is an antibody, where each of the antibodies is specific for one of the sCD antigens. The antibodies include, but are not limited to a polyclonal antibody, monoclonal antibody, fv, scfv, dab, fd, fab, and fab'$_2$.

In another embodiment, methods of diagnosis based on analyses of sCD antigens as described herein are used in combination with one or more other diagnostic methods, including analysis of patient symptoms and/or presenting complaints.

In another embodiment, the one or more ligands that specifically bind an sCD antigen are attached to a surface, preferably a solid surface. The solid surface includes, but is not limited to a bead, a chip, a glass surface, nitrocellulose, or an ELISA plate.

Detailed embodiments of the above described compositions and methods are described below.

One embodiment disclosed herein is a composition having a plurality of isolated ligands and a carrier, the ligands encompassing one or more ligands that specifically binds to a soluble CD (sCD) antigen. The sCD antigen can be any sCD antigen, including, but preferably but not limited to, a soluble isoform of a CD antigen listed in Table 43, or one or more of the following sCD antigens: sCD14, sCD30, sCD54, sCD117 and sCD130. In another embodiment, the composition comprises a plurality of isolated ligands and a carrier, where each of the isolated ligands specifically binds to one of the following soluble CD (sCD) antigens: sCD14, sCD30, sCD54, sCD117 and sCD130. Another embodiment described is a composition consisting essentially of a plurality of isolated ligands and a carrier, where each of the isolated ligands specifically binds to a soluble CD (sCD) antigen listed as follows: sCD14, sCD30, sCD54, sCD117 and sCD130. Also described herein is a composition consisting of a plurality of isolated ligands and a carrier, where each of the isolated ligands specifically binds to a soluble CD (sCD) antigen selected from the group consisting of: sCD14, sCD30, sCD54, sCD117 and sCD130. In any of the above compositions, (a) the soluble CD (sCD) antigen can be sCD117, or (b) a first soluble CD (sCD) antigen can be sCD117 and a second soluble CD antigen can be any of: sCD14, sCD30, sCD54 and sCD130, or (c) a first soluble CD (sCD) antigen can be sCD117, and a second and third soluble CD antigen can be any of: sCD14, sCD30, sCD54 and sCD130, or (d) a first soluble CD (sCD) antigen is sCD117, and a second, third and fourth soluble CD antigen can be any of: sCD14, sCD30, sCD54 and sCD130, or (e) a first, second, third, fourth and fifth soluble antigens are sCD117, sCD14, sCD30, sCD54 and sCD130, respectively. In any of the above compositions, the number of sCD antigens can preferably range from two, up to three, up to four, up to five, up to six, up to seven, up to eight, up to nine, or up to 10 sCD antigens or more. The sCD antigens can include any combination or subgrouping of soluble isoforms of the CD antigens listed in Table 43, and/or Table 44 and/or Table 45. In another embodiment, the above compositions can further have a ligand which specifically binds to a soluble Major Histocompatibility Complex (sMHC) class I antigen. In another aspect, a composition can consist essentially of a plurality of isolated ligands and a carrier, where each of the isolated ligands specifically binds to a soluble CD (sCD) antigen selected from the group consisting of: sCD14, sCD30, sCD54, sCD117, sCD130 and a soluble Major Histocompatibility Complex (sMHC) class I antigen. In another embodiment, a composition consists of a plurality of isolated ligands and a carrier, where each of the isolated ligands specifically binds to a soluble CD (sCD) antigen selected from the group consisting of: sCD14, sCD30, sCD54, sCD17, sCD130 and a soluble Major Histocompatibility Complex (sMHC) class I antigen. In another embodiment, any of the above compositions can further comprise a ligand which selectively bind to a cytokine or to a chemokine. In another aspect, any of the above compositions, one or more of the ligands can comprise one or more antibody CDR regions, which can optionally further comprises a non-immunoglobulin scaffold which can optionally be synthetic. In one aspect, the non-immunoglobulin scaffold includes, but preferably is not limited to CTLA4, fibronectin, lipocallin, Rbp, Bbp ApoD, a natural bacterial receptor, staphylococcus A protein (SpA), GroEL, transferrin, tetranectin, human C-lectin, an AVIMER™ and/or an AFFIBODY™ scaffold. In any of the above compositions the ligand can be an antibody. The antibody includes, but preferably is not limited to a monoclonal antibody, an Fv, scFv, Fab, (Fab)2, an Fd, and a single domain antibody.

The ligands of any of the above compositions can be bound to a solid support, which includes a planar support. The support also includes, but is not limited to a bead, a chip, a glass surface, nitrocellulose, and an ELISA plate. In another aspect the plurality of ligands bound to a solid support is formatted as an array. Any of the above compositions, or combination of ligands thereof, can be formulated as a kit. Further, any of the above compositions or combination of ligands thereof can be used in any of the methods described herein, including but not limited to the following methods described below.

A method of detecting, diagnosing or prognosing acute myeloid leukemia (AML) in a test individual, the method comprising, for each of a plurality of sCD antigens, where at least one sCD antigen is selected from the group consisting of: sCD14, sCD30, sCD54, sCD117 and sCD130, (a) quantifying a level of expression of the sCD antigen in a serum/plasma sample of the test individual, and (b) comparing the level of sCD antigen quantified in step (a) to a quantified level of control sCD antigen in serum/plasma samples of control subjects classified as healthy subjects; where a determination from step (b) that is statistically different from the levels in the serum/plasma samples of the subjects classified as healthy subjects, results in a classification of the sCD antigen expression in the test subject with that of the subjects classified as having AML.

A method of detecting, diagnosing or prognosing acute myeloid leukemia (AML) in a test individual the method comprising, for each of a plurality of sCD antigens, where at least one sCD antigen is selected from the group consisting of: sCD14, sCD30, sCD54, sCD117 and sCD130, (a) quantifying a level of expression of the sCD antigen in a serum/plasma sample of the test individual, (b) comparing the level of sCD antigen quantified in step (a) to a quantified level of control sCD antigen in serum/plasma samples of control subjects classified as healthy subjects; and (c) comparing the level of sCD antigen quantified in step (a) to a quantified level of control sCD antigen in serum/plasma samples of control subjects classified as having AML; where a determination from steps (b) and (c) that the level of step (a) is statistically similar to the levels in the serum/plasma samples of the subjects classified as having AML, and is statistically different from the levels in the serum/plasma samples of the subjects classified as healthy subjects, results in a classification of the sCD antigen expression in the test subject with that of the subjects classified as having AML.

A method of detecting, diagnosing or prognosing acute myeloid leukemia (AML) in a test individual the method comprising, for each of a plurality of sCD antigens, where at least one sCD antigen is selected from the group consisting of: sCD14, sCD30, sCD54, sCD117 and sCD130, (a) quantifying a level of expression of the sCD antigen in a serum/plasma sample of the test individual, (b) comparing the level of sCD antigen quantified in step (a) to a quantified level of control sCD antigen in serum/plasma samples of control subjects classified as healthy subjects; and (c) comparing the level of sCD antigen quantified in step (a) to a quantified level of control sCD antigen in serum/plasma samples of control subjects classified as having AML; where a determination from steps (b) and (c) that the level of step (a) is statistically different from the levels in the serum/plasma samples of the subjects classified as having AML and is statistically similar to the levels in the serum/plasma samples of the subjects classified as healthy subjects, results in a classification of the sCD antigen expression in the test subject with that of the subjects who classified as healthy subjects, and where a determination from steps (b) and (c) that the level of step (a) is statistically similar to the levels in the serum/plasma samples of the subjects classified as having AML, and is statistically different from the levels in the serum/plasma samples of the subjects classified as healthy subjects, results in a classification of the sCD antigen expression in the test subject with that of the subjects classified as having AML.

A method of detecting, diagnosing or prognosing acute myeloid leukemia (AML) in a test individual the method comprising, for each of a plurality of sCD antigens, where the plurality of sCD antigens comprises one or more sCD antigens selected from the group consisting of: sCD14, sCD30, sCD54, sCD117 and sCD130, and where the plurality of sCD antigens comprises one or more sCD antigens selected from the group consisting of the soluble isoforms of the CD antigens listed in Table (43) (a) quantifying a level of expression of the sCD antigen in a serum/plasma sample of the test individual, (b) comparing the level of sCD antigen quantified in step (a) to a quantified level of control sCD antigen in serum/plasma samples of control subjects classified as healthy subjects; where a determination from step (b) that is statistically different from the levels in the serum/plasma samples of the subjects classified as healthy subjects, results in a classification of the sCD antigen expression in the test subject with that of the subjects classified as having AML.

A method of detecting, diagnosing or prognosing acute myeloid leukemia (AML) in a test individual the method comprising, for each of a plurality of sCD antigens, where the plurality of sCD antigens comprises one or more sCD antigens selected from the group consisting of: sCD14, sCD30, sCD54, sCD117 and sCD130, and where the plurality of sCD antigens comprises one or more sCD antigens selected from the soluble isoforms of the CD antigens listed in Table 43; (a) quantifying a level of expression of the sCD antigen in a serum/plasma sample of the test individual, (b) comparing the level of sCD antigen quantified in step (a) to a quantified level of control sCD antigen in serum/plasma samples of control subjects classified as healthy subjects; (c) comparing the level of sCD antigen quantified in step (a) to a quantified level of control sCD antigen in serum/plasma samples of control subjects classified as having AML; where a determination from steps (b) and (c) that the level of step (a) is statistically similar to the levels in the serum/plasma samples of the subjects classified as having AML, and is statistically different from the levels in the serum/plasma samples of the subjects classified as healthy subjects, results in a classification of the sCD antigen expression in the test subject with that of the subjects classified as having AML.

A method of detecting, diagnosing or prognosing acute myeloid leukemia (AML) in a test individual the method comprising, for each of a plurality of sCD antigens, where the plurality of sCD antigens comprises one or more sCD antigens selected from the group consisting of: sCD14, sCD30, sCD54, sCD117 and sCD130, and where the plurality of sCD antigens comprises one or more sCD antigens selected from the group consisting of the soluble isoforms of the CD antigens listed in Table 43; (a) quantifying a level of expression of the sCD antigen in a serum/plasma sample of the test individual, (b) comparing the level of sCD antigen quantified in step (a) to a quantified level of control sCD antigen in serum/plasma samples of control subjects classified as healthy subjects; and (c) comparing the level of sCD antigen quantified in step (a) to a quantified level of control sCD antigen in serum/plasma samples of control subjects classified as having AML; where a determination from steps (b) and (c) that the level of step (a) is statistically different from the levels in the serum/plasma samples of the subjects classified as having AML and is statistically similar to the levels in the serum/plasma samples of the subjects classified as healthy subjects, results in a classification of the sCD antigen expression in the test subject with that of the subjects who classified as healthy subjects, and where a determination from steps (b) and (c) that the level of step (a) is statistically similar to the levels in the serum/plasma samples of the subjects classified as having AML, and is statistically different from the levels in the serum/plasma samples of the subjects classified as healthy subjects, results in a classification of the antigen expression in the test subject with that of the subjects classified as having AML.

A method of detecting, diagnosing or prognosing acute myeloid leukemia (AML) in a test individual the method comprising, for each of a plurality of antigens comprising sCD antigens and MHC Class I antigens, where the sCD antigens comprises one or more sCD antigens selected from the group consisting of: sCD14, sCD30, sCD54, sCD117 and sCD130, (a) quantifying a level of expression of the antigen in a serum/plasma sample of the test individual, (b) comparing the level of antigen quantified in step (a) to a quantified level of control antigen in serum/plasma samples of control subjects classified as healthy subjects; where a determination from step (b) that is statistically different from the levels in the serum/plasma samples of the subjects classified as healthy subjects, results in a classification of the sCD antigen expression in the test subject with that of the subjects classified as having AML.

A method of detecting, diagnosing or prognosing acute myeloid leukemia (AML) in a test individual the method comprising, for each of a plurality of antigens comprising sCD antigens and MHC Class I antigens, where the sCD antigens comprises one or more sCD antigens selected from the group consisting of: sCD14, sCD30, sCD54, sCD117 and sCD130, (a) quantifying a level of expression of the antigen in a serum/plasma sample of the test individual, (b) comparing the level of antigen quantified in step (a) to a quantified level of control antigen in serum/plasma samples of control subjects classified as healthy subjects; and (c) comparing the level of antigen quantified in step (a) to a quantified level of control antigen in serum/plasma samples of control subjects classified as having AML; where a determination from steps (b) and (c) that the level of step (a) is statistically similar to the levels in the serum samples of the subjects classified as having AML, and is statistically different from the levels in the serum/plasma samples of the subjects classified as healthy subjects, results in a classification of the antigen expression in the test subject with that of the subjects classified as having AML.

A method of detecting, diagnosing or prognosing acute myeloid leukemia (AML) in a test individual the method comprising, for each of a plurality of antigens comprising sCD antigens and soluble MHC Class I antigens, where the sCD antigens comprises one or more sCD antigens selected from the group consisting of: sCD14, sCD30, sCD54, sCD117 and sCD130, (a) quantifying a level of expression of the antigen in a serum/plasma sample of the test individual, (b) comparing the level of antigen quantified in step (a) to a quantified level of control antigen in serum samples of control subjects classified as healthy subjects; and (c) comparing the level of antigen quantified in step (a) to a quantified level of control antigen in serum/plasma samples of control subjects classified as having AML; where a determination from steps (b) and (c) that the level of step (a) is statistically different from the levels in the serum/plasma samples of the subjects classified as having AML and is statistically similar to the levels in the serum/plasma samples of the subjects classified as healthy subjects, results in a classification of the antigen expression in the test subject with that of the subjects who classified as healthy subjects, and where a determination from steps (b) and (c) that the level of step (a) is statistically similar to the levels in the serum/plasma samples of the subjects classified as having AML, and is statistically different from the levels in the serum/plasma samples of the subjects classified as healthy subjects, results in a classification of the antigen expression in the test subject with that of the subjects classified as having AML.

A method of detecting, diagnosing or prognosing acute myeloid leukemia (AML) in a test individual the method comprising, for each of a plurality of antigens comprising sCD antigens and MHC Class I antigens, where the sCD antigens comprises one or more sCD antigens selected from the group consisting of: sCD14, sCD30, sCD54, sCD117 and sCD130, and one or more sCD antigens selected from the soluble isoforms of the CD antigens the listed in Table 43, (a) quantifying a level of expression of the antigen in a serum/plasma sample of the test individual, and (b) comparing the level of antigen quantified in step (a) to a quantified level of control antigen in serum/plasma samples of control subjects classified as healthy subjects; where a determination from step (b) that is statistically different from the levels in the serum/plasma samples of the subjects classified as healthy subjects, results in a classification of the sCD antigen expression in the test subject with that of the subjects classified as having AML.

A method of detecting, diagnosing or prognosing acute myeloid leukemia (AML) in a test individual the method comprising, for each of a plurality of antigens comprising sCD antigens and MHC Class I antigens, where the sCD antigens comprises one or more sCD antigens selected from the group consisting of: sCD14, sCD30, sCD54, sCD117 and sCD130, and one or more sCD antigens selected from the soluble isoforms of the CD antigens listed in Table 43, (a) quantifying a level of expression of the antigen in a serum/plasma sample of the test individual, (b) comparing the level of antigen quantified in step (a) to a quantified level of control antigen in serum/plasma samples of control subjects classified as healthy subjects; and (c) comparing the level of antigen quantified in step (a) to a quantified level of control antigen in serum/plasma samples of control subjects classified as having AML; where a determination from steps (b) and (c) that the level of step (a) is statistically similar to the levels in the serum/plasma samples of the subjects classified as having AML, and is statistically different from the levels in the serum/plasma samples of the subjects classified as healthy subjects, results in a classification of the antigen expression in the test subject with that of the subjects classified as having AML.

A method of detecting, diagnosing or prognosing (by the prognostic stratification of patients into different prognostic groups) acute myeloid leukemia (AML) in a test individual the method comprising, for each of a plurality of antigens comprising sCD antigens and soluble MHC Class I antigens, where the sCD antigens comprises one or more sCD antigens selected from the group consisting of: sCD14, sCD30, sCD54, sCD117 and sCD130, and one or more sCD antigens selected from the group of soluble isoforms of the CD antigens listed in Table 43, (a) quantifying a level of expression of the antigen in a serum/plasma sample of the test individual, (b) comparing the level of antigen quantified in step (a) to a quantified level of control antigen in serum/plasma samples of control subjects classified as healthy subjects; (c) comparing the level of antigen quantified in step (a) to a quantified level of control antigen in serum/plasma samples of control subjects classified as having AML; where a determination from steps (b) and (c) that the level of step (a) is statistically different from the levels in the serum/plasma samples of the subjects classified as having AML and is statistically similar to the levels in the serum/plasma samples of the subjects classified as healthy subjects, results in a classification of the antigen expression in the test subject with that of the subjects who classified as healthy subjects, and where a determination from steps (b) and (c) that the level of step (a) is statistically similar to the levels in the serum/plasma samples of the subjects classified as having AML, and is statistically different from the levels in the serum/plasma samples of the subjects classified as healthy subjects, results in a classification of the antigen expression in the test subject with that of the subjects classified as having AML.

A method of detecting remission of acute myeloid leukemia (AML) in a test individual suspected of being in remission of acute leukemia, the method comprising, for each of a plurality of sCD antigens, where at least one sCD antigen is selected from the group consisting of: sCD14, sCD30, sCD54, sCD117 and sCD130, (a) quantifying a level of expression of the sCD antigen in a serum/plasma sample of the test individual, (b) comparing the level of sCD antigen quantified in step (a) to a quantified level of control sCD antigen in serum/plasma samples of control subjects classified as healthy subjects; and (c) comparing the level of sCD antigen quantified in step (a) to a quantified level of control sCD antigen in serum/plasma samples of control subjects classified as having AML; where a determination from steps (b) and (c) that the level of step (a) is statistically different from the levels in the serum/plasma samples of the subjects classified as having AML and is statistically similar to the levels in the serum/plasma samples of the subjects classified as healthy subjects, is indicative of the test individual's being in full remission, and where a determination from steps (b) and (c) that the level of step (a) is statistically similar to the levels in the serum/plasma samples of the subjects classified as having AML, and is statistically different from the levels in the serum/plasma samples of the subjects classified as healthy subjects, results in a classification of the sCD antigen expression in the test subject with that of the subjects classified as having AML.

A method of detecting relapse of acute myeloid leukemia (AML) in a test individual suspected of having a relapse of AML, the method comprising, for each of a plurality of sCD antigens, where at least one sCD antigen is selected from the group consisting of: sCD14, sCD30, sCD54, sCD117 and sCD130, (a) quantifying a level of expression of the sCD antigen in a serum/plasma sample of the test individual, (b) comparing the level of sCD antigen quantified in step (a) to a quantified level of control sCD antigen in serum/plasma samples of control subjects classified as healthy subjects; (c) comparing the level of sCD antigen quantified in step (a) to a quantified level of control sCD antigen in serum/plasma samples of control subjects classified as having AML; where a determination from steps (b) and (c) that the level of step (a) is statistically different from the levels in the serum/plasma samples of the subjects classified as having AML and is statistically similar to the levels in the serum/plasma samples of the subjects classified as healthy subjects, results in a classification of the sCD antigen expression in the test subject with that of the subjects classified as not having leukemia, and where a determination from steps (b) and (c) that the level of step (a) is statistically similar to the levels in the serum/plasma samples of the subjects classified as having AML, and is statistically different from the levels in the serum/plasma samples of the subjects classified as healthy subjects, is indicative of the test individual's having a relapse of AML.

A method of monitoring the disease state of a test individual undergoing therapy for AML comprising at regular time points throughout the course of therapy, for each of a plurality of sCD antigens, where at least one sCD antigen is selected from the group consisting of: sCD14, sCD30, sCD54, sCD117 and sCD130, (a) quantifying a level of expression of the sCD antigen in a serum/plasma sample of the test individual, (b) comparing the level of sCD antigen quantified in step (a) to a quantified level of control sCD antigen in serum/plasma samples of control subjects classified as healthy subjects; and (c) comparing the level of sCD antigen quantified in step (a) to a quantified level of control sCD antigen in serum/plasma samples of control subjects classified as having AML; where a determination from steps (b) and (c) that the level of step (a) is statistically different from the levels in the serum/plasma samples of the subjects classified as having AML and is statistically similar to the levels in the serum/plasma samples of the subjects classified as healthy subjects, is indicative of the therapy being effective in the test individual, and where a determination from steps (b) and (c) that the level of step (a) is statistically similar to the levels in the serum/plasma samples of the subjects classified as having AML, and is statistically different from the levels in the serum/plasma samples of the subjects classified as healthy subjects, is indicative of the therapy not being effective in the test individual.

Embodiments of any of these methods include a plurality of ligands which bind to two or more sCD antigens, where the sCD antigens includes a first soluble CD (sCD) antigen is sCD117, or where a first soluble CD (sCD) antigen is sCD117 and a second soluble CD antigen is selected from the group consisting of: sCD14, sCD30, sCD54 and sCD130, or where a first soluble CD (sCD) antigen is sCD117, and a second and third soluble CD antigen is selected from the group consisting of: sCD14, sCD30, sCD54 and sCD130, or where a first soluble CD (sCD) antigen is sCD117, and a second, third and fourth soluble CD antigen is selected from the group consisting of: sCD14, sCD30, sCD54 and sCD130, or where a first soluble CD (sCD) antigen is sCD117, and a second, third, fourth and fifth soluble CD antigen is selected from the group consisting of: sCD14, sCD30, sCD54 and sCD130.

Embodiments of any of these methods include a plurality of ligands which bind to two or more sCD antigens, where the plurality of sCD antigens consists of a first soluble CD (sCD) antigen and a second soluble CD (sCD) antigen, where the first soluble CD (sCD) antigen is sCD117 and the second soluble CD antigen is selected from the group consisting of: sCD14, sCD30, sCD54 and sCD130, where the plurality of sCD antigens consists of a first soluble CD (sCD) antigen and a second soluble CD (sCD) antigen, and a third soluble (sCD) antigen, where the first soluble CD (sCD) antigen is sCD117, and the second soluble CD antigen and the third soluble CD antigen is selected from the group consisting of: sCD14, sCD30, sCD54 and sCD130, where the plurality of sCD antigens consists of a first soluble CD (sCD) antigen and a second soluble CD (sCD) antigen, and a third soluble (sCD) antigen, and a fourth soluble (sCD) antigen, where the first soluble CD (sCD) antigen is sCD117, and the second soluble CD antigen and the third soluble CD antigen and the fourth soluble antigen is selected from the group consisting of: sCD14, sCD30, sCD54 and sCD130, where the plurality of sCD antigens consists of two or more soluble CD (sCD) antigens selected from the group consisting of: sCD117, sCD14, sCD30, sCD54 and sCD130, where the plurality of sCD antigens consists of three or more soluble CD (sCD) antigens selected from the group consisting of: sCD117, sCD14, sCD30, sCD54 and sCD130, where the plurality of sCD antigens consists of four or more soluble CD (sCD) antigens selected from the group consisting of: sCD117, sCD14, sCD30, sCD54 and sCD130, and where the plurality of sCD antigens consists of the five soluble CD (sCD) antigens selected from the group consisting of: sCD117, sCD14, sCD30, sCD54 and sCD130. In one aspect of any of the above methods of diagnosing AML, the sensitivity is greater than 70%, 75%, 80%, 83% up to 85%. In another aspect of any of the above methods of diagnosing AML, the specificity is greater than 70%, 75%, 80%, 83%, 85%, 90%, 95% up to and including 99%. In one aspect of any of the above methods of diagnosing AML, determining the classification is made through the use of neural networks. where determining the level of each of the sCD antigens in the sample comprises contacting the sample with one or more ligands, where each of the ligands is specific for one of the sCD antigens, and measuring the level of each the sCD antigen.

In another aspect of any of the above methods and compositions, the ligand is an antibody, and the antibody is selected from the group consisting of: a polyclonal antibody, a monoclonal antibody, fv, scfv, dab, fd, fab, and fab'2. In an embodiment of the above methods, the serum/plasma sample can be substituted by a bodily fluid such as one selected from the group consisting of whole blood, plasma, lymphatic fluid, cerebrospinal fluid, synovial fluid, urine, and saliva. In an embodiment of the above methods, the level of each sCD antigen in the sample is determined comprising the following steps: i) contacting the sample with a first ligand, where the ligand specifically binds a soluble CD antigen in the sample, ii) detecting the binding of the first ligand to the sCD antigen, and iii) quantitating the level of the sCD antigen. The detecting step can be accomplished by any means including the use of a detecting antibody or fragment or derivative thereof, which specifically binds its cognate ligand. In one embodiment of the methods described herein, the ligand is attached to a surface, such as a bead, a chip, a glass surface, nitrocellulose or an ELISA plate. In an embodiment of the methods described herein, a ligand is further comprises a non-immunoglobulin scaffold which includes but is not limited to CTLA4, fibronectin, lipocallin, Rbp, Bbp ApoD, a natural bacterial receptor, staphylococcus A protein (SpA), GroEL, transferrin, tetranectin, human C-lectin, an AVIMER™ and/or an AFFIBODY™ scaffold.

BRIEF DESCRIPTION OF THE DRAWINGS

FIG. 9 illustrates the summarized intensity values for the antigens for all 47 samples using minusNegByWell.robust summarization. It is visually apparent that probe number 4 (sCD117) separates many of the different classes quite well.

FIGS. 13A-13E. Displays 2d-scatter plots for all possible pairings of sCD14, sCD30, sCD 54, sCD117, sCD130.

DETAILED DESCRIPTION OF THE INVENTION

Figure 1:
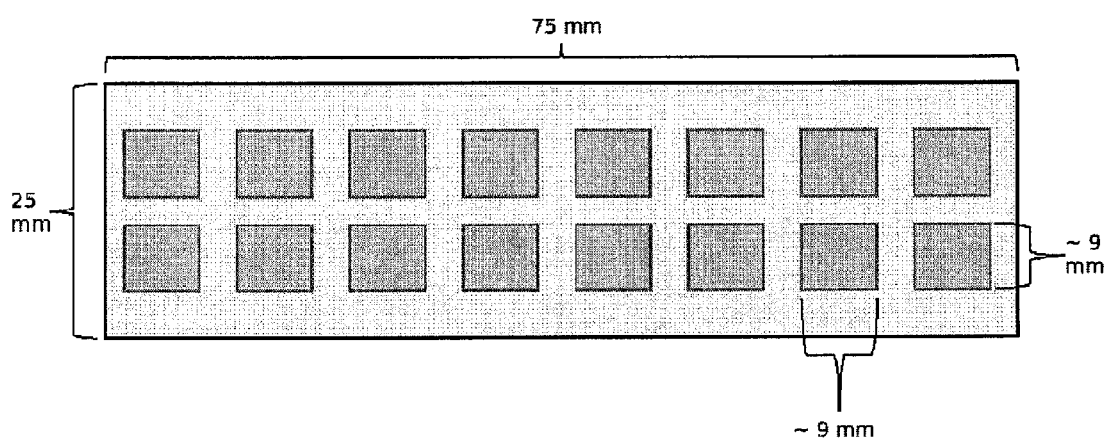
FIG. 1. Illustrates one embodiment of the layout of a chip. Each of the squares represents a well. Each well is 9×9 mm in dimension with a total number of 16 wells per chip.

Due to a large variety of molecular disease mechanisms affecting the state of the immune system, sCD data provide a highly focused, disease relevant view, permitting the use of much fewer measurements for the construction of a generic assay for diagnostics.

Modern algorithm methods allow the separation of signal signatures characteristic of specific diseases in high-dimensional input sets. The invention described herein is in the application of the concept of signature analysis in the disease relevant focus of sCD measurements.

In the prior art, sCDs have been studied individually. At most, sCDs have been studied in pairs. Conceptually, these studies are identical to biomarker studies from the prior art. These typically take one or two markers and associate them with a specific disease. This results in a simple binary result. By contrast, the present relates to the detection and derivation of sCD fingerprints, that is specific patterns. The methods of the present invention typically survey at least five different sCD entities. The resulting pattern formed by combination of these data points creates a signature or fingerprint for a particular disease state. Thus, applied to the diagnosis of a patient, at least five sCDs will be typed. The pattern or fingerprint which these multiple data points produce may then be used to deduce the diagnosis or prognosis for that patient. Thus, the diagnostic readout is linked to the specific pattern or fingerprint composed of at least five different sCDs, this fingerprint being considered as a single conceptual entity for the purposes of diagnosis. As soon as one uses more than a single predictive quantity of sCD antigens, e.g. five or more, there is no need for a significant change in expression of an individual sCD antigen to be able to discriminate disease classes using the joint set.

In this case, the features are the individual sCDs measured. It is well understood that the accuracy of a classifier generally increases with the number of features selected and, depending on the application domain, cost/benefit tradeoffs need to be made—efficient choices are certainly not arbitrary. In applications where features are cheap, such as in microarray studies, very large feature sets are therefore sometimes applied. On the other hand, very often sufficient accuracy can already be achieved for a specific disease domain with just 2-3 features, sometimes even by a single feature. In principle, several of these simple classifiers could be arbitrarily combined for assays supporting multiple disease domains. Besides issues of scaling, however, this approach would not be well suited for the development of a generic assay/sCD fingerprinting device as presented in this invention. Multiple patterns and signatures of specific diseases can be distilled de novo from large sets of feature candidates by use of modern machine learning methods, such as advanced factor analysis and algorithms for class discovery. The present invention employs sCD sets large enough to support the detection of such patterns and signatures that reflect the state of the immune system. For an implementation that demonstrates the benefits of this approach in the construction of generic disease related assays, five sCDs or more are preferable: 2-3 features would realistically only support an accurate prognosis or diagnostics for a single typical disease domain. Whereas doubling this number would, in the worst case, support two disease domains by simple aggregation, the approach of this invention utilizes patterns in a space of 5 dimensions or more allowing a high-dimensional representation of immune system states for a superior performance in the characterization of multiple disease types as required for a generic assay. Clearly, more demanding applications can be accommodated by an increase of feature numbers Assessment of sCDs, however, provides a unifying focus, even capturing clinically relevant effects of mechanistically extremely different disease types in a compact set of variables. While multiple diseases may affect the same particular sCD feature, interactions of immune system components reflected in the multi-dimensional feature set will permit efficient super-linear scaling by algorithmic separation of independent effects (e.g., by application of advanced factor analysis). We can hence use a relatively small number of sCD features for a high-dimensional representation of immune system states to provide generic disease-related assays. It is the application of this modern analytical approach to sCDs, which provide a unifying focus on immune system relevance, that underpins the present invention and that creates novel value in its clinical applications.

Further, the power of methods of the present invention lies in their capacity to read out against multiple disease states from only a single fingerprint. This feature cannot be found anywhere in the prior art. A key point to note is that the sCDs read out by the present invention may not be unique in their presence or absence or elevation or depression in a particular disease state. Indeed, numerous different disease states may possess numerous similar or identical individual marker results. Clearly, by applying the prior art techniques of biomarker assay, these disease states could never be successfully distinguished. However, the present invention advantageously permits these to be discriminated by the application of modern high-dimensional data analysis methods. This is due to the simultaneous analysis of a minimum of five different sCDs in production of the fingerprint. It is this 'parallel processing' which is both novel and inventive with regard to the state of the prior art.

Described herein are compositions and methods used to characterize a disease, disorder or condition, in an individual by analyzing the levels of soluble CD (sCD) antigens, and optionally soluble MHC Class I antigens, cytokines or chemokines, in a sample from said individual. The analysis of sCD levels in the body fluid sample can be used in many applications, including, but not limited to diagnosis, prognosis, predilection toward a specific disease or disorder, ruling out the presence of a disease or disorder, staging of the severity of the disease or disorder, monitoring the progression of the disease or disorder, and monitoring the effect of treatment or other external influence on the disease. In a preferred embodiment, the disease, disorder or condition is leukemia. The analysis of sCD levels in the sample can also be used to distinguish between a limited number of diseases, as for example, between different types of leukemia or different subtypes of leukemia.

Composition

One embodiment described herein is a composition comprising a collection of two or more, three or more, four or more, or a plurality of six or more, seven or more, eight or more, nine or more, ten or more, eleven or more, twelve or more, thirteen or more, fourteen or more, fifteen or more, sixteen or more, up to a plurality of twenty or more, thirty or more, fifty or seventy or more, one hundred or more, one hundred and fifty or more, two hundred or more, three hundred or more, three hundred and fifty or more, up to four or five hundred or more distinct, isolated ligands, each of which binds specifically to a sCD antigen, some of which have not yet been defined, and some of which have been defined but have not yet been assigned a formal CD nomenclature.

In one embodiment, the composition of ligands comprises ligands that bind specifically to a sCD antigen, the sCD antigen including soluble/shed/secreted isoforms of all the CD antigens listed in Table 43, or fragments thereof. In another embodiment, the sCD molecules include the soluble/shed/secreted forms of any sub-grouping of two or more soluble isoforms of the CD antigens listed in Table 43, or fragments thereof. In one embodiment, the sCD antigens include soluble/shed/secreted forms of all the CD antigens listed in Table 44, or fragments thereof. In another embodiment, the sCD molecules include the soluble/shed/secreted forms of any sub-grouping of two or more of the CD antigens listed in soluble isoforms of the CD antigens listed in Table 44, or fragments thereof. In one embodiment, the sCD antigens include soluble/shed/secreted forms of all the CD antigens listed in Table 45, or fragments thereof. In another embodiment, the sCD molecules include the soluble/shed/secreted forms of any sub-grouping of two or more soluble isoforms of the CD antigens listed in Table 45, or fragments thereof. In yet another preferred embodiment, the sCD antigens include soluble/shed/secreted forms of the following CD antigens: CD14, CD30, CD54, CD117 and CD130, or fragments thereof. In another embodiment, the sCD molecules include the soluble/shed/secreted forms of any sub-grouping of two or more of: CD14, CD30, CD54, CD117 and CD130, or fragments thereof.

In another embodiment, the composition of ligands, which comprises ligands that bind specifically to a sCD antigen as described above, may also contain ligands that serve as controls for the assay, including positive and/or negative controls. In one embodiment, the composition of ligands comprises ligands which bind specifically to a sCD antigen that are present in replicate, e.g. in duplicate, or triplicate, or four times in replicate, or five times in replicate, or six times in replicate, or up to 10, 20, up to 50 times in replicate.

The term "sCD antigen" is used interchangeably with the terms "soluble CD antigen", "shed CD antigen" and "secreted CD antigen". All four terms represent a soluble isoform of a CD antigen listed in Table 43, or a fragment thereof, or a spliced or alternatively spliced CD antigen, where the sCD antigen is located extracellularly. In one embodiment, an sCD antigen is found soluble in the serum/plasma and in other body fluids. A sCD molecule can be generated as the result of a process of alternative splicing (Woolfson and Milstein, PNAS, 91 (14) 6683-6687 (1994)) or cell surface shedding, or it can be made recombinantly. Advantageously, as herein defined, a shed form of sCD is generated by various mechanisms including, but not limited to, any of those selected from the group consisting of the following: alternative splicing, proteolytic cleavage and dissociation. The methods describe herein also include measurement of a sCD antigen and/or a soluble MHC class I antigen in a body fluid of an individual who has had been administered one or more sCD antigens and/or one or more soluble MHC class I antigens as part of a therapeutic procedure. In one embodiment, is the detected antigen is a fragment of a CD antigen or a sCD antigen, where one of the protein determinants or epitopes on the fragment maintains its ability to specifically bind an antibody, which specifically binds the respective sCD antigen from which the fragment is derived.

The ligand used to recognise the sCD antigen may be any molecule whether natural or synthetic which specifically binds a sCD antigen. The ligand may be engineered, for example the protein gene product of an artificial construct consisting of an expressed fragment derived from an antibody molecule with its antigen binding region intact, or the ligand may be a non-protein molecule, or a protein molecule which is not an antibody, for example a derivative of an antibody, for example made by introducing antibody binding regions, e.g. CDRs, into a non antibody scaffolding, as described below. In one embodiment, the antibody used to recognise the soluble CD molecule may be monoclonal or may be polyclonal.

The invention includes methods comprising comparisons of differences in expression levels between different clinical body fluid samples or in the case of gene expression analysis differences in expression levels between different clinical tissue-derived RNA samples, and thus determining relative levels. Comparison of expression levels can be done visually or manually, or can be automated and done by a machine, using, for example, optical detection means. Subrahmanyam et al., 97 BLOOD 2457 (2001); Prashar et al., 303 METHODS ENZYMOL. 258 (1999). Hardware and software for analyzing differential expression of genes are available, and can be used in practicing the present invention. See, e.g., GenStat Software and GeneExpress.®. GX Explorer.®. Training Manual; Baxevanis et al., 7 CURR. OPIN. BIOTECHNOL. 102 (1996).

Gene symbols written in this application using all capital letters refer to human genes to which such symbol has been assigned as its Official Symbol by The Human Genome Organisation (HUGO) Gene Nomenclature Committee.

As used herein, "a" or "an" means "at least one" or "one or more."

"Diagnosis" generally includes a determination of a subject's susceptibility to a disease or disorder, a determination as to whether a subject is presently affected by a disease or disorder, a prognosis of a subject affected by a disease or disorder, and therametrics (e.g., monitoring a patient's condition to provide information as to the effect or efficacy of therapy).

"Expression" generally refers to transcriptional or translational activity of a partial or entire gene, post-transcriptional or translational activities, e.g., activation or stabilization of a partial or entire gene, or the presence of any detectable level of one or more partial or entire transcription or translation products of a gene.

"Gene" refers to a polynucleotide sequence that comprises coding sequences, and optionally control sequences necessary for the production of a polypeptide or precursor. The polypeptide can be encoded by a full length coding sequence or by any portion of the coding sequence. A gene may constitute an uninterrupted coding sequence or it may include one or more introns, bound by the appropriate splice junctions. Moreover, a gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides.

"Gene product" refers to a biomolecule, such as a protein or mRNA, that is produced when a gene in an organism is transcribed or translated or post-translationally modified.

"Hybridization" refers to any process by which a polynucleotide sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency.

"Kit" refers to a combination of physical elements, e.g., probes, including without limitation specific primers, labeled nucleotide acid probes, antibodies, protein-capture agent(s), reagent(s), instruction sheet(s) and other elements useful to practice the invention. These physical elements can be arranged in any way suitable for carrying out the invention. For example, probes can be provided in one or more containers or in an array or microarray device.

"Predisposition" or "predilection" to a disease refers to an individual's susceptibility to such disease. Individuals who are susceptible are statistically more likely to have a particular disease than normal/wild type individuals.

Prognosis" refers to the art or act of foretelling the course of a disease or disorder. Additionally, the term refers to the prospect of survival and recovery from a disease or disorder as anticipated from the usual course or indicated by special features of the individual's case. Further, the term refers to the art or act of identifying a disease or disorder from its signs and symptoms.

The phrase "binds specifically" or "specifically binds" refers to the interaction of a ligand to its receptor or binding moiety, e.g., a CD specific ligand to a sCD antigen, with a Kd value greater than 1 Molar preferably $10^7$ M−1 or greater, more preferably $10^8$ M−1 or greater, and most preferably $10^9$ M−1 or greater. Preferably, a CD specific ligand will specifically bind a target sCD antigen or epitope with an affinity of less than 500 nM, preferably less than 200 nM, and more preferably less than 10 nM, such as less than 500 pM. The binding affinity, Kd rate constant is defined as $K_{off}/K_{on}$, and can be measured in many ways well known to one of skill in the art, including measurement by Scatchard analysis and by surface plasmon resonance. Standards techniques for surface plasmon resonance (SPR) assays include Jan Terje Andersen et al. (2006) Eur. J. Immunol. 36:304-3051; Fagerstam (1991) Tech. Protein Chem. 2:65-71; and Johnsson et al (1991) Anal. Biochem. 198:268-277. The phrase "binds specifically" or "specifically binds" can also refer to the interaction of a ligand to its receptor or binding moiety, e.g., a CD specific ligand to a sCD antigen, in terms of binding with an affinity that is at least two-fold, 50-fold, 100-fold, or greater than its affinity for binding to a non-specific antigen (e.g., BSA).

The term "cytokine" is used broadly herein to refer to soluble glycoproteins that are released by cells of the immune system and act non-enzymatically through specific receptors to regulate immune responses. As such, the term "cytokine" as used herein includes chemokines, interleukins, lymphokines, monokines, interferons, colony stimulating factors, platelet activating factors, tumor necrosis factor-α, and receptor associated proteins, as well as functional fragments thereof.

Cytokines are well known in the art and include, for example, endothelial monocyte activating polypeptide II (EMAP-II), granulocyte-macrophage colony stimulating factor (GM-CSF), granulocyte-CSF (G-CSF), macrophage-CSF (M-CSF), IL-1, IL-2, IL-3, IL-4, IL-5, IL-6, IL-10, IL-12, IL-13, etc., the interferons, including IFNα, IFNβ and IFNγ, and TNF-☐, each of which is associated with a particular biologic, morphologic, or phenotypic alteration in a cell or cell mechanism.

The chemokines are further exemplified by the members of the CXC chemokine (or α) subfamily, which possess an intervening amino acid between the first two conserved cysteines; the members of the CC (or β subfamily, which do not contain such an intervening amino acid residue; and the C (or γ) chemokines, which lack the first and third cysteine residues. In general, the α chemokine members are active on neutrophils and T lymphocytes (T cells), and the β chemokines are active on monocytes, macrophages and T cells. Several members of the α and β chemokine sub-families also are active on dendritic cells, which are migratory cells that exhibit potent antigen-presenting properties and are thought to participate in the pathophysiology of many inflammatory diseases (Xu et al., J. Leuk. Biol., 60:365-71, 1996; and Sozzani et al., J. Immunol., 159:1993-2000, 1997). A fourth human CX3C-type chemokine, fractalkine, also has been described (Bazan et al., Nature, 385:640-4, 1997; Imai et al., Cell, 91:521-30, 1997; Mackay, Curr. Biol. 7:R384-6, 1997). Unlike other chemokines, fractalkine exists in membrane and soluble forms. The soluble form is a potent chemoattractant for monocytes and T cells. The cell surface receptor for this chemokine is termed CX3CR1.

The ☐ chemokines (also known as IL-8) are exemplified by granulocyte chemotactic protein-2 (GCP-2); growth-related oncogene-α (GRO-α) GRO-β, and GRO-γ; epithelial cell-derived neutrophil activating peptide-78 (ENA-78); platelet basic protein (PBP); connective tissue activating peptide III (CTAP III); neutrophil activating peptide-2 (NAP-2); low affinity platelet factor-4 (LAPF-4); monokine induced by IFNγ (MIG); platelet factor 4 (PF4); interferon inducible protein 10 (IP-10); the stromal cell derived factors SDF-1α, SDF-1β, and SDF-2. The β chemokines are exemplified by the monocyte chemotactic proteins MCP-1, MCP-2, MCP-3, MCP-4, and MCP-5; the macrophage inhibitory proteins MIP-1α, MIP-1β, MIP-1γ, MIP-2, MIP-2α, MIP-2β, MIP-3α, MIP-3β, MIP-4, and MIP-5; macrophage-derived chemokine (MDC); human chemokine 1 (HCC-1); LD78β; RANTES; eotaxin 1; eotaxin 2; TARC; SCYA17 and I-309; dendritic cell chemokine-1 (DC-CK-1). The γ chemokines are exemplified by lymphotactin.

As used herein, "biological sample" or "sample" encompasses a variety of sample types obtained from an organism, human or otherwise, that can be used in a diagnostic or monitoring assay. The definition encompasses blood and other liquid samples of biological origin, solid tissue samples, such as a biopsy specimen, or derived tissue cultures or cells, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples. Generally, the sample will be, or be derived from, peripheral (or circulating) blood. In some cases, the blood will have been enriched for a macrophage fraction, by using, for example, glass or plastic adherence. Alternatively, mononuclear cells may also be purified using Percoll gradients.

As used herein, the term "antibody," includes, but is not limited to a polypeptide substantially encoded by an immunoglobulin gene or immunoglobulin genes, an IgG antibody, an IgM antibody, or a portion thereof, or fragments thereof, which specifically bind and recognize an analyte, antigen or antibody. "Antibody" also includes, but is not limited to, a polypeptide substantially encoded by an immunoglobulin gene or immunoglobulin genes, or fragments thereof, which specifically bind and recognize the antigen-specific binding region (idiotype) of antibodies produced by a host in response to exposure to the analyte.

As used herein, the term "antibody," encompasses polyclonal and monoclonal antibody preparations, as well as preparations including monoclonal antibodies, polyclonal antibodies, hybrid antibodies, phage displays, altered antibodies, F(ab')2 fragments, F(ab) fragments, Fv fragments, single domain antibodies, chimeric antibodies, humanized antibodies, dual specific antibodies, bifunctional antibodies, single chain antibodies, and the like, and functional fragments and multimers thereof, which retain specificity for an analyte or antigen. For example, an antibody can include variable regions, or fragments of variable regions, and multimers thereof, which retain specificity for an analyte or antigen. See, for example, Paul, Fundamental immunology, 3rd Ed., 1993, Raven Press, New York, for antibody structure and terminology. The antibody or portion thereof, may be derived from any mammalian species, e.g., from a mouse, goat, sheep, rat, human, rabbit, or cow antibody. An antibody may be produced synthetically by methods known in the art, including modification of whole antibodies or synthesis using recombinant DNA methodologies. Antibodies may be labelled with detectable moieties by one of skill in the art. In some embodiments, the antibody that binds to an entity one wishes to measure (the primary antibody) is not labelled, but is instead detected by binding of a labelled secondary antibody that specifically binds to the primary antibody. In one preferred antibody embodiment, the antibody YTH, or which is an MHC class I antibody, and binds soluble MHC class I antigen, and can be used to detect soluble MHC Class I antigens in the methods and products comprising ligands described herein.

Techniques for the preparation of antibodies, are, for example, described in the following reviews and the references cited therein: Winter & Milstein, (1991) Nature 349: 293-299; Plueckthun (1992) Immunological Reviews 130: 151-188; Wright et al., (1992) Crit. Rev. Immunol. 12:125-168; Holliger, P. & Winter, G. (1993) Curr. Op. Biotechn. 4, 446-449; Carter, et al. (1995) J. Hemather. 4, 463-470; Chester, K. A. & Hawkins, R. E. (1995) Trends Biotechn. 13, 294-300; Hoogenboom, H. R. (1997) Nature Biotechnol. 15, 125-126; Fearon, D. (1997) Nature Biotechnol. 15, 618-619; Plückthun, A. & Pack, P. (1997) Immunotechnology 3, 83-105; Carter, P. & Merchant, A. M. (1997) Curr. Opin. Biotechnol. 8, 449-454; Holliger, P. & Winter, G. (1997) Cancer Immunol. Immunother. 45, 128-130.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum, albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

An "isolated" ligand is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the ligand will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated ligand will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid support" is meant a non-aqueous matrix to which the ligand, e.g., antibody, of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

"Ligand" as used herein is any molecule that is capable of specifically binding to or reacting with a molecule, the molecule including, but preferably not limited to a soluble CD antigen, a soluble MHC Class I antigen and a chemokine. A ligand can be a peptide molecule or a non-peptide organic molecule, as described in U.S. Pat. Nos. 6,130,231; 6,153,628; 6,322,770; and PCT publication WO 01/97848, incorporated herein by reference. "Non-peptide" molecules, in general, are molecules other peptide, i.e., simply polymers of amino acids, either gene encoded or non-gene encoded. Thus, "non-peptide ligands" are moieties, which are commonly referred to as "small molecules"; in some embodiments non-peptide ligands are lacking in polymeric character and characterized by the requirement for a core structure other than a polymer of amino acids. The non-peptide ligands may be coupled to peptides or may include peptides coupled to portions of the ligand which are responsible for affinity to its respective binding molecule, e.g., a sCD antigen or soluble MHC Class I antigen, but it is the non-peptide regions of this ligand which account for its binding ability. A ligand can also be a polypeptide that specifically binds an epitope on an antigen, and the ligand can be, for example, an antibody.

The phrase "selectively binds" is used interchangeably with the phrase "specifically binds"; the two phrases having identical definitions. A protein epitope is a recognition site that comprises a minimum of three amino acids, and can include many more amino acids. An epitope can also recognize non-polypeptide moieties, or moieties that are a mixture of polypeptides and non-polypeptide determinants.

In one embodiment, a ligand comprises a non-immunoglobulin scaffold, e.g., CTLA4, fibronectin, lipocalin, e.g., lipocalins Rbp, Bbp or ApoD, a natural bacterial receptor such as staphyloccocus A protein (SpA) or GroEL, transferrin, e.g., Biorexus's Trans-body™ tetranectin e.g., human C-lectin, an Avimer™ and an Affibody™ scaffold, and further comprises one or more sites that specifically binds an epitope on an antigen, e.g. sCD antigen or soluble MHC Class I antigen, where the one or more sites that specifically bind an antigen are preferably on the surface of the non-immunoglobulin scaffold. Thus a ligand for a sCD antigen or a soluble MHC Class I antigen can comprise a non-immunoglobulin scaffold and one or more epitope interaction sites which are preferably on the surface of the non-immunoglobulin scaffold, where the epitope interaction site specifically binds a sCD antigen or a soluble MHC Class I antigen, respectively. The non-immunoglobulin scaffold can be a human, non-human, synthetic, or semi-synthetic scaffold that is a scaffold other than an antibody scaffold. Yet further, alternative protein scaffolds that are loosely based around the basic fold of antibody molecules have been suggested and may be used in the preparation of inventive interaction partners (e.g., see Ku and Schultz Proc. Natl. Acad. Sci. USA. 92:6552, 1995). Antibody mimics comprising a scaffold of a small molecule such as 3-aminomethylbenzoic acid and a substituent consisting of a single peptide loop have also been constructed. The peptide loop performs the binding function in these mimics (e.g., see Smythe et al., J. Am. Chem. Soc. 116:2725, 1994). A synthetic antibody mimic comprising multiple peptide loops built around a calixarene unit has also been described (e.g., see U.S. Pat. No. 5,770,380 to Hamilton et al.).

In a preferred embodiment, the epitope interaction site specifically binds a sCD antigen. In another preferred embodiment, the epitope interaction site specifically binds a soluble MHC Class I antigen. In a preferred embodiment, the epitope interaction site comprises one or more CDR regions, e.g., one or two or three of CDR1, CDR2 and CDR3 from an immunoglobulin variable domain. In a further preferred embodiment, the epitope interaction site is composed of one or more CDRs grafted on to a non immunoglobulin scaffold, including, but preferably not limited to, CTLA4, fibronectin, lipocallin, e.g., lipocalins plasma retinol binding protein (Rbp), bilin binding protein (Bbp) or Apolipoprotein (ApoD), a natural bacterial receptor such as staphyloccocus A protein (SpA) or GroEL, an Avimer™ and an Affibody™ scaffold. In a further preferred embodiment, the epitope interaction site comprises one or two or three of CDR1, CDR2 and CDR3 from an immunoglobulin variable domain, preferably from a single variable domain. These CDR regions can be provided on a heavy or a light immunoglobulin chain framework region, as well as a non-immunoglobulin scaffold. Alternatively, one or more antibody V regions are provided on a non-immunoglobulin scaffold. Immunoglobulin frameworks include but are not limited to one or more VH frameworks, such as VH3 and VHH frameworks described supra, as well as VL frameworks, including Vkappa and Vlambda frameworks. In some embodiments, the variable domain comprises at least one human framework region having an amino acid sequence encoded by a human germ line antibody gene segment, or an amino acid sequence comprising up to five amino acid differences relative to the amino acid sequence encoded by a human germ line antibody gene segment. In other embodiments, the variable domain comprises four human framework regions, FW1, FW2, FW2 and FW4, having amino acid sequences encoded by a human germ line antibody gene segment, or the amino acid sequences of FW1, FW2, FW3 and FW4 collectively containing up to ten amino acid differences relative to the amino acid sequences encoded by the human germ line antibody gene segment. Suitable scaffolds and techniques for such CDR grafting or Variable region grafting will be clear to the skilled person and are well known in the art, see for example U.S. application Ser. No. 07/180,370, WO 01/27160, EP 0 605 522, EP 0 460 167, U.S. application Ser. No. 07/054,297, Nicaise et al., Protein Science (2004), 13:1882-1891; Ewert et al., Methods, 2004 October; 34(2):184-199; Kettleborough et al., Protein Eng. 1991 October; 4(7): 773-783; O'Brien and Jones, Methods Mol. Biol. 2003: 207: 81-100; and Skerra, J. Mol. Recognit. 2000: 13: 167-187, and Saerens et al., J. Mol. Biol. 2005 Sep. 23; 352(3):597-607, and the further references cited therein.

One or more of the ligands specific for a sCD antigen can further contain one or more entities including, but preferably is preferably not limited to, a label, a tag and a drug. Such ligand can be present in a kit, a composition, including a pharmaceutical composition, containing one or more of the ligands, preferably a plurality of the ligands and a carrier thereof.

As used herein the term a 'sCD sub-category' describes a sub-group of sCDs, which show a defined fingerprint/profile (sub-fingerprint) of sCD levels within a larger fingerprint of one or more disease states wherein each sub-group of sCDs exhibits common characteristics distinguishing it from any other sub-group within those one or more disease states.

In a further aspect still, the present invention provides a sCD reference database comprising pathological and/or healthy sCD fingerprint patterns and/or sCD fingerprints from individuals without the disease or condition in question.

In a further aspect still, the present invention provides a sCD/soluble MHC class I/cytokine/chemokine reference database comprising pathological and/or healthy sCD soluble MHC class I/cytokine/chemokine fingerprint patterns and/or sCD soluble MHC class I/cytokine/chemokine fingerprints from individuals without the disease or condition in question.

In a farther aspect still, the present invention provides a sCD reference database comprising pathological and/or healthy sCD fingerprint patterns and/or sCD fingerprints from individuals without the disease or condition in question or a sCD/soluble MHC class I/cytokine/chemokine patterns and/or sCD soluble MHC class I/cytokine/chemokine fingerprints from individuals without the disease or condition in question in combination with corresponding gene expression signatures. The term "RT-PCR" has been variously used in the art to mean reverse-transcription PCR (which refers to the use of PCR to amplify mRNA by first converting mRNA to double stranded cDNA) or real-time PCR (which refers to ongoing monitoring in "real-time" of the amount of PCR product in a reaction in order to quantify the amount of PCR target sequence initially present. As used herein, the term "RT-PCR" means reverse transcription PCR. The term "quantitative RT-PCR" (qRT-PCR) means real-time PCR applied to determine the amount of MRNA initially present in a sample.

The term "response" means any measure of patient response to treatment with a drug including those measures ordinarily used in the art, such as complete pathologic response, partial response, stable disease, time to disease progression, etc.

The term "microarray" refers to an ordered arrangement of hybridizable array elements, preferably polynucleotide probes, on a substrate. Microarrays include, without limitation, an ordered arrangement of polynucleotide probes on a microchip and a collection of polynucleotide coated beads on an arrangement of microfibers.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more unusual bases, such as inosine or one or more modified bases such as tritiated bases. Moreover the term includes DNAs (including cDNAs) and RNAs that contain one or more modified sugars, such as in locked nucleic acids. DNAs or RNAs with modified backbones, such as for example, phosphorothioates and peptide nucleic acids, and DNAs or RNAs with modified 5' or 3' phosphate moieties such as for example when conjugated with minor groove binders, are "polynucleotides" as that term is intended herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. Modified bases can be readily incorporated into chemically synthesized oligonucleotides made using automated synthesizers.

Oligonucleotides can also be made by a variety of other methods, including in vitro recombinant DNA-mediated techniques and by expression of DNAs in cells and organisms.

The term "gene expression" describes the conversion of DNA gene sequence information into transcribed RNA (either the initial unspliced RNA transcript or the mature MRNA) or the encoded protein product. Gene expression can be monitored by measuring the levels of either RNA or protein products of the gene or subsequences.

The phrase "gene amplification" refers to a process by which multiple copies of a gene or gene fragment are formed in a particular cell or cell line. The duplicated region (a stretch of amplified DNA) is often referred to as "amplicon." Often, the amount of the messenger RNA (mRNA) produced, i.e., the level of gene expression, also increases in proportion to the number of copies made of the particular gene expressed.

"Antibody-capture agent" refers to a molecule or a multi-molecular complex that can bind an antibody to itself. The protein-capture agent may comprise a biomolecule such as a protein or a polynucleotide. Examples of antibody-capture agents include immunoglobulins, antigens, receptors, or other proteins, or portions or fragments thereof.

The terms "signature," "gene expression signature," "molecular signature," and "genetic fingerprint," all used interchangeably herein, refer to a group of genes or gene products which represent a particular physiological state including diseased, and non diseased. They can be characterized by an increased or decreased expression in individuals with disease relative to those without disease; and may show a high degree of correlation of signals with each other; and may display a similar time course of expression.

"Transcript" refers to an RNA product transcribed from DNA. The category of "transcripts" includes, but is not limited to, pre-mRNA nascent transcripts, transcript processing intermediates, mature mRNAs and degradation products thereof.

Throughout this specification, the word "comprise," or variations thereof, will be understood to imply the inclusion of a stated element, integer or step, or group of elements, integers or steps, but not the exclusion of any other element, integer or step, or group of elements, integers or steps.

The pattern of expression exhibited by the sCD antigens and/or soluble MHC antigens and/or cytokines and/or chemokines from a body fluid may be captured by any method known to the art.

Arrays

In some embodiments, solid surfaces are chemically patterned for attachment of biological macromolecules (e.g., nucleic acids or proteins). In some embodiments, the present invention further provides solid supports comprising arrays of biological macromolecules. In preferred embodiments, arrays comprise at least 50, preferably at least 100, even more preferably at least 1000, still more preferably, at least 10,000, and yet more preferably, at least 100,000 distinct biological macromolecules. In preferred embodiments, each distinct biological macromolecule is addressed to a specific location on the array. This allows simultaneous screening of all the arrayed molecules, and allows for the immediate identification of any molecule that interacts with a cell product. In preferred embodiments, each addressable location is larger than 25, and preferably, larger than 50 microns.

The present invention is not limited to a particular method of fabrication or a specific type of array. Any number of suitable chemistries known to one skilled in the art may be utilized. In preferred embodiments, the target molecules are attached to the substrate by a cleavable disulfide bond. In some embodiments, target molecules are attached to surfaces configured for label-free (e.g., SPR) detection. Target molecules are contemplated to comprise proteins, enzymes, or other ligands of soluble CD antigens and/or soluble MHC Class I antigens. In some preferred embodiments, arrays of molecules are attached to the solid surfaces. In some embodiments, multiple copies of the same molecule targets are attached to different places on the array. In other embodiments, different target molecules are attached to each place on the array.

An exemplary method is through the use of microarrays, for example, using protein microarrays, peptide microarrays, or combinations thereof. Microarrays refer to surface microarrays, membrane microarrays, bead microarrays, solution microarrays, and the like comprised of discrete proteins, antibodies, protein fragments, antibody fragments, antibody-mimetics, peptides, peptide-mimetics, organic molecules and/or other molecules capable of selectively and specifically binding the sCD antigens and/or soluble MHC antigens, thus permitting their detection and measurement for the purpose of capturing a pattern of expression.

The detection of sCD antigens and/or soluble MHC antigens and/or chemokines, cytokines, and other antigens from a body fluid may include multiple mass spectrophotometric analyses performed in parallel or any other method of detecting hundreds to thousands of proteins or peptide fragments derived therefrom at one time from a single body fluid sample from a single individual. The antigens and ligands specific to these antigens are detected using mass spectrophotometric, fluorescent, radioactive or other techniques and the expression levels of each soluble CD antigen or soluble MHC antigen is assessed.

In yet another embodiment of the invention, the determination of a pattern of expression further comprises ranking the captured pattern of expression of sCD antigens and/or soluble MHC antigens from a body fluid. The expression levels of the antigens, captured on the antibody or other type of microarray, are ranked from the lowest expressed protein being assigned a rank of 1 to the most highly expressed protein. For example, if 100,000 proteins were assessed from a single blood sample, the lowest expressed protein would be assigned a value of 1 and the most highly expressed protein a value of 100,000 with every other protein having a value in between. The ranks of the proteins with individuals with a specific disease or disorder or undergoing a specific treatment are compared to other individuals with other conditions, the same condition, or to normal healthy controls.

Any expression method known in the art may be used to define the pattern of expression captured. A preferred method is the Significance Analysis of Microarrays (SAM) and class prediction, as taught by Tusher, Proceedings National Academy of Sciences, 98: 5116 (2001); Golub et al., Science, 286: 531-537 (1999). Other expression methods are available, including neural network modelling, clustering, computer programs, and entropy methods, and could be used as alternatives. The significance analysis of microarray (SAM) and class prediction may be used to define the pattern of expression captured. The significance analysis of microarrays uses permutations of repeated measurements to estimate the percentage of sCD and soluble MHC Class I antigens or cytokines or chemokines identified by chance. Once the molecules are identified that are regulated in a specific disease or condition, this set of molecules is said to define the pattern expression for that disease or condition. To determine whether a test sample is consistent with the normal pattern of expression or is consistent with the pattern for a specific disease or disorder, the following general procedure is followed. The expression value for each soluble CD antigen and/or soluble MHC Class I antigen or cytokines or chemokines in the test sample is compared to the expression value in the normal sample. A class prediction method is then used to determine whether the test sample fits the normal or diseased pattern.

To do this, the expression value for soluble antigen is determined to be closer to the control or the diseased state, and a weighted vote is made for each molecule for the injury pattern. The diagnosis or detection of the disease is made if PS>0.3 when PS is the prediction strength, defined as PS=(Vw−VL)/(Vw+VL). If there is no difference between the samples, then PS will equal zero and the sample would fall in the class of the control or healthy body fluid sample. If PS>0.3, then the sample would be classified as the diseased state. In one embodiment of the invention, the most regulated proteins for a given condition that had the lowest variance may be identified using SAM analysis for various medical, neurological, genetic and other conditions. These regulated genes or proteins may be used to define a pattern for each condition, a class prediction, or classification that would be used to analyze unknown samples to determine whether they would fit the pattern for a specific disease or condition or not with a 90, 95 or 99% confidence level.

Once the pattern of expression is captured and defined, the pattern of expression exhibited by the test body fluid is compared to a database such as described above, to assess the detection and/or diagnosis of a specific disease. This database may comprise a pattern of expression or multiple patterns of expression based on a specific body fluid, a specific disorder or disease, or combinations thereof. Further, the database may be a commercially available database or a database created from the pattern of expression of the soluble antigens captured and defined by the obtained body fluids for a host of different patients or healthy individuals. As herein described the term 'a reference database' refers to a collection of sCD fingerprints from healthy 'non-diseased' and/or diseased individuals. Advantageously, the database is computer generated and/or stored. Advantageously the data from more than 5 individuals is present in the database.

More advantageously the data from more than 25, 10, 100, or 1000 individuals comprises the database. Advantageously the database, in addition to sCD data and data from gene fingerprinting analyses, will also comprise clinical information relating to various patients and/or disease conditions.

As used herein the term "assessing (or assessed)" is intended to include quantitative and qualitative determination of the identity and/or quantity of a moiety, e.g., a protein or nucleic acid, present in the sample or on the microdevices or in whatever form or state. Assessment would involve obtaining an index, ratio, and percentage, visual or other value indicative of the identity of a moiety in the sample and may further involve obtaining a number, an index, or other value indicative of the amount or quantity or the concentration of a moiety present in the sample or on the microdevice or in whatever form or state. Assessment may be direct or indirect.

Immunoassay

As described above, in one embodiment, a sCD specific ligand and/or a soluble MHC specific ligand or a cytokine specific ligand or a chemokine specific ligand is an antibody. A variety of immunoassay formats built around chemiluminescent, ELISA, fluorescence or radio-immunoassay technologies, can be used in the methods described herein comprising detecting and/or quantitating the level of soluble CD antigens and/or soluble MHC Class I antigens and/or chemokines and or cytokines in the body fluid from an individual. For example solid-phase ELISA immunoassays are routinely used to bind ligands, especially monoclonal antibodies, specifically immunoreactive with an analyte, and can be readily adapted to binding soluble CD antigens, and/or cytokines, and/or chemokines and/or soluble MHC Class I antigens. See Harlow and Lane, ANTIBODIES: A LABORATORY MANUAL, Cold Springs Harbor Publications, New York, (1988) for a description of immunoassay formats and conditions that can be used to determine specific immunoreactivity. Typically a specific or selective reaction will be at least twice background signal to noise, and more typically more than 10 to 100 times greater than background.

Luminex

As described in 20070178607, the use of microparticles allows performance of the assays to detect sCD antigens, and/or cytokines, and/or chemokines and/or soluble MHC Class I antigens in a small, well-mixed volume with favorable binding kinetics. An example of fluorescence-based particle identification is Luminex Corporation's FlowMetrix™ system and Laboratory Multi-Analyte Profiling (LabMAP™) technology. This system allows up to about 100 to 1000 analytes to be measured sequentially by flow cytometry. This technology incorporates microspheres that are internally labeled with two or more distinct fluorescent dyes. The microspheres are further coded with varying combinations of intensities of the fluorophores. The process also includes a third different fluorophore integrated to a reporter molecule for quantification of reactions on the surface of the encoded microspheres. The fabrication of the encoded microspheres and the system is described in, for example, Chandler, V. S., et al., "Multiplexed analysis of clinical specimens apparatus and methods, U.S. Pat. No. 5,981,180 (1999). Due to the relatively wide emission spectra of many fluorophores, a moderate number of patterns can be uniquely distinguished with this class of labels, typically less than 1000.

Chips

In some embodiments, the solid support is a "chip." As used herein, "chip" refers to a solid substrate with a plurality of one-, two- or three-dimensional micro-structures or micro-scale structures on which certain processes, such as physical, chemical, biological, biophysical or biochemical processes, etc., can be carried out. The micro-structures or micro-scale structures such as: channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips used in the present invention can vary considerably, e.g., from about 1 $mm^2$ to about 0.25 $m^2$. Preferably, the size of the chips is from about 4 $mm^2$ to about 25 $cm^2$ with a characteristic dimension from about 1 mm to about 7.5 cm. The chip surfaces may be flat, or not flat. The chips with non-flat surfaces may include channels or wells fabricated on the surfaces. Chips may be made of any suitable material including, but not limited to, metal, plastic, polymer, and glass. Several commercial sources for chips, with and without already arrayed biological molecules, exist. Commercial sources include, but are not limited to, Motorola, Schaumburg, Ill.; ACLARA BioSciences, Inc., Hayward, Calif.; Agilent Technologies Inc., Palo Alto, Calif.; Aviva Biosciences Corp., Dan Diego, Calif.; Caliper Technologies Corp., Palo Alto, Calif.; Clontech, Palo Alto, Calif.; Corning, Acton, Mass.; Gene Logic Inc., Columbia, Md.; Hyseq Inc., Sunnyvale, Calif.; Incyte Genomics, Palo Alto, Calif.; Micronics Inc., Redmond, Wash.; Mosaic Technologies, Waltham, Mass.; OriGene Technologies, Rockville, Md.; Packard Instrument Corp., Meriden, Conn.; Rosetta Inpharmatics, Kirkland, Wash.; Sequenom, San Diego, Calif., and GenTel Biosciences.

SPR Surfaces

In other embodiments, the solid support is an SPR surface, as described in US Patent publication 20040147045. Surface Plasmon Resonance (SPR) techniques involve a surface coated with a thin film of a conductive metal, such as gold, silver, chrome or aluminum, in which electromagnetic waves, called Surface Plasmons, can be induced by a beam of light incident on the metal glass interface at a specific angle called the Surface Plasmon Resonance angle. Modulation of the refractive index of the interfacial region between the solution and the metal surface following binding of the captured macromolecules causes a change in the SPR angle which can either be measured directly or which causes the amount of light reflected from the underside of the metal surface to change. Such changes can be directly related to the mass and other optical properties of the molecules binding to the SPR device surface. Several biosensor systems based on such principles have been disclosed (see e.g., WO 90/05305). In some embodiments, the metal (e.g., gold) layer is chemically patterned for attachment of molecular probes (e.g., biomolecules). In other embodiments, antibodies are utilized for enhancing the SPR signal generated by cellular item target molecule complexes. The cellular item directly binds to the arrayed target molecule. In some embodiments, the SPR signal is then enhanced by the binding of an antibody to the target molecule. In some embodiments, the antibody is labelled (e.g., with fluorescent labels such as fluorescein), enzymatic detection labels (such as horse radish peroxidase), and metal labels (such as gold). This method has the fifrther advantage of immunologically confirming the identity of the protein binding to the target molecule.

In some embodiments, kits are provided for performing the process described herein. The kits of the present invention may comprise individual ligands specific for individual soluble CD and/or soluble MHC Class I antigens and/or cytokines and/or chemokines described herein, plus buffers, and so on.

The methods described herein are not restricted to the analysis of whole blood, serum and plasma; indeed sCD molecules, soluble MHC Class I antigens, cytokines and chemokines are known to be present in many other body fluids, as described above. Furthermore, the methods described herein are not restricted to use in humans, and indeed such a method may prove to be of immense use in veterinary applications, having immense use in non humans, including, but not limited to felines, canines, equine, avian, murine, rats, rodents, hamsters, rabbits, tigers, elephants, bears, nonhuman primates.

By "confusion table" it is meant a table that associates common errors in the noisy process with probabilities that those errors occurred.

One embodiment described herein is a sCD fingerprint comprising the levels of plurality of sCDs where the sCD fingerprint represents one or more disease states. Also described herein is a method of generating a sCD fingerprint of one or more disease state/s comprising the step of measuring the levels in parallel of a plurality of shed or secreted sCDs from one or more individuals and collating the data. Patterns may then be discerned from this collated data using mathematical algorithms such as neural networks. The sCD fingerprint can be associated with a disease state including but not limited to an: infectious, neoplastic, cardiovascular, immunological, autoimmune, metabolic, degenerative, diet-related, psychological, psychiatric, iatrogenic, inflammatory, drug or toxin related, traumatic and endocrine disease. As such, the disease state can be any one or more selected from the group consisting of the following: infection, multiple myeloma (Bence Jones proteinuria), chronic myeloid leukemia, acute myeloid leukemia (AML), other acute leukemias and myelodysplastic syndromes, colorectal cancer, chronic renal failure, crohn's disease, diabetic nephropathy, cardiovascular pathology, infection, Liver damage, Lymphoma, Macrocytic anemia, Prostate cancer, oligoclonal banding and pulmonary embolism, deep vein thrombosis and appendicitis. An exemplary sCD fingerprint can include any one, two, three, four, or more of the following sCD antigens: sCD14, sCD25, sCD30, sCD31, sCD44, sCD50, sCD54, sCD62E, sCD62L, sCD86, sCD95, sCD106, sCD116, sCD117, sCD124, sCD130, sCD138, sCD141, sCD40L, sCD8, sCD23, sCD30, sCD40 and their homologues present in other mammalian or non-mammalian species and can in addition include other soluble CD antigens and other soluble antigens including soluble MHC Class I antigens, cytokines or chemokines. The sCD levels can be measured using any one or more of the methods selected from the group consisting of the following: multiplexed particle flow cytometry, chip-based monoclonal antibody technology, chips comprising engineered antibodies, and/or non-protein agents which bind to one or more sCDs. This list of technologies is not though exhaustive and the levels of sCD molecules, cytokines, chemokines and soluble MHC class I molecules can, in principle, be measured by any technology capable of documenting the levels of these molecules in body fluids to a sufficiently quantitative extent. The patterns fo these molecules as such are in this sense technology independent, with the technology simply being the process by which the patterns may in principle be defined. Representative antibodies with specificity to soluble isoforms of CD antigens are listed in Table 46, and representative molecules capable of detecting the representative antibodies are listed in Table 47.

Described herein are methods for predicting the presence of one or more disease states in an individual comprising the step of comparing a sCD fingerprint/s, comprising the levels of a plurality of sCDs generated from that individual with one or more reference sCD fingerprint/s. Disclosed herein is a method for detecting the presence of one or more disease states in an individual comprising the step of comparing a sCD fingerprint/s comprising the levels of a plurality of sCDs generated from that individual with one or more reference sCD fingerprint/s. Disclosed herein is a method for detecting the extent of one or more disease states in an individual comprising the step of comparing sCD fingerprint/s, comprising the levels of a plurality of sCDs, generated from that individual with one or more reference sCD fingerprint/s. Disclosed herein is a method for assessing the progression of a disease state in an individual comprising the step of comparing the sCD fingerprint of an individual, comprising the levels of a plurality of sCDs, at two or more periods during the course of the disease. Disclosed herein is a method for assessing the effect of one or more agent/s on one or more disease states in an individual comprising the step of comparing a sCD fingerprint of an individual, comprising the levels of a plurality of sCDs, at two or more different time periods. Disclosed herein is a method for sub-categorizing a sCD fingerprint profile, comprising the levels of a plurality of sCDs, comprising the steps of identifying within one disease category one or more group/s of sCDs wherein each group of sCDs exhibits common characteristics distinguishing it from any other group within that disease category. Disclosed herein is a method of creating a sCD database comprising pathological and/or normal sCD fingerprint patterns, in which a sCD fingerprint comprises the levels of plurality of sCDs, comprising the step of measuring the levels in parallel a plurality of sCDs from one or more individuals and collating the data.

WORKING EXAMPLES

Described herein are working examples exemplifying the products and methods described herein for the diagnosis, diagnostic sub-classification, prognostic stratification and monitoring of diseases and disorders, as exemplified by the human disease of leukemia. Though leukemia is the disease exemplified by these working examples, these methods of these working examples can be applied to other diseases, disorders and conditions. These working examples encompass measuring the expression levels of sCD molecules produced by shedding, secretion or other molecular mechanisms in human body fluid samples, both diseased and healthy normal controls, preferably using a chip- or bead-based technology, but in no way being restricted to these technologies. Surprisingly, we have successfully demonstrated that the detected antigen expression levels can be used to predict leukemia with a considerably high accuracy of 79%-89%. We carefully examined the issue of alternative normalization strategies, which lead to a comparable and meaningful data basis for classification.

By varying the analysis method, considering only acute myeloid leukaemia (AML) samples, normal samples (norm-Mix), and all other samples as labels, we demonstrated the high predictive value of sCD antigen expression profiles/fingerprints for one subset of the leukemia families. The discrimination of AML (acute myeloid leukemia) versus other leukemias, e.g., CML (chronic myeloid leukemia), NHL (non-Hodgkin's lymphoma), and CLL (chronic lymphocytic leukemia), and healthy control samples yielded especially promising results using the five sCD antigen probes employed in this investigation.

In order to evaluate the predictive power of using multiple sCD antigen probes as opposed to a single sCD antigen probe, we tested the predictive power using only one soluble CD antigen, sCD117, versus using all 5 sCD antigens. We demonstrated that although this single sCD antigen has a significant predictive performance on its own, the addition of the other sCD antigens increases the discriminative power in a statistically significant manner, despite the low number of samples. This suggests that the predictive performance could be increased even further by adding in additional sCD antigens. Indeed the utilisation of multiple sCD antigens in excess of the 5 employed here is predicted by these experiments to increase the sensitivity and specificity of this method and thus the ability of such a test to discriminate between different leukaemia subclasses and different subtypes of same subclass and indeed between different disease states, very significantly. As such the use of multiple sCD antigens may be used for monitoring the response to therapeutic interventions in those individuals with leukaemia, for diagnosis and classification of leukaemia subtypes, as well as for the prognostic stratification of specific cases of leukaemia and for the determination of minimal residual disease (MRD).

The Iterative Weighted Least. Squares (IWLS) mean extended data method in its current form is expected to be of considerable use in diagnosing and prognosing human leukemias, and in particular acute myeloid leukaemia (AML) for which there is a significant unmet medical need for diagnostic and prognostic biomarkers, as well as in identifying biomarkers that can be used to monitor response to therapy, to act a surrogate end-points in clinical trials, to detect early remission, to detect attainment of full remission, and to detect early relapse and to predict drug sensitivity. The utilisation of sCD and/or soluble MHC Class I antigen profiling/fingerprinting in AML and other human leukemias is expected to be of considerable clinical utility both in primary and tertiary settings and it is expected that the use of sCD profiling/fingerprinting in therapeutic contexts will help facilitate the detection of minimal residual disease following therapy and also the monitoring of individual response to therapeutic interventions and the reoccurrence of disease. The identification of poor prognostic groups through sCD antigen pattern based prognostic stratification using this technology should enable pre-selection of those individuals requiring more aggressive therapeutic interventions and those who need more aggressive and frequent monitoring of therapeutic response. The method may also help predict those individuals that are likely to be intolerant to a particular therapeutic intervention and those individuals that are likely or be responders, non-responders, or rapid responders to a particular therapeutic intervention. It is predicted that the individual sCD antigens compromising the pattern/profile/fingerprint may themselves also be potential targets for therapeutic intervention, either alone or in combination through multiple simultaneous targeting and as such this method also provides a means of identifying sCD antigens and their cell surface counterparts that might in principle be targeted by therapeutic interventions.

The levels of five sCD antigens were assayed in plasma taken from healthy (normal) controls and from patients with the following leukemias: AML (acute myeloid leukemia), CML (chronic myeloid leukemia), NHL (non-Hodgkin's lymphoma), and CLL (chronic lymphocytic leukemia). For this purpose five soluble CD antigens: sCD14, sCD30, sCD54, sCD117, sCD130 were measured using a single-blinded protocol in plasma taken from both patients and healthy controls using matched antibody pairs which comprised either two monoclonals or one monoclonal and a polyclonal, that were either attached to Luminex microbeads, or arrayed onto a chip using the chip-based methodology and the chip-based proteomic protein microarray technology of GenTel Biosciences Inc.

The purpose of the three different experiments described below was to determine if patterns of 5 or more sCD antigens measured in plasma (or in whole blood or in principle in serum or in any other body fluids outlined already in detail above such as: pleural fluid, urine, ascitic fluid, saliva, uveal fluid and so on) can be used to generate sCD protein expression signatures that are characteristic of cancer as opposed to normals, or that are characteristic of a particular disease state, namely in this instance of one particular leukemia type vs. other leukemia types and healthy normal controls. Our finding was that patterns of 5 or more sCD antigens are significant indicators of a specific disease state whether it is cancer vs. healthy controls or cancer sub-type vs. other cancer sub-types than individual sCD antigens on their own. The utility of a test of this sort is determined by documenting its sensitivity and specificity for determining the target disease.

Working Example 1

Experimental Setup: GenTel Biosciences Inc Chip Platform
Composition of the Samples:

The dataset for each of the three experiments was acquired via antibody array chip experiments using the following 47 samples:

TABLE 1

Composition of the sample classes

| Sample Type | Number of Samples |
|---|---|
| AML | 9 |
| CML | 12 |
| CLL | 12 |
| NHL | 6 |
| NormMix (normal controls) | 8 |
| TOTAL | 47 |

Chip Layout

Soluble CD antigens in the 47 plasma samples were measured using the chip-based technology of GenTel Biosciences Inc. Assays for this investigation were performed on a standard GenTel Biosciences PATH slide. The PATH slide consisted of a standard sized glass substrate containing an adhesion layer onto which a thin coat of nitrocellulose was applied.

The layout of the chip with a total size of 25×75×1 mm is illustrated in FIG. 1. Each well is 9×9 mm in dimension with a total number of 16 wells per chip. Each sample was replicated onto two wells (left/right) and within each well, each probe was replicated 6 times leading to a total of 12 replicates per sample and antigen probe.

Figure 2:
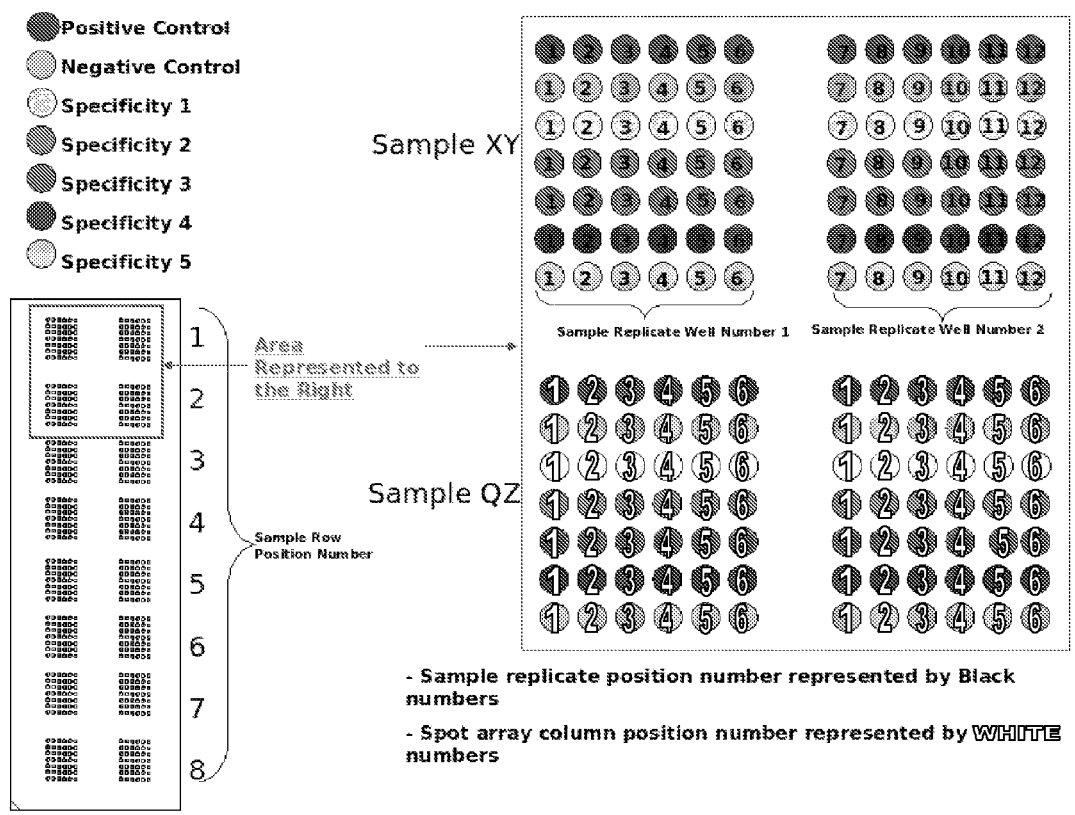
FIG. 2. Illustrates one embodiment of a probe layout for two of the eight samples captured by a single chip. Five sCD antigen probes, a positive control and an additional negative normal probe were assessed, leading to a total number of 84 measured probes per sample distributed over two wells.
Figure 3:
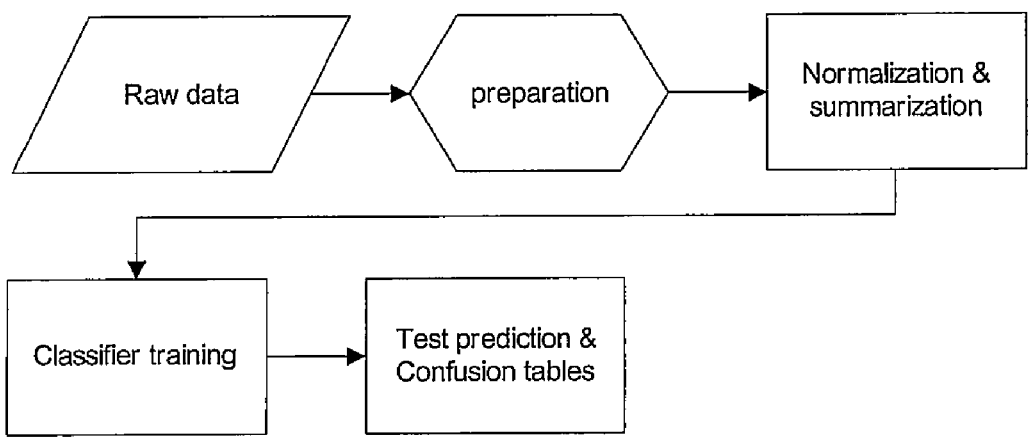
FIG. 3. Flow chart of the full data analysis procedure.
Figure 4:
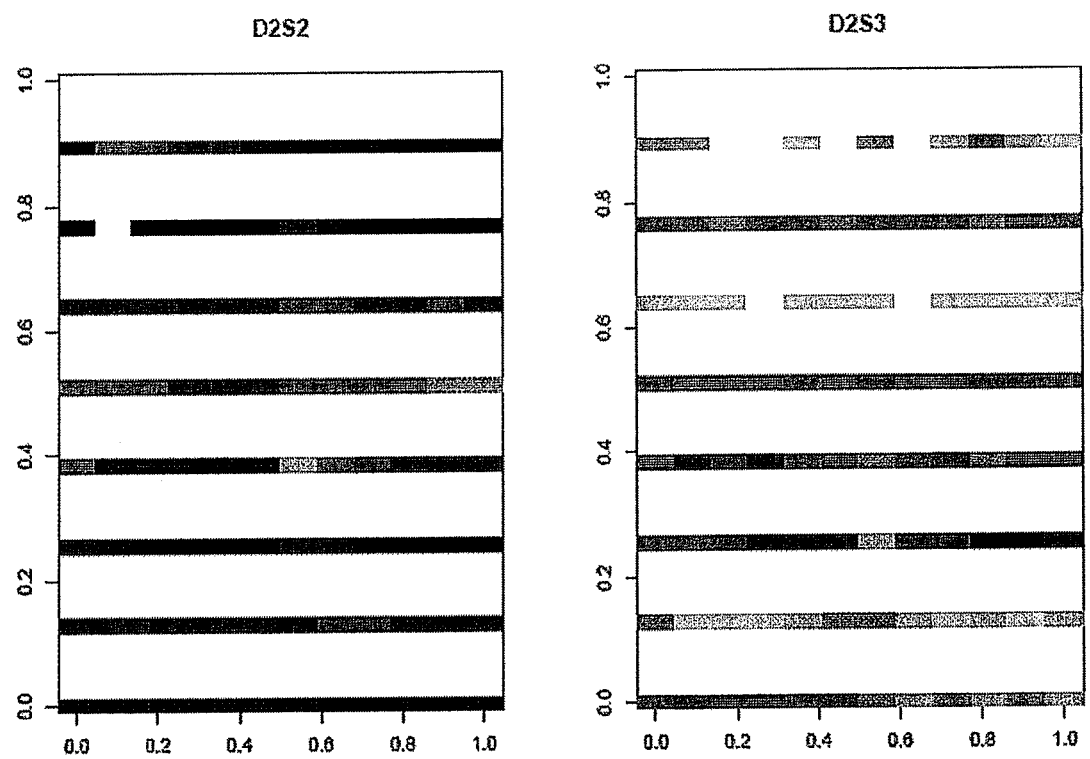
FIG. 4: Spatial distribution of Neg. Probe relative fluorescence units (RFUs) for two slides measured on the second day. The expression level (log 10) is coded where increase in brightness corresponds to a stronger signal.
Figure 5:
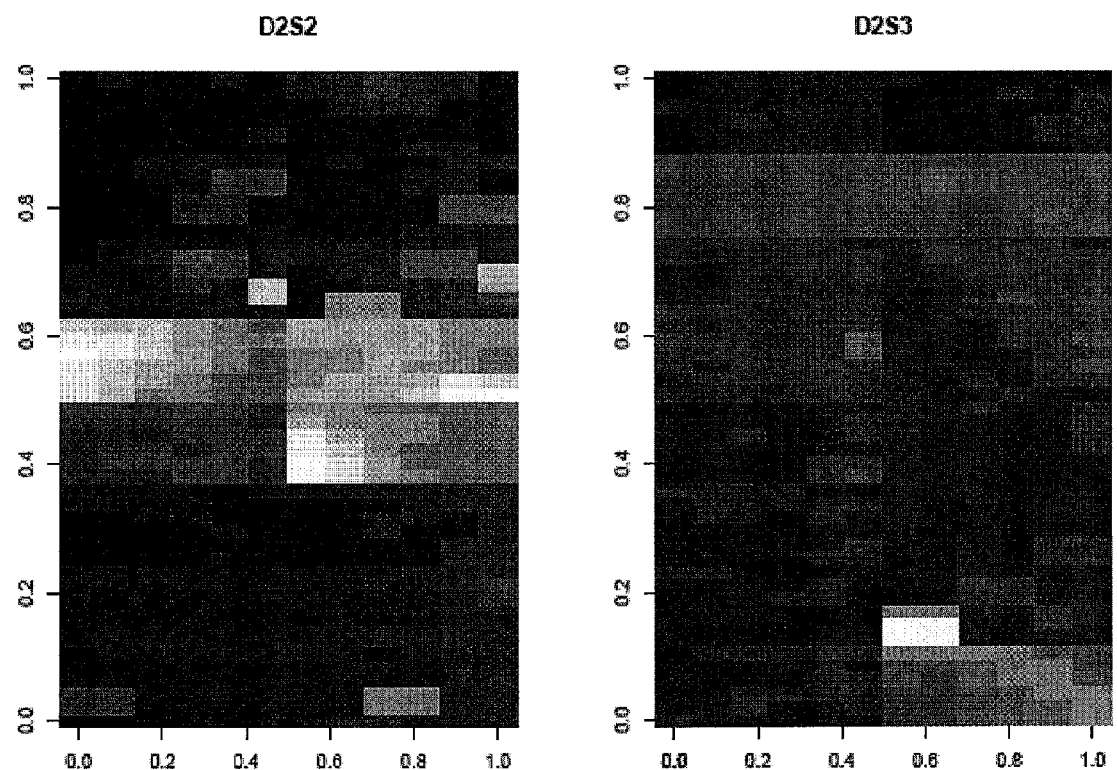
FIG. 5: Spatial distribution of Probe background RFUs in log 10 for two slides measured on the second day. The expression level (log 10) is coded where an increase in brightness corresponds to a stronger signal.

FIG. 2 illustrates five sCD antigen probes; a positive control and an additional negative normal probe were assessed, leading to a total number of 84 measured probes per sample distributed over two wells. Arraying of the capture antibodies was performed using a Gesim NanoPlotter 2.0/E printer. This is a piezo non-contact instrument with the printing parameters as follows (see Table 2).

TABLE 2

| Parameters for the printing process of the slides. | |
|---|---|
| Antibody Printing Concentration | 0.5 mg/ml |
| Printing Buffer | 1xGenTel Print Buffer |
| Printing Temperature | Ambient |
| Printing Humidity | 60% |
| Batch Size | ~30 slides |
| Spot Diameter | ~220 µm |
| Spot Pitch | ~350 µm |

The fluorescent signals on the slides were scanned using a confocal laser scanner (Tecan LS 200 Reloaded). Scanning was performed applying a single-scanning protocol with a scanning resolution of 10 µm/pixel. The resulting images were analysed with ArrayVision 8.0, performing spot finding, as well as measurement and background estimation. Background relative fluorescence units (RFUs) were determined from four measured background spots around each single probe. Most of these implementation details are standard, but it is important to note that probes were allocated to their address on the chip using a regular grid rather than a randomized procedure.

Experimental Procedure Outline:

Experiments were conducted over two days. On both days one set of standard curves was constructed. The experimental protocol included the following steps: block slides, assemble the separator apparatus, antigen addition, incubate, wash, detector antibody addition, incubate, wash, apply detection reagent, incubate, wash, rinse, dry and scan.

Data Analysis:

The final goal of the data analysis was to create a predictor engine that is able to predict the sample class of a new, unseen sample, namely disease type or healthy control based upon the training data of labelled samples. Intuitively this is achieved by learning patterns of expression levels for all measured antigens, which potentially could look very different depending on the sample class.

The raw measured expression levels from the chip experiments are first consolidated into one consistent data table. Normalization thereafter ensures that the measured values are comparable across different experiments. Normalized data with labels is then used to train a predictor for the disease classes whose performance is evaluated by means of cross validation.

Data Preparation:

The raw measured expression level data provided by Gen-Tel Biosciences were first consolidated into a verified consistent data table (preparation), partially by editing the data manually and partially using automated custom methods for this project. The full annotated raw data consisted of the expression levels for each probe (RFU values), individual background RFUs for each spot and coordinate information of the corresponding spots on the chip (fullrecords.dat).

Normalization, Summarization & Standard Curves:

Normalization is a crucial pre-processing step to make the data originating from multiple experiments comparable. In non-automated experimental designs, as implemented in this pilot study, it is essential to remove systematic effects, such as operator effects, day or time drifts or spatial correlations in the dataset. Because of the significance of such effects, several alternative normalization strategies were evaluated by means of explorative data analysis. Effects of normalization were studied, as were their ability to remove spurious correlations and their net-influence on the classification performance. The different normalization methods employed were briefly:

1. Use of Background RFU measurements as a means of removing spatial variation of measurement background intensity on the chip. Background subtraction on a linear scale or on log scale.
2. Use of Negative Probe measurements as a means of removing spatial variation of measurement background intensity on the chip. Background subtraction on linear scale or on log scale.
3. Use of standard curves for intensity range normalization.

Background RFU Versus Negative Probe Measurement:

We investigated normalization characteristics using either the background RFUs, measured for each individual probe, or the negative probes measurements per well to subtract a background signal. Analyzing the correlation of the background RFU values and the Negative Probe expressions revealed the very low correlation of 27%. A visualisation of the signal from the negative normal probes and of the background RFUs from all probes on the chip illustrates their systematic differences.

This indicates that the negative probes not only capture spatial effects but also additional effects such as well location, and operator or day-specific influences. Normalizing the Negative Probes themselves by subtracting their background RFUs amplified the differences in Negative Probe measurements on the two days (0.51 versus 0.27) and increased interquartile range (IQR) (0.32 versus 0.11) as well as the residual error in the ANOA model fitted to the background.

The observation that for a fraction of 2% of the measurements the background RFU was actually higher than the Negative Probe expression value supports the conclusion that the background RFUs are less meaningful then Negative Probes. This suggests that Negative Probes are a better choice for the removal of measurement bias than the background RFUs.

The reported correlations were analysed via an ANOVA model, which revealed significant day and left/right (well location) effects, while spatial effects (x/y location of the spot) were of minor significance. Using an iterative weighted least squares (IWLS) mean (a robust mean estimator) of the Negative Probes, per well, as a background-model, removes the strong well bias and the day influence in the ANOVA model. Furthermore, all measurements showed intensities consistently higher than the background estimated via the Negative Probe well mean. Hence due to its efficiency in removing well and day effects, IWLS mean extended data is the preferred normalization method (fullrecords-minusNegByWell.dat). Positive probes were all saturated and therefore had to be discarded.

Figure 6:
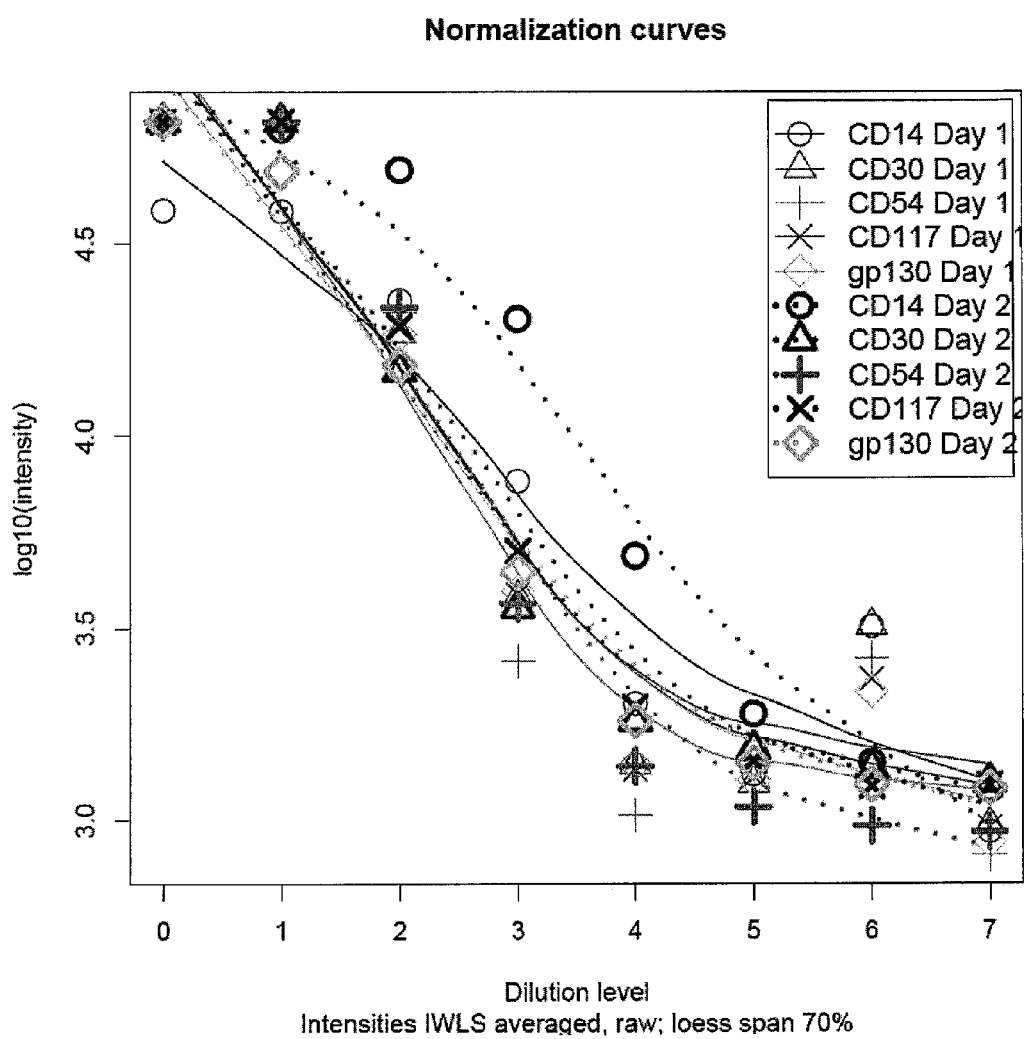
FIG. 6: Raw Standard Curves for all five antigens on both days. Curves plotted using a LOWESS smoother (degree 1, span 0.5).
Figure 7:
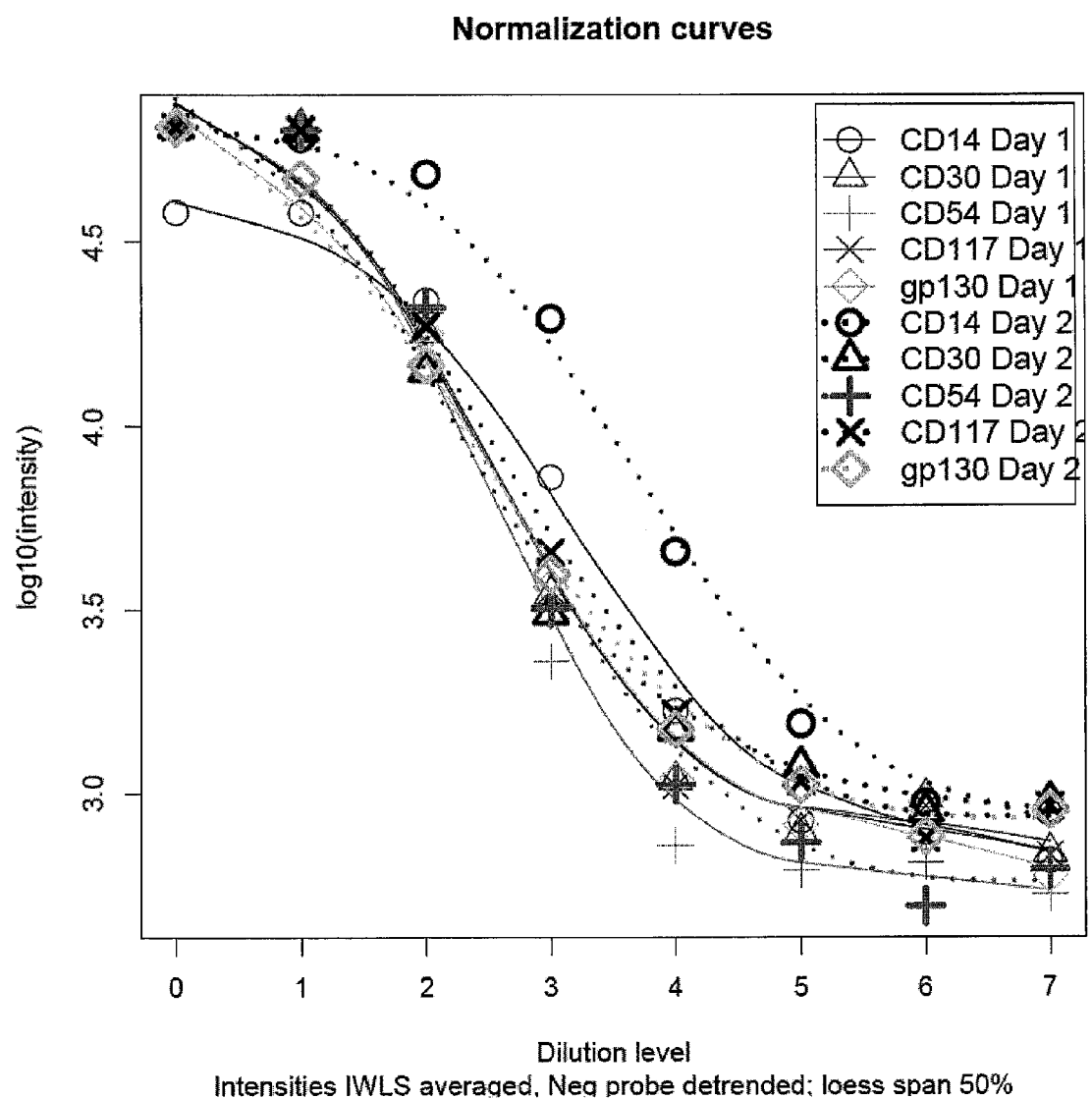
FIG. 7: Iterative weighted least squares (IWLS) mean extended Standard Curves for all five antigens on both days. Curves plotted using a LOWESS smoother (degree 1, span 0.5).
Figure 8:
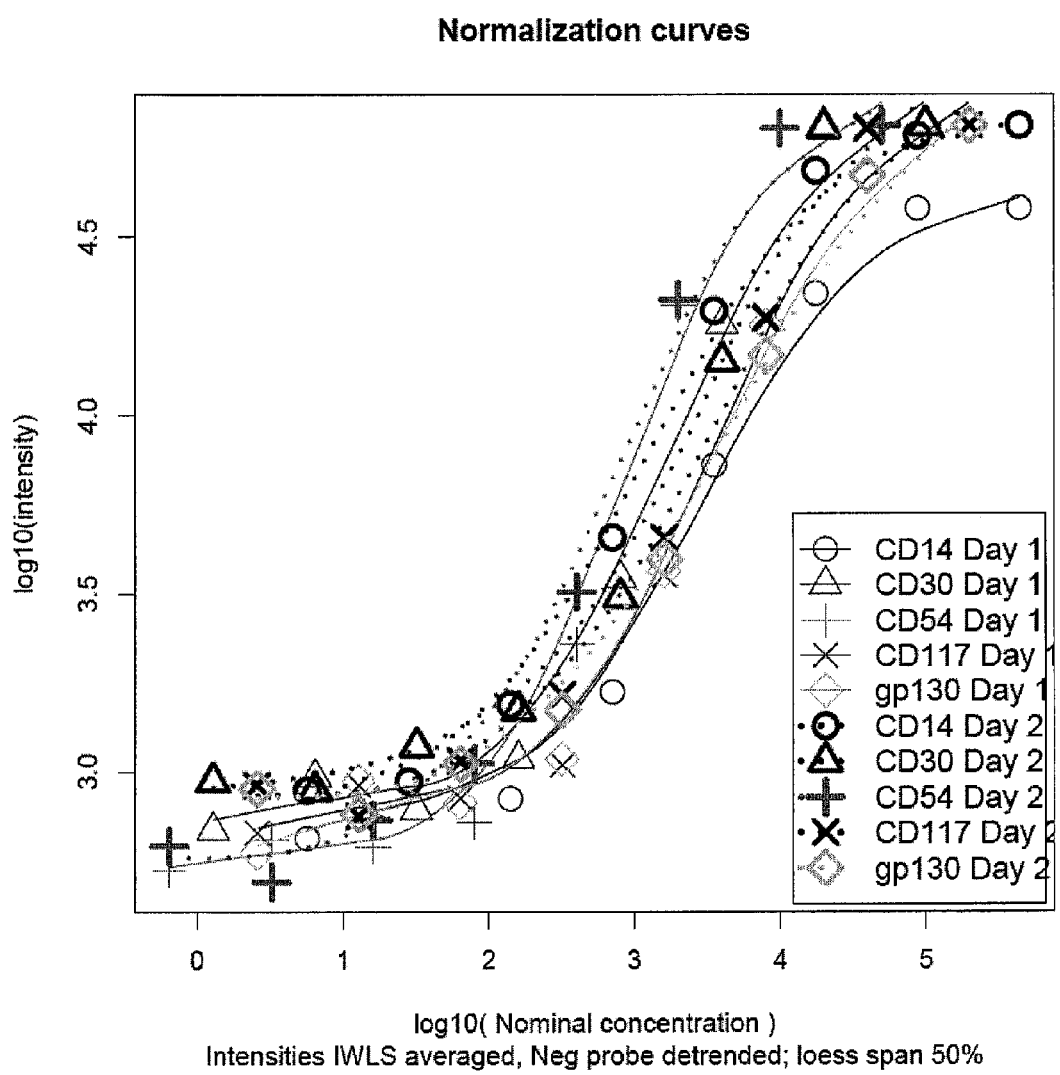
FIG. 8: Iterative weighted least squares (IWLS) mean extended Standard Curves converted to concentration levels.

Standard Curves:

For both days, standard curves were recorded (FIG. 6). Negative probe corrected curves, as described above, are considerably improved (FIG. 7). From these curves, intensity readings can directly be converted to concentrations, although only in the intensity range covered by the standard curve (FIG. 8). For some measurements, as for a larger number of the sCD30 measurements where the intensity value was lower than a zero concentration, the measured value was outside the range of the standard curve and hence had to be truncated leading to a loss of information. The effect of this can be observed by mean of a reduced correlation between identical samples run on two days (98.5% versus 91.1%) and a significantly lower prediction accuracy compared to using the raw normalized intensity values (confusion tables for classifiers, Tables 9 and 10). This suggests a considerable background drift of the setup during the experiments on any one day. If concentration levels and hence standard curves were required they would need to be measured more frequently in order to reflect the actual measurement conditions more accurately. Most likely this is less of an issue for a more automated experimental setup, which is less vulnerable to drifts.

Summarization:

In order to provide a strong and consistent signal for the classifier it is essential to reduce the dimensionality of the normalized data and thereby gain signal. Each of the five antigen probes is 12 fold replicated on the chip and consequently a standard option would be to take the arithmetic mean for all replicates of one probe. Since it is to be expected that the noise distribution is rather heavy tailed, a more robust mean estimator such as IWLS may be more appropriate. Especially in case of large number of replicates, for instance compared to a typical microarray experiments, robust estimators become feasible.

The following summarization methods were evaluated for each of the classification experiments:

1. rawByWell.mean.dat: untouched raw data without background subtraction, standard mean was used to summarise the replicates of any one probe.
2. rawByWell.robust.dat: untouched raw data without background subtraction, IWLS average by well to summarise the replicates of any one probe.
3. minusNegByWell.robust.dat: IWLS mean normalized data (background from Negative probes), IWLS average by well to summarise the replicates of any one probe.
4. minusNegByWellNormalizedWithinCurveRange.robust.dat: as above but projected through day-specific experimental standard-calibration curves. Note: values that were outside the calibration range were truncated.

For each of these methods the probes from each well were background corrected by subtracting the well-local background value on the original intensity scale (linear).

The data was then put on a log 10 scale and summarized by means of averaging on this log scale. The replicates of the same sample in the two wells (left/right) were treated as separate samples in the analysis. This seems to double the amount of samples used for the training but of course we expect very similar expression levels in both wells. Cross normalization over wells is prone to distortions and not necessary since the copy number in any single well is sufficiently high.

Concluding the discussion about the different normalization options we note that minusNegByWell.robust is the strongest candidate for summarization. This method combines the successful removal of day and well effects (background subtraction based on Negative Probes) with a robust mean estimator (IWLS) of the probe replicates.

Classification

The normalized and summarized data forms the basis for the training of a classifier. The patterns that potentially may be picked up by the classifiers can be visualised by plotting this five dimensional input data.

Figure 9:
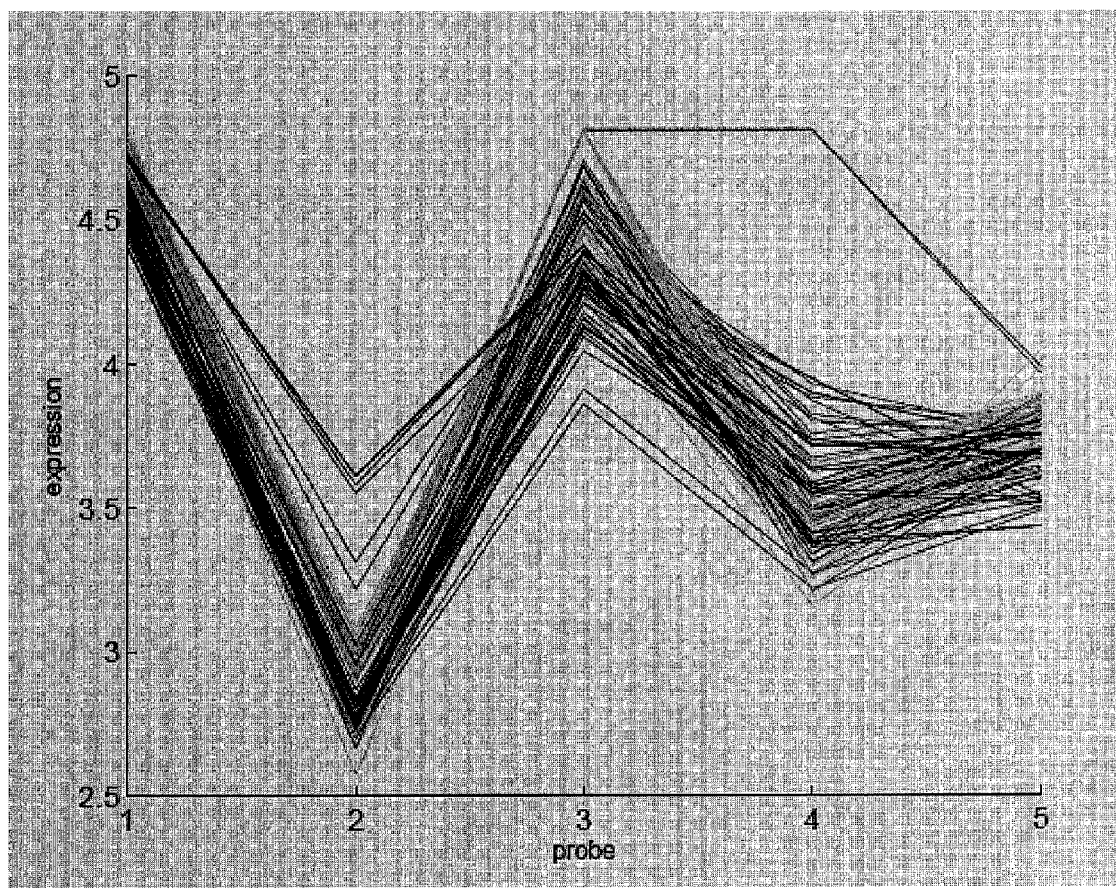
FIG. 9: Displays minusNegByWell.robust classifier input data. Antigens (probe) from 1 to 5: sCD14, s CD30, sCD54, sCD117, sgp130. Colours code the five sample classes (AML, CML, CLL, NHL, and NormMix).
Figure 10:
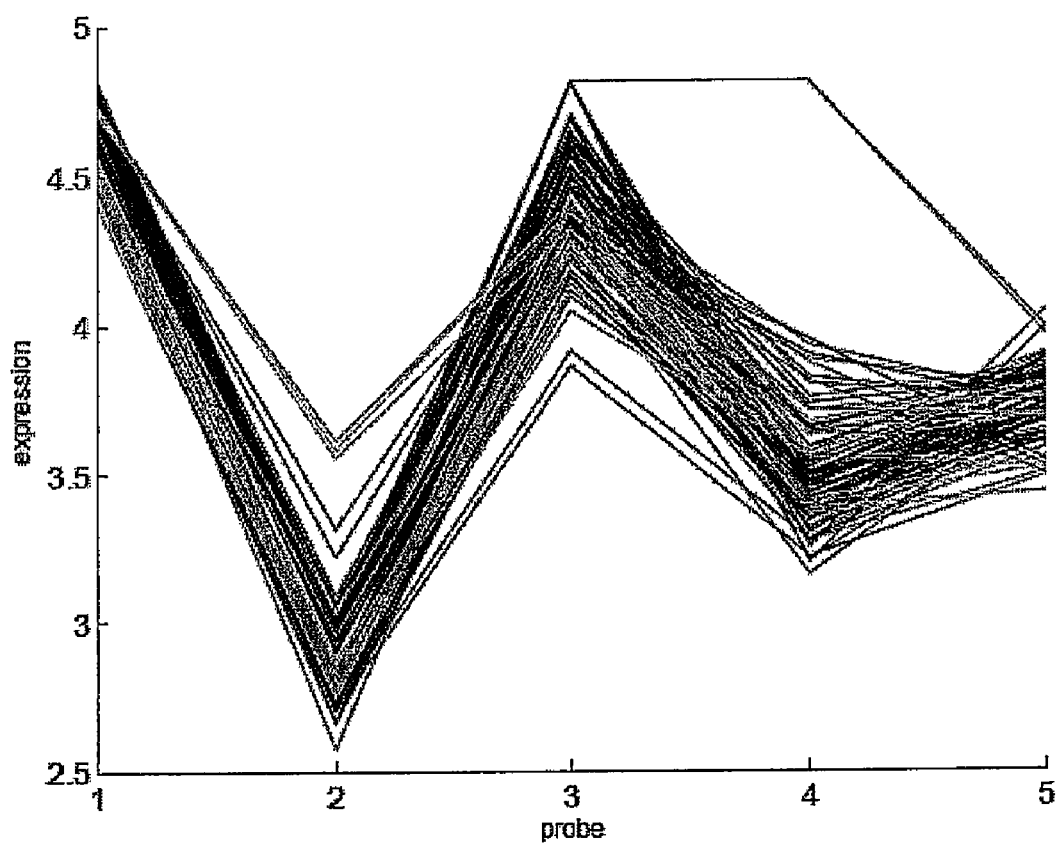
FIG. 10: Displays minusNegByWell.robust classifier input data. Antigens (probe) from 1 to 5: sCD14, sCD30, sCD 54, sCD117, sCD130.

FIG. 9 illustrates the summarized intensity values for the antigens for all 47 samples using minusNegByWell.robust summarization. It is visually apparent that probe number 4 (sCD117) separates many of the different classes quite well. A more formal evaluation comparing classification performance using single probes or multiple probes will be given later. FIG. 10 is identical but only visualizes disease vs. NormMix samples, illustrating that these two groups show very strong patterns.

We used this data as the input for classification, comparing two alternative classifiers—standard k-nearest-neighbours classifiers (kNN) and the Multi Layer Perception (MLP), trained with the evidence framework as introduced by David MacKay et al. (1995).

Classification of all Sample Types:

The classification performance was evaluated for the four normalization/summarization alternatives stated above and for both classifiers.

For all classification experiments we give confusion tables summarizing the result of leave-one-out cross validation. It is stated how often a specific sample type (rows) was predicted as any one of the five classes (columns). An ideal predictor would hence yield a matrix with non-zero entries only on the diagonal. Confusion tables can easily be converted to specificity and sensitivity characterisation of the classification performance for each class. We state those results for the best of the normalization/classifier result respectively.

For the first experiment using all probes predicting all five classes, the various summarization methods and classifiers performed very similarly, with the notable exception of experiments in which the classifier minusNegByWellNormalizedWithinCurveRange.robust was used for summarization. As mentioned earlier, this was expected due to the truncation of out of range intensity values. The remaining experiments yielded consistently good predicted performance of 57-64%, which is 2-3 fold as good as random guessing. These differences of 6% are not significant for the sample number used in this experiment.

The confusion tables and estimates for the generalization performance for the classifiers (kNN and MLP), separately for all 4 summarization methods, are listed Tables 3-10.

A summarizing table stating specificity and sensitivity for each of the tests using the MLP classifier with rawByWell.robust summarization is given in Table 11.

Notably the specificity is generally high for all 5 classes. Sensitivity of the classification is especially encouraging for AML samples and normMix/disease, i.e. general classification of disease versus healthy (normal) samples.

Tables 3 and 4: Confusion Tables and Generalization Performance for rawByWell.mean Summarization for kNN and MLP Classifier

TABLE 3

Data: rawByWell.mean, Confusion Table, MLP, Evidence Framework, Generalization Accuracy: 0.64

| | | Predicted | | | | |
|---|---|---|---|---|---|---|
| | | AML | CML | CLL | NHL | normMix |
| TRUE | AML | 16.00 | 0.00 | 2.00 | 0.00 | 0.00 |
| | CML | 0.00 | 14.00 | 6.00 | 2.00 | 2.00 |
| | CLL | 0.00 | 8.00 | 9.00 | 2.00 | 5.00 |
| | NHL | 0.00 | 3.00 | 3.00 | 6.00 | 0.00 |
| | normMix | 1.00 | 0.00 | 0.00 | 0.00 | 15.00 |

TABLE 4

Data: mean, rawByWell.mean, Confusion Table, k Nearest Neighbor, Generalization Accuracy: 0.60

| | | Predicted | | | | |
|---|---|---|---|---|---|---|
| | | AML | CML | CLL | NHL | normMix |
| TRUE | AML | 12.00 | 3.00 | 1.00 | 0.00 | 2.00 |
| | CML | 0.00 | 17.00 | 5.00 | 2.00 | 0.00 |

TABLE 4-continued

Data: mean, rawByWell.mean, Confusion Table, k Nearest Neighbor, Generalization Accuracy: 0.60

|  | | Predicted | | | | |
|---|---|---|---|---|---|---|
|  | | AML | CML | CLL | NHL | normMix |
|  | CLL | 0.00 | 10.00 | 11.00 | 1.00 | 2.00 |
|  | NHL | 0.00 | 4.00 | 2.00 | 6.00 | 0.00 |
|  | normMix | 0.00 | 2.00 | 4.00 | 0.00 | 10.00 |

Tables 5 and 6: Confusion Tables and Generalization Performance for rawByWell.robust Summarization for kNN and MLP Classifier

TABLE 5

Data: rawByWell.robust, Confusion Table, MLP, Evidence Framework, Generalization Accuracy: 0.61

|  | | Predicted | | | | |
|---|---|---|---|---|---|---|
|  | | AML | CML | CLL | NHL | normMix |
| TRUE | AML | 15.00 | 0.00 | 2.00 | 0.00 | 1.00 |
|  | CML | 1.00 | 13.00 | 7.00 | 2.00 | 1.00 |
|  | CLL | 0.00 | 8.00 | 9.00 | 3.00 | 4.00 |
|  | NHL | 0.00 | 4.00 | 2.00 | 6.00 | 0.00 |
|  | normMix | 0.00 | 2.00 | 0.00 | 0.00 | 14.00 |

TABLE 6

Data: rawByWell.robust, Confusion Table, k Nearest Neighbor, Generalization Accuracy: 0.57

|  | | Predicted | | | | |
|---|---|---|---|---|---|---|
|  | | AML | CML | CLL | NHL | normMix |
| TRUE | AML | 12.00 | 4.00 | 1.00 | 0.00 | 1.00 |
|  | CML | 0.00 | 16.00 | 6.00 | 2.00 | 0.00 |
|  | CLL | 0.00 | 10.00 | 10.00 | 2.00 | 2.00 |
|  | NHL | 0.00 | 3.00 | 3.00 | 6.00 | 0.00 |
|  | normMix | 0.00 | 3.00 | 3.00 | 0.00 | 10.00 |

Tables 7 and 8: Confusion Tables and Generalization Performance for minusNegByWell.robust Summarization for kNN and MLP Classifier

TABLE 7

Data: minusNegByWell.Robust, Confusion Table, MLP, Evidence Framework, Generalization Accuracy: 0.61

|  | | Predicted | | | | |
|---|---|---|---|---|---|---|
|  | | AML | CML | CLL | NHL | normMix |
| TRUE | AML | 15.00 | 0.00 | 2.00 | 0.00 | 1.00 |
|  | CML | 1.00 | 12.00 | 8.00 | 2.00 | 1.00 |
|  | CLL | 0.00 | 9.00 | 10.00 | 1.00 | 4.00 |
|  | NHL | 0.00 | 4.00 | 2.00 | 6.00 | 0.00 |
|  | normMix | 2.00 | 0.00 | 0.00 | 0.00 | 14.00 |

TABLE 8

Data: minusNegByWell.Robust, Confusion Table, k Nearest Neighbor, Generalization Accuracy: 0.64

|  | | Predicted | | | | |
|---|---|---|---|---|---|---|
|  | | AML | CML | CLL | NHL | normMix |
| TRUE | AML | 14.00 | 3.00 | 1.00 | 0.00 | 0.00 |
|  | CML | 2.00 | 14.00 | 7.00 | 1.00 | 0.00 |
|  | CLL | 0.00 | 4.00 | 16.00 | 2.00 | 2.00 |
|  | NHL | 0.00 | 4.00 | 2.00 | 6.00 | 0.00 |
|  | normMix | 0.00 | 1.00 | 5.00 | 0.00 | 10.00 |

Tables 9 and 10: Confusion Tables and Generalization Performance for minusNegByWellNormalizedWithinCurveRange.robust Summarization for kNN and MLP Classifier

TABLE 9

Data: minusNegByWellNormalizedWithinCurveRange.robust, Confusion Table, MLP, Evidence Framework, Generalization Accuracy: 0.45

|  | | Predicted | | | | |
|---|---|---|---|---|---|---|
|  | | AML | CML | CLL | NHL | normMix |
| TRUE | AML | 11.00 | 2.00 | 2.00 | 0.00 | 3.00 |
|  | CML | 0.00 | 8.00 | 11.00 | 3.00 | 2.00 |
|  | CLL | 0.00 | 13.00 | 6.00 | 2.00 | 3.00 |
|  | NHL | 0.00 | 5.00 | 2.00 | 5.00 | 0.00 |
|  | normMix | 3.00 | 1.00 | 0.00 | 0.00 | 12.00 |

TABLE 10

Data: minusNegByWellNormalizedWithinCurveRange.robust, Confusion Table, k Nearest Neighbor, Generalization Accuracy: 0.50

|  | | Predicted | | | | |
|---|---|---|---|---|---|---|
|  | | AML | CML | CLL | NHL | normMix |
| TRUE | AML | 11.00 | 4.00 | 0.00 | 0.00 | 3.00 |
|  | CML | 0.00 | 19.00 | 3.00 | 1.00 | 1.00 |
|  | CLL | 0.00 | 17.00 | 4.00 | 0.00 | 3.00 |
|  | NHL | 0.00 | 6.00 | 4.00 | 2.00 | 0.00 |
|  | normMix | 0.00 | 1.00 | 4.00 | 0.00 | 11.00 |

TABLE 11

Sensitivities/Specificities for minusNegByWell.robust summarization with MLP classifier: overall specifty for healthy versus disease at the end.

| Sample type | Specificity | Sensitivity |
|---|---|---|
| AML | 96% | 83% |
| CML | 81% | 50% |
| CLL | 83% | 42% |
| NHL | 96% | 50% |
| Disease | 88% | 92% |

Working Example 2

Classifier Performance AML/Other/normMix:

In a second experiment we evaluated the predictive performance distinguishing only three sample classes: AML, norm-Mix and all of the remainder. Again all four summarization methods for two classifiers were compared with a very similar outcome as before. Differences in predictive accuracy of about 6% have no significance. The classification performance varied between 79%-89%, (which is about 140% as good as you would get from guessing (64%)).

Confusion tables and estimates for the generalization performance for all individual classifier/normalization pairings are listed in Tables 12-19. A conversion to sensitivity/specificity of the MLP classifier with minusNegByWell summarization can be found in Table 20.

Training the classifier only on three classes yields a very similar specificity/sensitivity than for the five classes experiment. Differences compared to the first experiment are not significant.

Sensitivity and Specificity of AML versus healthy normals is very similar to the 5-class experiment.

We can conclude that AML can be well discriminated from the other classes based on the five sCD antigens with a considerably high precision.

Tables 12 and 13: Confusion Tables and Generalization Performance for rawByWell.mean Summarization for kNN and MLP Classifier Discriminating Between 3 Classes

TABLE 12

Data: rawByWell.mean, Confusion Table, k Nearest Neighbor, Generalization Accuracy: 0.82

|      |         | Predicted |       |         |
|------|---------|-----------|-------|---------|
|      |         | AML       | CML   | normMix |
| TRUE | AML     | 10.00     | 7.00  | 1.00    |
|      | other   | 0.00      | 60.00 | 0.00    |
|      | normMix | 0.00      | 9.00  | 10.00   |

TABLE 13

Data: rawByWell.mean, Confusion Table, MLP, Evidence Framework, Generalization Accuracy: 0.87

|      |         | Predicted |       |         |
|------|---------|-----------|-------|---------|
|      |         | AML       | CML   | normMix |
| TRUE | AML     | 13.00     | 4.00  | 1.00    |
|      | other   | 0.00      | 58.00 | 2.00    |
|      | normMix | 3.00      | 2.00  | 11.00   |

Tables 14 and 15 Confusion Tables and Generalization Performance for rawByWell.robust Summarization for kNN and MLP Classifier Discriminating Between 3 Classes

TABLE 14 rawByWell.robust, Confusion Table, k Nearest Neighbor, Generalization Accuracy: 0.81

|      |         | Predicted |       |         |
|------|---------|-----------|-------|---------|
|      |         | AML       | CML   | normMix |
| TRUE | AML     | 10.00     | 7.00  | 1.00    |
|      | other   | 0.00      | 60.00 | 0.00    |
|      | normMix | 0.00      | 10.00 | 6.00    |

TABLE 15 rawByWell.robust, Confusion Table, MLP, Evidence Framework, Generalization Accuracy: 0.86

|      |         | Predicted |       |         |
|------|---------|-----------|-------|---------|
|      |         | AML       | CML   | normMix |
| TRUE | AML     | 14.00     | 3.00  | 1.00    |
|      | other   | 1.00      | 57.00 | 2.00    |
|      | normMix | 4.00      | 2.00  | 10.00   |

Tables 16 and 17: Confusion Tables and Generalization Performance for minusNegByWell.robust Summarization for kNN and MLP Classifier Discriminating Between 3 Classes

TABLE 16 minusNegByWellNormalizedWithinCurveRange.robust, Confusion Table, k Nearest Neighbor, Generalization Accuracy: 0.85

|      |         | Predicted |       |         |
|------|---------|-----------|-------|---------|
|      |         | AML       | CML   | normMix |
| TRUE | AML     | 13.00     | 5.00  | 0.00    |
|      | other   | 0.00      | 60.00 | 0.00    |
|      | normMix | 0.00      | 9.00  | 7.00    |

TABLE 17 minusNegByWellNormalizedWithinCurveRange.robust, Confusion Table, MLP, Evidence Framework, Generalization Accuracy: 0.89

|      |         | Predicted |       |         |
|------|---------|-----------|-------|---------|
|      |         | AML       | CML   | normMix |
| TRUE | AML     | 16.00     | 2.00  | 0.00    |
|      | other   | 0.00      | 56.00 | 4.00    |
|      | normMix | 2.00      | 2.00  | 12.00   |

Tables 18 and 19: Confusion Tables and Generalization Performance for minusNegByWellNormalizedWithinCurveRange.robust Summary of Results for kNN and MLP Classifier Discriminating Between 3 Classes

TABLE 18 minusNegByWellNormalizedWithinCurveRange.robust, Confusion Table, k Nearest Neighbor, Generalization Accuracy: 0.79

|      |         | Predicted |       |         |
|------|---------|-----------|-------|---------|
|      |         | AML       | CML   | normMix |
| TRUE | AML     | 7.00      | 7.00  | 4.00    |
|      | other   | 0.00      | 58.00 | 2.00    |
|      | normMix | 0.00      | 7.00  | 9.00    |

TABLE 19 minusNegByWellNormalizedWithinCurveRange.robust, Confusion Table, MLP, Evidence Framework, Generalization Accuracy: 0.45

|      |         | Predicted |       |         |
|------|---------|-----------|-------|---------|
|      |         | AML       | CML   | normMix |
| TRUE | AML     | 13.00     | 4.00  | 1.00    |
|      | other   | 0.00      | 57.00 | 3.00    |
|      | normMix | 4.00      | 2.00  | 10.00   |

TABLE 20

Sensitivities/Specificities for minusNegByWell.robust summarization with MLP classifier, overall specificity for healthy versus disease at the end.

| Sample type | Specificity | Sensitivity |
|-------------|-------------|-------------|
| AML         | 97%         | 89%         |
| Other       | 88%         | 93%         |
| Disease     | 75%         | 95%         |

Working Example 3

Classification Performance Only Using sCD117 Versus all Five sCD Antigens:

The raw classifier input (FIG. 6) suggests that sCD117 gives rise to a very strong signal and may already provide a considerable classification performance on its own. The analysis described was repeated before restricting to only one regressor (sCD117) and compared to the prediction results using all five sCD antigen probes, as in the first experiment. Experiments were performed to test whether using all regressors yielded a significantly improved generalization performance compared to predictions based on sCD117 only.

Except for one particular normalization method and classifier, where there was a tie, all tests consistently revealed significantly higher classification accuracies when using all five sCD antigen regressors, with an improvement of between 8% and 10% points. Significance levels were typically around p=5% and are expected to reduce to even higher significance for larger datasets. Details of significance levels and the confusion tables, again separately for all four summarization methods and both classifiers, can be found in Tables 21-33.

Specificity and sensitivity values as stated in Tables 34-35 ease interpretation of the results.

We observe that sCD117 alone is already a good marker to discriminate AML samples from healthy (norm-mix) samples. But the single sCD117 marker does not separate normMix samples from the other cancer types very well, leading to the very low sensitivity of the combined disease class.

The change of expression values was studied using the minusNegByWell.robust normalization. A significant change of expression of a single antigen between the three classes normal, cancer and AML can only be observed for sCD117. For normal control-samples we find a mean expression value of 3.534+/−0.285. Cancer-samples excluding AML range at 3.4569+/−0.1358. AML-cancer samples at 3.86+/−0.37. (All error bars are +/−1 standard deviation). We can conclude that on average cancer samples cause a slight decrease in expression of sCD117 compared to normal samples while AML samples cause the expression level of sCD117 increase. The observed decrease is well described for cancer samples is within 1 standard deviation error bars of either class and hence is not significant. In contrast the increase of expression for AML samples exceeds a 1 Standard deviation cut-off and hence meets this significance-criterion. This simplistic analysis suggests that sCD117 is not a promising marker for distinguishing between non-AML cancer and healthy normals, but instead is a statistically significantly marker for distinguishing AML samples from non-AML samples.

The result of this low-level analysis is in agreement with the confusion tables for the predictive power of sCD117 indicating a particular strong predictive power for the AML-sample class. The remaining markers give rise to a weaker signal which only allows sensible interpretation when used jointly as input for a classifier as discussed elsewhere.

Adding the additional four sCD antigens helps overcome this problem. Although sCD117 is a good single marker, the use of additional sCD probes improves the predictive accuracy (in terms of specificity) significantly. Consequently, a further improvement in specificity is reasonably expected by adding even more sCD antigen probes, beyond the five sCD antigens used in this experiment. An improvement in sensitivity is also expected by adding further individual sCD markers that individually have a defined sensitivity for a particular disease, in this case AML. The properties of sCD117 as a single marker also suggest that some of the sCD antigens, like sCD117, are very sensitive for a specific cancer family, in this case AML. The other markers studied in this investigation in contrast contribute to the classification jointly and only pattern learning on the five dimensional patterns allows us to extract useful information.

Tables 21, 22, 23, and 24 Below: rawByWell.mean Summarization—Confusion Tables for classification using sCD117 as single regressor versus using all five antigen probes. Table 25 below: statistical significance.

TABLE 21

Data: RawByWell.mean, All Variables, Confusion Table, MLP, Evidence Framework, Generalization Accuracy: 0.89

|      |         | Predicted |       |         |
|------|---------|-----------|-------|---------|
|      |         | AML       | CML   | normMix |
| TRUE | AML     | 13.00     | 4.00  | 1.00    |
|      | other   | 0.00      | 55.00 | 5.00    |
|      | normMix | 3.00      | 2.00  | 11.00   |

TABLE 22

Data: RawByWell.mean, sCD117 only, Confusion Table, MLP, Evidence Framework, Generalization Accuracy: 0.76

|      |         | Predicted |       |         |
|------|---------|-----------|-------|---------|
|      |         | AML       | CML   | normMix |
| TRUE | AML     | 14.00     | 4.00  | 0.00    |
|      | other   | 3.00      | 57.00 | 0.00    |
|      | normMix | 4.00      | 12.00 | 0.00    |

TABLE 23

Data: RawByWell.mean, All Variables, Confusion Table,
k-Nearest Neighbor, Generalization Accuracy: 0.84

|      |         | Predicted |       |         |
|------|---------|-----------|-------|---------|
|      |         | AML       | CML   | normMix |
| TRUE | AML     | 12.00     | 6.00  | 1.00    |
|      | other   | 0.00      | 60.00 | 0.00    |
|      | normMix | 0.00      | 9.00  | 7.00    |

TABLE 24

Data: RawByWell.mean, sCD117 only, Confusion Table,
k-Nearest Neighbor, Generalization Accuracy: 0.84

|      |         | Predicted |       |         |
|------|---------|-----------|-------|---------|
|      |         | AML       | CML   | normMix |
| TRUE | AML     | 13.00     | 5.00  | 0.00    |
|      | other   | 0.00      | 54.00 | 6.00    |
|      | normMix | 0.00      | 16.00 | 0.00    |

TABLE 25

Summary information accuracy and significance that using all
variables provides better classification than using sCD117 only

| Classification Method | Gen, Acc.All. | GenAcc CD117 only | Sig. Level |
|---|---|---|---|
| Evid, App.Framework | 84.04 | 75.53 | 0.07 |
| K. Nearest Neighbors | 84.04 | 71.28 | 0.00 |

Tables 26, 27, 28 and 29 Below: rawByWell.robust
Summarization—Confusion tables for Classification
Using sCD117 as Single Regressor Versus Using all
Five Antigen Probes. Table 30 Below: Statistical
Significance

TABLE 26

Data: rawByWell.robust, All Variables, Confusion Table, MLP,
Evidence Framework, Generalization Accuracy: 0.87

|      |         | Predicted |       |         |
|------|---------|-----------|-------|---------|
|      |         | AML       | CML   | normMix |
| TRUE | AML     | 14.00     | 3.00  | 1.00    |
|      | other   | 0.00      | 57.00 | 3.00    |
|      | normMix | 3.00      | 2.00  | 11.00   |

TABLE 27

Data: rawByWell.robust, sCD117 only, Confusion Table, MLP,
Evidence Framework, Generalization Accuracy: 0.78

|      |         | Predicted |       |         |
|------|---------|-----------|-------|---------|
|      |         | AML       | CML   | normMix |
| TRUE | AML     | 15.00     | 3.00  | 0.00    |
|      | other   | 1.00      | 58.00 | 1.00    |
|      | normMix | 3.00      | 13.00 | 0.00    |

TABLE 28

Data: rawByWell.robust, All Variables, Confusion Table,
k-Nearest Neighbor, Generalization Accuracy: 0.82

|      |         | Predicted |       |         |
|------|---------|-----------|-------|---------|
|      |         | AML       | CML   | normMix |
| TRUE | AML     | 10.00     | 7.00  | 1.00    |
|      | other   | 0.00      | 60.00 | 0.00    |
|      | normMix | 0.00      | 9.00  | 7.00    |

TABLE 29

Data: rawByWell.robust, sCD117 only, Confusion Table,
k-Nearest Neighbor, Generalization Accuracy: 0.74

|      |         | Predicted |       |         |
|------|---------|-----------|-------|---------|
|      |         | AML       | CML   | normMix |
| TRUE | AML     | 13.00     | 3.00  | 2.00    |
|      | other   | 0.00      | 55.00 | 5.00    |
|      | normMix | 0.00      | 14.00 | 2.00    |

TABLE 30

Summary information accuracy and significance that using all
variables provides better classification than using CD117 only

| Classification Method | Gen, Acc.All. | GenAcc sCD117 only | Sig.Level |
|---|---|---|---|
| Evid, App.Framework | 87.23 | 77.66 | 0.02 |
| K. Nearest Neighbors | 81.91 | 74.47 | 0.06 |

Tables 31, 32, 33 and 34 Below:
minusNegByWell.robust
Summarization—Confusion Tables for Classification
Using sCD117 as Single Regressor Versus Using all
Five Antigen Probes. Table 35 Below: Statistical
Significance

TABLE 31

Data: minusNegByWell.Robust, All Variables, Confusion Table,
MLP, Evidence Framework, Generalization Accuracy: 0.88

|      |         | Predicted |       |         |
|------|---------|-----------|-------|---------|
|      |         | AML       | CML   | normMix |
| TRUE | AML     | 14.00     | 4.00  | 0.00    |
|      | other   | 0.00      | 56.00 | 4.00    |
|      | normMix | 1.00      | 2.00  | 13.00   |

TABLE 32

Data: minusNegByWell.Robust, sCD117 only, Confusion Table,
MLP, Evidence Framework, Generalization Accuracy: 0.80

|      |         | Predicted |       |         |
|------|---------|-----------|-------|---------|
|      |         | AML       | CML   | normMix |
| TRUE | AML     | 15.00     | 3.00  | 0.00    |
|      | other   | 0.00      | 60.00 | 0.00    |
|      | normMix | 4.00      | 12.00 | 0.00    |

TABLE 33

Data: minusNegByWell.Robust, All Variables, Confusion Table, k-Nearest Neighbor, Generalization Accuracy: 0.85

| | | Predicted | | |
|---|---|---|---|---|
| | | AML | CML | normMix |
| TRUE | AML | 13.00 | 5.00 | 0.00 |
| | other | 0.00 | 60.00 | 0.00 |
| | normMix | 0.00 | 9.00 | 7.00 |

TABLE 34

Data: minusNegByWell.Robust, sCD117 only, Confusion Table, k-Nearest Neighbor, Generalization Accuracy: 0.79

| | | Predicted | | |
|---|---|---|---|---|
| | | AML | CML | normMix |
| TRUE | AML | 13.00 | 2.00 | 3.00 |
| | other | 0.00 | 57.00 | 3.00 |
| | normMix | 1.00 | 11.00 | 4.00 |

TABLE 35

Summary information accuracy and significance that using all variables provides better classification than using sCD117 only

| Classification Method | Gen, Acc.All. | GenAcc sCD117 only | Sig.Level |
|---|---|---|---|
| Evid, App.Framework | 88.30 | 79.79 | 0.06 |
| K. Nearest Neighbors | 85.11 | 78.72 | 0.05 |

Tables 36, 37, 38 and 39: minusNegByWellNormalizedWithinCurvekange.robust Summarization—Confusion Tables for Classification Using sCD117 as Single Regressor Versus Using All Five Antigen Probes. Table 40 Below: Statistical Significance

TABLE 36

Data: minusNegByWellNormalizedWithinCurveRange.robust, All Variables, Confusion Table, MLP, Evidence Framework, Generalization Accuracy: 0.85

| | | Predicted | | |
|---|---|---|---|---|
| | | AML | CML | normMix |
| TRUE | AML | 13.00 | 4.00 | 1.00 |
| | other | 1.00 | 57.00 | 2.00 |
| | normMix | 3.00 | 3.00 | 10.00 |

TABLE 37

Data: minusNegByWellNormalizedWithinCurveRange.robust, sCD117 only, Confusion Table, MLP, Evidence Framework, Generalization Accuracy: 0.79

| | | Predicted | | |
|---|---|---|---|---|
| | | AML | CML | normMix |
| TRUE | AML | 14.00 | 4.00 | 0.00 |
| | other | 0.00 | 60.00 | 0.00 |
| | normMix | 6.00 | 10.00 | 0.00 |

TABLE 38

Data: minusNegByWellNormalizedWithinCurveRange.robust, All Variables, Confusion Table, k-Nearest Neighbor, Generalization Accuracy: 0.81

| | | Predicted | | |
|---|---|---|---|---|
| | | AML | CML | normMix |
| TRUE | AML | 8.00 | 7.00 | 3.00 |
| | other | 0.00 | 58.00 | 2.00 |
| | normMix | 0.00 | 6.00 | 10.00 |

TABLE 39

Data: minusNegByWellNormalizedWithinCurveRange.robust, sCD117 only, Confusion Table, k-Nearest Neighbor, Generalization Accuracy: 0.81

| | | Predicted | | |
|---|---|---|---|---|
| | | AML | CML | normMix |
| TRUE | AML | 10.00 | 2.00 | 6.00 |
| | other | 0.00 | 59.00 | 1.00 |
| | normMix | 3.00 | 6.00 | 7.00 |

TABLE 40

Summary information accuracy and significance that using all variables provides better classification than using sCD117 only

| Classification Method | Gen, Acc.All. | GenAcc sCD117 only | Sig.Level |
|---|---|---|---|
| Evid, App.Framework | 85.11 | 78.72 | 0.09 |
| K. Nearest Neighbors | 80.85 | 80.85 | 0.64 |

TABLE 41

Sensitivities/Specificities for minusNegByWell.robust summarization with MLP classifier. First: Top part of the table: sCD117 as the only regressor, below: using all five antigen probes.

| Sample type | Specificity | Sensitivity |
|---|---|---|
| Using sCD117 only | | |
| AML | 95% | 83% |
| other | 56% | 100% |
| Disease | 0% | 100% |
| Using all five antigens | | |
| AML | 99% | 78% |
| other | 82% | 93% |
| Disease | 81% | 95% |

TABLE 42

Sensitivities/Specificities for minusNegByWell.robust summarization with kNN classifier. First: Top part of the table: sCD117 as the only regressor, below: using all five antigen probes.

| Sample type | Specificity | Sensitivity |
|---|---|---|
| Using sCD117 only | | |
| AML | 98% | 81% |
| other | 68% | 95% |
| Disease | 25% | 92% |

TABLE 42-continued

Sensitivities/Specificities for minusNegByWell.robust summarization with kNN classifier. First: Top part of the table: sCD117 as the only regressor, below: using all five antigen probes.

| Sample type | Specificity | Sensitivity |
|---|---|---|
| Using all five sCD antigens | | |
| AML | 100% | 81% |
| other | 68% | 100% |
| Disease | 44% | 100% |

We can conclude that although sCD117 is a good single marker, the use of additional sCD probes improves the predictive accuracy significantly. We can consequently reasonably expect a further improvement by adding even more sCD antigen probes, beyond the five sCD antigens used in this experiment. The properties of sCD117 as a single marker also suggest that some of the antigens, like sCD117, are very sensitive for a specific cancer family, in this case AML. The other markers studied in this investigation in contrast contribute to the classification jointly and only pattern learning on the five dimensional patterns allows us to extract useful information.

In data not shown here, we have found that on average cancer samples cause a slight decrease in expression of sCD117 compared to normal samples, while AML samples show an increase in expression level of sCD117. The change of expression values was studied using the minusNegByWell.robust normalization. A significant change of expression of a single antigen between the three classes of normal, cancer and AML was only be observed for sCD117.

For normal control-samples we find a mean expression value of 3.534+/−0.285. Cancer-samples excluding AML range at 3.4569+−0.1358. AML-cancer samples at 3.86+/−0.37. (All error bars are +/−1 standard deviation). We can conclude that on average cancer samples cause a slight decrease in expression of sCD117 compared to normal samples while AML samples cause the expression level increase. The observed decrease is well described for cancer samples is within 1 standard deviation error bars of either class and hence is not significant.

In contrast the increase of expression for AML-samples exceeds a 1 standard deviation cut-off and hence meets this significance-criterion. This simplistic analysis suggests that sCD17 is not a promising marker for distinguishing between non-AML cancer and healthy normal controls, but instead is a statistically significantly marker for distinguishing AML samples from non-AML samples. The result of this low-level analysis is in agreement with the confusion tables for the predictive power of sCD117 indicating particular strong predictive power for the AML-sample class. The remaining markers give rise to a weaker signal which only allows sensible interpretation when used jointly as input for a classifier as discussed elsewhere. As described herein, the applicability of sCD antigens in the diagnosis, classification and monitoring of human leukemias was studied. We studied the predictive performance using a plurality of sCD antigens, e.g., only 5 sCD antigens, whose expression levels in human samples, both diseased and in healthy control samples, were measured using a chip-based antibody array technology.

It could be successfully demonstrated that the detected sCD antigen expression levels can be used to predict leukemia with a considerably high accuracy of 79%-89%. We carefully examined the issue of alternative normalization strategies, which lead to a comparable and meaningful data basis for classification.

By varying the analysis method, considering only AML, normMix and all other samples as labels, we demonstrated the high predictive value of sCD antigen expression profiles/fingerprints on this subset of the leukemia families. The discrimination of AML versus other leukemias and healthy control (normal) samples yielded especially promising results using the five sCD antigen probes employed in this investigation.

In order to evaluate the predictive power of utilising multiple sCD antigen probes as opposed to a single sCD antigen probe, we tested the predictive power using only one soluble CD antigen, sCD117, versus using all 5 sCD antigens. We demonstrated that although this single sCD antigen has a significant predictive performance on its own, the addition of the other sCD antigens increases the discriminative power in a statistically significant manner, despite the low number of samples. This suggests that the predictive performance as measured by the specificity could be increased even further by adding more sCD antigens. Indeed the utilisation of multiple sCD antigens in excess of the 5 employed here is predicted by these experiments to increase the sensitivity and specificity of this method and thus the ability to discriminate between different leukaemia subclasses and indeed between different disease states, very significantly. As such the use of multiple sCD antigens may in principle be used for monitoring the response to therapeutic interventions in those individuals with leukaemia, for diagnosis and classification of the leukaemia subtype and most likely consequently also for prognostic insights. There are likely also to be other uses such as the detection of minimal residual disease, detection of early relapse, prognostic stratification, early diagnosis, early detection of relapse, and individual sensitivity to a particular therapeutic compound or biologic.

The methods described herein are not restricted to the analysis of whole blood, serum or plasma and indeed sCD molecules are known to be present in many other body fluids. Furthermore the methods described herein are not restricted to use in humans, and indeed such a method may prove to be of immense use in veterinary applications. Neither is the technology used to measure levels of the sCD molecules in body fluid necessarily restricted to those technologies such as bead-based and chip-based outlined above.

The current method in its present form is expected to be of considerable use in human leukemias and in particular in acute myeloid leukaemia (AML) for which there is a significant unmet medical need for diagnostic, prognostic and 'theranostic' (diagnostic tests that diagnose the disease, help choose the correct treatment regime and assist monitoring of the patient response) biomarkers. The utilisation of sCD profiling/fingerprinting in AML and other human leukemias is expected to be of considerable clinical utility both in primary and tertiary settings and it is expected that the use of sCD profiling/fingerprinting in therapeutic contexts will help facilitate the detection of minimal residual disease following therapy and also the monitoring of individual response to therapeutic interventions. The identification of poor prognostic groups using this technology can enable pre-selection of those individuals requiring more aggressive therapeutic interventions and in addition those that require more frequent intensive monitoring. The method can help predict those individuals that are likely to be intolerant to a particular therapeutic intervention and those individuals that are likely or be responders, non-responders, or rapid responders to a particular therapeutic intervention. It is predicted that the individual sCD antigens compromising the pattern/profile/fingerprint may themselves also be potential targets for therapy and as such this method also provides a means of identifying sCD antigens and their cell surface counterparts that might, in principle, be targeted by therapeutic interventions.

Though the methods encompassing the detection of soluble antigens in body fluids is not limited to any particular method of technology, an exemplary protocol using GenTel antibody array technology platform is described below.

Multiplex Assay Methods Using the GenTel Antibody Array Technology Platform

1. Procurement of matched antibody pairs with priority to match pairs including multiple clones of capture and detector antibody specificities.
2. Formulation of antibodies and antigens: (a) Aliquots of all reagents are prepared upon suspension and stored at −20° C. (b) Capture antibodies intended for arraying are suspended in sterile 1× GenTel Rinse Buffer, unless incompatible with vendor specifications at a final concentration of 1.0 mg/mL. (c) Aliquots of recombinant proteins are suspended in sterile 1× GenTel Rinse Buffer at a final concentration of 100 ug/mL. (d) Aliquots of detector antibodies are suspended in sterile 1× GenTel Rinse Buffer at a final concentration of 200 µg/mL.

All slides are arrayed using a Gesim Nanoplotter 2.0/E piezoelectric instrument using the following printing parameters: (i) Well layout: 2×8 arrays per 1×3 slide, (ii) Replicate spots: 3, (iii) Spot OD: ~220 um, (iv) Spot pitch: ~350 um, (v) Positive control: Cy3 labeled IgG at 50 ug/mL in 1× GenTel Print Buffer, (vi) Positive control: BSA/Biotin at 100 ug/mL in 1×GenTel Print Buffer, (vii) Capture antibody: printed at 500 ug/mL in 1×GenTel Print Buffer, (viii) Negative control: 1× GenTel Print Buffer, (ix) Relative Humidity: 60%, (x) Temperature: ambient room temperature.

Slides are cured before use by incubating for 3 days under vacuum with copious desiccant. Printed slides are quality controlled by sampling every 5 slides and scanned to inspect for the following structural and functional characteristics: (i) Spot morphology, (ii) Potential missed spots, and (iii) Correct alignment.

3. Reagent specificity screening is performed to identify which reagent sets are functionally specific by screening of materials as follows: (a) Every capture antibody specificity is printed as microspots in every array, (b) Each array is probed with a different individual antigen (20 ng/mL) and the corresponding single biotinylated detector antibody specificity, (c) Each array is probed with a single detector antibody specificity in the absence of antigen to measure capture antibody/detector antibody cross reactivity.
4. The high and low endpoints of standard curves are determined using matched pairs that demonstrate minimal non-specific binding (less than 3% of intended signal). The matched pairs are selected to prepare eight (8) point single plex standard curves including one (1) blank (no antigen) in 1× GenTel Wash Buffer. (a) Standard curves are prepared using single antigen/single detector antibody pairs on slides listed using serially diluted purified antigens (initial concentration is 200 ng/mL), (b) Commercially available normal human serum/plasma is serially diluted pooled using dilutions ranging from 1:2 through 1:300 in IX GenTel Wash Buffer, (c) The wells containing the highest signal in the linear portion of the standard curve but below saturation are selected to measure any capture antibody/antigen specificity. (d) The concentration of the antigen cocktail is selected based on the highest signal before saturation on the single plex standard curves.
5. Dynamic range and Levels of Detection (LOD) are measured with menus of analytes, which are selected using specificity evaluation data and sample dilution experiments. (a) Cocktail of antigen is serially diluted to prepare two eight (8) point standard curves including with 1 blank (no antigen) on each slide. (b) Multiplex standard curves are graphed and dynamic range and LOD are measured and reported.
6. Optimization of multiplex immunoassays is adjusted using the following parameters: (a) Standard curve concentrations, (b) Detector antibody concentrations, (c) Printed capture antibody concentrations and (d) Possible application of diluents with carrier (BSA, FBS).
7. Panel validation: Standard curve slope consistency and precision are evaluated by preparing two (2) eight (8)-point standard curves including blanks per curve (n=2 standard curves) on three (3) three slides per day (n=6 standard curves) for three (3) consecutive days (n=18 standard curves). Precision measurements are reported as the following: (i) Mean % CV within slide, (ii) Mean % CV slide to slide (iii) Mean % CV day to day. Slopes and precision are measured and recorded. The percentage accuracy (dilutional recovery) is measured using the two-slide validation format as discussed above using a scattered well format. (i) Five (5) dilution points within the dynamic range of standard curves are prepared in triplicate. (ii) Data reported as the percent accuracy of expected values.

Additional validation procedures may also be include: (i) Replicate standard curves with replicate blanks and spiked samples near the LOD to measure LOQ, (ii) Replicate pooled normal human serum/plasma samples for sample replicate consistency, (iii) Spiked serum/plasma sample evaluation for accuracy and consistency, and/or (iv) Spiked matrix sample evaluation for accuracy and consistency.

Exemplary General Assay Procedure:

1. Reagents and Materials include 1× GenTel Wash Buffer, 1× GenTel Rinse Buffer, 1× GenTel Protein Free Blocking Buffer, 5× GenTel Print Buffer, GenTel PATHplus Thin Film Nitrocellulose Slides, GenTel SIMplex 16/64 Well Separator Device, Monoclonal Capture Antibodies, Recombinant Antigen standards, Detector Antibodies, and Streptavidin/Dy549.
2. Slide Printing: Printing is performed using a Gesim Nanoplotter 2.0/E with the following parameters for geometric layouts and sample constituents: Well layout—2×8, Replicate spots—3, Spot OD-~220 um, Spot pitch-~350 um, Positive control—Cy3 labelled IgG at 50 ug/mL in 1× GenTel Print Buffer, Positive control—BSA/Biotin at 100 ug/mL in 1× GenTel Print Buffer, Capture antibody—printed at 500 ug/mL in 1× GenTel Print Buffer, Negative control—1× GenTel Print Buffer, RH—60% and Temperature—ambient. Post printing, slides are cured before use by incubating for at least 3 days under vacuum with copious desiccant.
3. Assay Procedure:

Blocking: Slides to be used in the assay are plunged into a 50 mL conical tube containing approximately 45 mL of 1× GenTel Protein Free Blocking Buffer, and gently inverted five times to agitate, and incubated at room temperature for one hour.

Assembling slide/well apparatus: The slides are removed from the blocking buffer and immediately placed into the lower structure of the SIMplex well separator device. The upper structure of the SIMplex well separator device is attached to the lower structure. Excess liquid is removed by rigorously flicking into liquid waste receptacle Assay Procedure Add 70 µL of standards or body fluid samples to the wells. Place plate-sealing tape over the well plate. Incubate at room temperature for 1 hour with gentle agitation on rotator shaker. Remove plate-sealing tape. Wash well plate using 1× GenTel Wash Buffer either by hand or using automated plate washer with the following conditions: 6 replicate washes at 150 µL per wash effected by flicking excess liquid out of wells. Add 70 µL of Detector Antibody to all wells, place plate sealing tape over the well plate. Incubate at room temperature for 1 hour with gentle agitation on rotator shaker. Remove plate-sealing tape. Wash well plate as above. Add 70 µL of Detection Reagent to all wells. Place plate-sealing tape over the well plate. Incubate at room temperature for 1 hour with gentle agitation or rotator shaker. Remove plate-sealing tape. Wash well plate as above. Carefully remove upper structure from SIMplex unit. Briefly and gently rinse slides with 1× GenTel Rinse Buffer using a squirt bottle. Dry slides under a gentle stream of compressed nitrogen.

Slide Scanning Scanner—Tecan Reloaded LS300 (or LS400), Gain—130, Resolution—10 µm.

Figure 11:
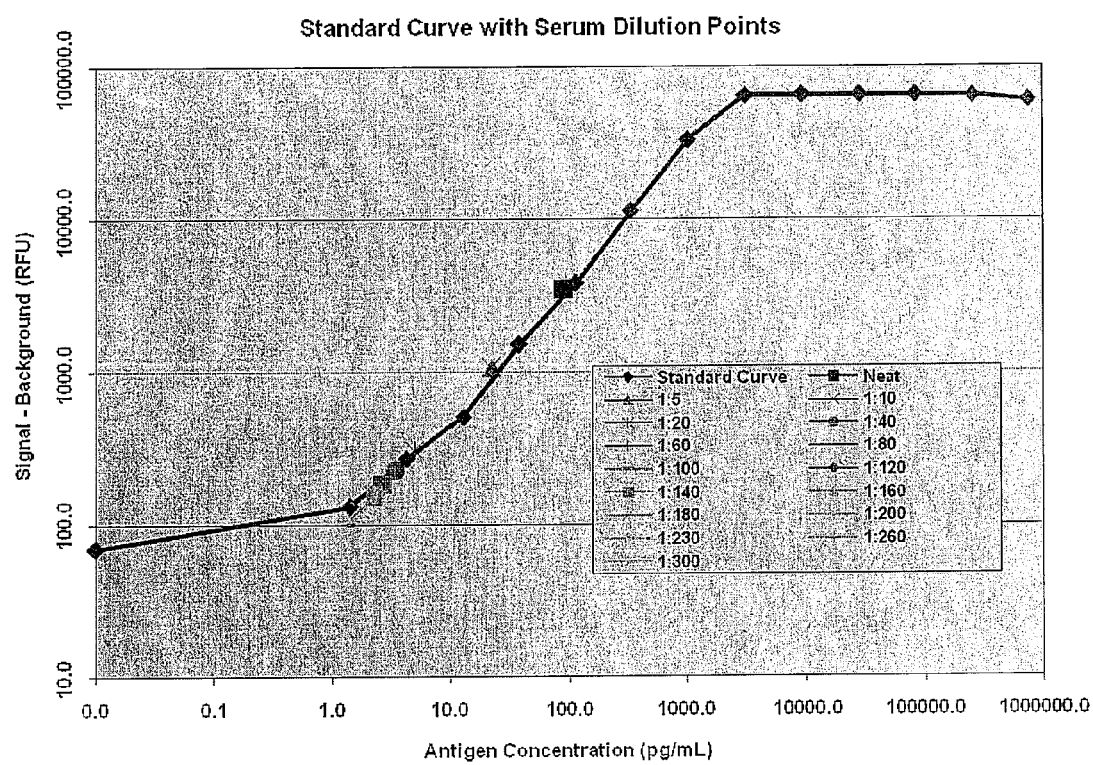
FIG. 11: Displays Standard Curve on dilutions of CD178

A standard curve was generated using the above described techniques on dilutions of sCD178 in normal sera and the following reagents: 15 point standard curve with one blank (no antigen), 16 Normal Pooled Human plasma samples at different dilution levels, CD178, Capture antibody Anti Human Fas Ligand/TNFSF6 Monoclonal Antibody (Clone 100419), R&D Systems, MAB126; Analyte-Recombinant Human Fas Ligand/TNFSF6, R&D Systems, 126-FL-010; and Detector Antibody—Anti Human Fas Ligand/TNFSF6 Biotinylated Affinity Purified Polyclonal Antibody, R&D Systems, BAF126. See FIG. 11.

Figure 12:
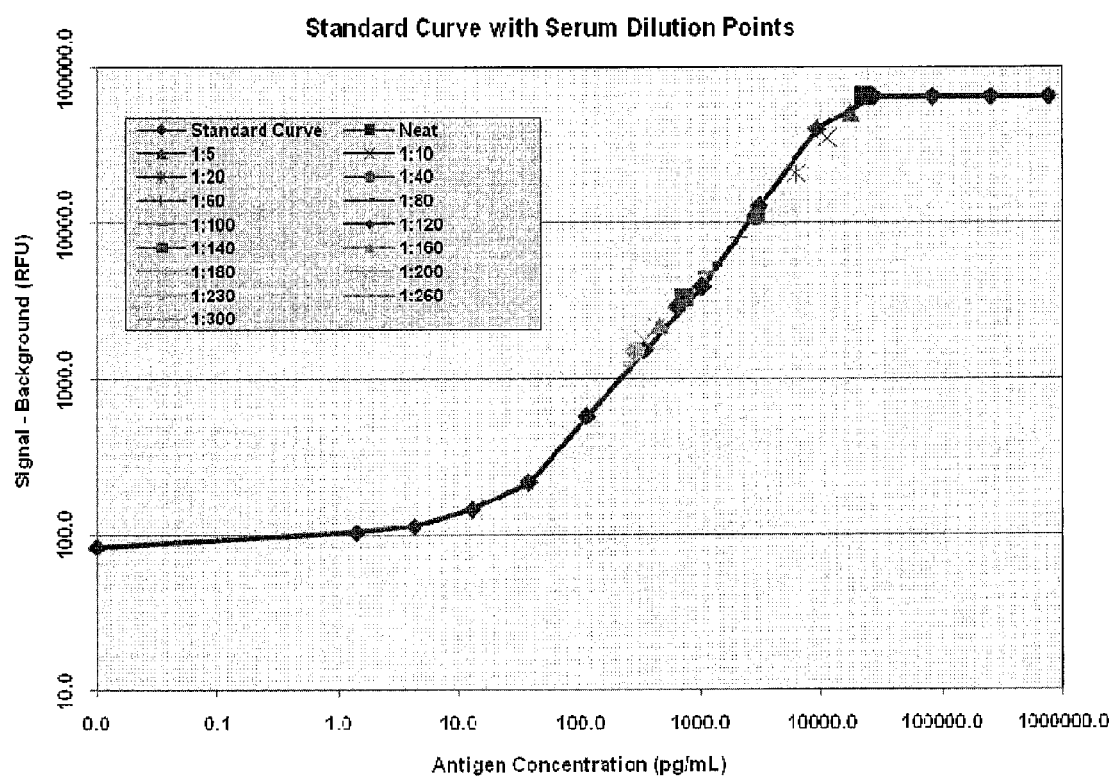
FIG. 12: Displays Standard Curve on dilutions of CD127

A Standard curve was generated using the above described techniques on dilutions of CD127 in normal sera and the following reagents: Capture Antibody—Anti Human IL-7 R alpha MAb (Clone 40131) Antibody, R&D Systems, MAB306; Analyte—Recombinant Human IL-7 R alpha/Fc Chimera, CF, R&D Systems, 306-IR-050; and Detector Antibody—Anti Human IL-7 R alpha Biotinylated Affinity Purified Polyclonal Antibody, R&D Systems, BAF306. See FIG. 12.

Combination of a specific set of sCD antigens:

The levels of a five sCD antigens were assayed in sera from healthy controls (normals) and from patients with the following leukemias: AML (acute myeloid leukemia), CML (chronic myeloid leukemia), NHL (non-Hodgkin's lymphoma), and CLL (chronic lymphocytic leukemia). For this purpose five soluble CD antigens: sCD14, sCD30, sCD54, sCD117, sCD130 were measured using a single-blinded protocol in plasma taken from both patients and healthy controls using matched monoclonal antibody pairs that were either attached to Luminex microbeads, or arrayed onto a chip using the chip-based methodology and technology of GenTel Biosciences Inc. Patterns of 5 or more sCD antigens measured in serum (or in principle in plasma or in any other body fluids such as: pleural fluid, urine, ascitic fluid, saliva, uveal fluid and so on) can be used to generate sCD protein expression signatures that are characteristic of cancer as opposed to normals, or that are characteristic of a particular disease state, namely in this instance of one particular leukemia type vs. other leukemia types and healthy normal controls. The hypothesis was that patterns of 5 or more sCD antigens would be more significant indicators of a specific disease state—whether it be cancer vs. healthy controls or cancer sub-type vs. other cancer sub-types—than individual sCD antigens on their own.

Working Example 4

The interchangeability of various sCD assay techniques was confirmed by comparison of the Luminex platform to the GenTel biochip. The results summarized below were obtained by twenty-fold cross-validation and resampling fifty times. This ensures that the random variation due to single-mode approximations in the evidence approximation MLP and the instability of k-NN are minimized. For every sample for which both GenTel as well as Luminex measurements were available data have been paired. In general we do not observe any significant differences between the generalization accuracies of matching assays. The main conclusion is therefore that we cannot conclude one of the approaches to be superior of the other. However, there is a borderline significant difference ($p=0.06$) in the four-class problem of separating AML, CLL, CML, and NML samples, in which Luminex measurements provided more information for the separation of cancer types. The specificity/sensitivity differences reflect this.

For AML/Other separation we were unable to detect a significant difference between both approaches, sensitivity/specificity differences are within range of expected fluctuations.

Classification Performance AML/other

TABLE 48

Data: Luminex Confusion Table, MLP, Evidence Framework, Generalization Accuracy: 0.89

|  |  | Predicted | |
|---|---|---|---|
|  |  | AML | normMix |
| TRUE | AML | 9.96 | 6.04 |
|  | other | 2.44 | 59.56 |

TABLE 49

Data: Luminex Confusion Table, k Nearest Neighbor, Generalization Accuracy: 0.83

|  |  | Predicted | |
|---|---|---|---|
|  |  | AML | normMix |
| TRUE | AML | 3.82 | 12.18 |
|  | other | 0.90 | 61.10 |

TABLE 50

Data: GenTel Confusion Table, MLP, Evidence Framework, MLP, Evidence Framework, Generalization Accuracy: 0.94

|  |  | Predicted | |
|---|---|---|---|
|  |  | AML | normMix |
| TRUE | AML | 12.00 | 4.00 |
|  | other | 0.72 | 61.28 |

TABLE 51

Data: GenTel Confusion Table, k Nearest Neighbor Generalization Accuracy: 0.91

|  |  | Predicted | |
|---|---|---|---|
|  |  | AML | normMix |
| TRUE | AML | 8.98 | 7.02 |
|  | other | 0.00 | 62.00 |

TABLE 52

Generalization Accuracy and Significance for GenTel and Luminex based dichotomous classification. Note that the observed differences are not significant.

| Classification Method | Gen, Acc.Luminex. | GenAcc GenTel | Sig.Level |
|---|---|---|---|
| Evid, App.Framework | 89.13 | 93.95 | 0.98 |
| K. Nearest Neighbors | 83.23 | 91.00 | 1.00 |

The main conclusion for this experiment is that both platforms perform very comparable.

For easy interpretation we list specificity/sensitivity tables for both platforms side by side.

TABLE 53

Sensitivity/specificity comparison GentelBio vs. Luminex for MLP classifier.

| Sample type | Specificity | Sensitivity |
|---|---|---|
| Gentel | | |
| AML | 98% | 75% |
| Other | 98% | 99% |
| Luminex | | |
| AML | 96% | 62% |
| Other | 85% | 96% |

Classification Performance all Four Classes

TABLE 54

Data: Luminex Confusion Table, MLP Evidence Framework, Generalization Accuracy: 0.78

| | | Predicted | | | |
|---|---|---|---|---|---|
| | | AML | CLL | CML | NHL |
| TRUE | AML | 12.34 | 2.06 | 1.02 | 0.58 |
| | CLL | 0.06 | 19.66 | 1.68 | 2.60 |
| | CML | 0.64 | 1.98 | 20.96 | 0.42 |
| | NHL | 1.18 | 4.16 | 0.02 | 6.64 |

TABLE 55

Data: Luminex Confusion Table, K, Nearest Neighbor, Generalization Accuracy: 0.62

| | | Predicted | | | |
|---|---|---|---|---|---|
| | | AML | CLL | CML | NHL |
| TRUE | AML | 4.26 | 5.94 | 2.00 | 3.80 |
| | CLL | 0.00 | 21.06 | 2.08 | 0.86 |
| | CML | 0.08 | 5.94 | 17.90 | 0.08 |
| | NHL | 1.96 | 6.14 | 0.00 | 3.90 |

TABLE 56

Data: Gentel Confusion Table, MLP Evidence Framework, Generalization Accuracy: 0.66

| | | Predicted | | | |
|---|---|---|---|---|---|
| | | AML | CLL | CML | NHL |
| TRUE | AML | 13.62 | 2.02 | 0.34 | 0.02 |
| | CLL | 1.40 | 15.12 | 4.84 | 2.64 |
| | CML | 1.02 | 4.26 | 16.34 | 2.38 |
| | NHL | 0.00 | 3.50 | 3.642 | 4.86 |

TABLE 57

GenTel Confusion Table, K, Nearest Neighbor, Generalization Accuracy: 0.58

| | | Predicted | | | |
|---|---|---|---|---|---|
| | | AML | CLL | CML | NHL |
| TRUE | AML | 11.76 | 1.24 | 3.00 | 0.00 |
| | CLL | 0.74 | 12.60 | 9.46 | 1.20 |
| | CML | 2.70 | 5.96 | 14.18 | 1.16 |
| | NHL | 0.00 | 2.14 | 4.10 | 5.76 |

TABLE 58

Generalization Accuracy and Significance for GenTel and Luminex based polychotomous classification. Note that the observed difference in Row 1 is borderline significant, the difference in Row 2 is not significant.

| Classification Method | Gen, Acc.Luminex. | GenAcc GenTel | Sig.Level |
|---|---|---|---|
| Evid, App. Framework | 78.42 | 65.71 | 0.06 |
| K. Nearest Neighbors | 62.00 | 58.29 | 0.37 |

| Sample type | Specificity | Sensitivity |
|---|---|---|
| Gentel | | |
| AML | 95% | 85% |
| CLL | 80% | 63% |
| CML | 82% | 68% |
| NHL | 81% | 40% |
| Luminex | | |
| AML | 96% | 72% |
| CLL | 84% | 82% |
| CML | 95% | 87% |
| NHL | 94% | 55% |

Working Example 5

Patterns for 5-Plex Experiment

The classification performance from the classifiers described above proves the usefulness of multiple antigens for the purpose of disease classification. The purpose of this additional document is to depict the information that is inherent to patterns of expression level of multiple antigens. For this illustration we will restrict the focus on three different disease classes—AML, all other cancers and healthy controls. The plots in this document are generation basis of the "minusNegByWell.robust" normalization method as described above. In other words, prior to the generation of scatter plots the data has been normalized using the IWLS robust mean estimator on a per well basis.

For each of 5 sCD specificities we plotted 2d-scatter plots for all possible pairings. A specificity plotted against itself resembles univariate analysis as commonly undertaken. The additional scatter plots yield 2 dimensional projections of the 5-dimensional space that illustrate additional patterns and structure that can only be recovered by examining multiple dimensions (here 2) simultaneously. The algorithms as discussed above perform classification on all 5 dimensions which yields an additional improvement, but the learned parameters of those algorithms, specifying a pattern structure, is implementation specific. Hence scatter plots are illustrated here as a means of capturing the nature of the patterns we identify.

First CD117 is studied and illustrated. This is the only marker that can yields good classification performance on its own. The discriminative performance can clearly be read of from the first scatter plot CD117 against itself. The other 4 scatter plots illustrate that additional specificities help tease out structure that cannot be captured by a single antigen. For instance CD11 vs CD14 illustrates the benefit from introducing the additional dimension in the pattern.

Similar scatter plots are provided for the remaining pairings of the full set of the 5 soluble CD antigens described in the above working examples.

One skilled in the art will readily appreciate that the present invention is well adapted to carry out the objects and obtain the ends and advantages mentioned as well as those inherent therein. The immunological methods and devices for detecting analytes in biological samples as described herein are presently representative of preferred embodiments, are exemplary and not intended as limitations on the scope of the invention. Changes therein and other uses will occur to those skilled in the art which are encompassed within the spirit of the invention or defined by this scope with the claims.

It will be readily apparent to one skilled in the art that varying substitutions and modifications may be made to the invention disclosed herein without departing from the scope and spirit of the invention. All references and citations disclosed herein are incorporated by reference in their entirety.

References

1. Probable networks and plausible predictions-a review of practical Bayesian methods for supervised neural networks; Mackay D. J. C 1995; Network: Computation in Neural Systems
2. Nearest neighbour (NN) norms: NN pattern classification techniques; Dasarathy, B. V.; Los Alamitos: IEEE Computer Society Press, 1990
3. Robust regression using iteratively reweighted least-squares; Holland, P. W. and Welsch, R. E.; Communications in Statistics-Theory and Methods
4. Pattern Classification; Duda, R. O. and Hart, P. E. and Stork, D. G.; Wiley-Interscience 2nd edition, Wiley, 2001

TABLE 43

Human CD Antigen Differentiation Molecules (as of November 2007). List taken from: the url: hcdm.org/CD1toCD350.htm downloaded on Nov. 6, 2007

| MOLECULE | | Gene Name | GeneID |
|---|---|---|---|
| CD1a | T6/leu-6, R4, HTA1 | CD1A | 909 |
| CD1b | R1 | CD1B | 910 |
| CD1c | M241, R7 | CD1C | 911 |
| CD1d | R3 | CD1D | 912 |
| CD1e | R2 | CD1E | 913 |
| CD2 | T11; Tp50; sheep red blood cell (SRBC) receptor; LFA-2; CD3 complex, T3, Leu4 | CD2 | 914 |
| CD3d | | CD3D | 915 |
| CD3e | | CD3E | 916 |
| CD3g | | CD3G | 917 |
| CD4 | OKT4, Leu 3a, T4 | CD4 | 920 |
| CD5 | Tp67; T1, Ly1, Leu-1 | CD5 | 921 |
| CD6 | T12 | CD6 | 923 |
| CD7 | Leu 9, 3A1, gp40, T cell leukemia antigen | CD7 | 924 |
| CD8α | OKT8, LeuT, LyT2, T8 | CD8A | 925 |
| CD8β | | CD8B1 | 926 |
| CD9 | Drap-27, MRP-1, p24, leucocyte antigen MIC3 | CD9 | 928 |
| CD10 | CALLA, membrane metalloendopeptidase | MME | 4311 |
| CD11a | alphaL; LFA-1, gp180/95 | ITGAL | 3683 |

TABLE 43-continued

Human CD Antigen Differentiation Molecules (as of November 2007). List taken from: the url: hcdm.org/CD1toCD350.htm downloaded on Nov. 6, 2007

| MOLECULE | | Gene Name | GeneID |
|---|---|---|---|
| CD11b | alphaM; alpha-chain of C3bi receptor, gp155/95, Mac-1, Mo1 | ITGAM | 3684 |
| CD11c | alphaX; a-chain of: complement receptor type 4 (CR4); gp150/95 | ITGAX | 3687 |
| CDw12 | P90-120 | | 23444 |
| CD13 | Aminopeptidase N, APN, gp150, EC 3.4.11.2 | ANPEP | 290 |
| CD14 | LPS receptor | CD14 | 929 |
| CD15 | Lewis X, CD 15u: sulphated Lewis X. CD 15s: sialyl Lewis X | | carbohydrate antigen |
| CD16a | Fc gamma R IIIa, | FCGR3A | 2214 |
| CD16b | Fc gamma R IIIb | FCGR3B | 2215 |
| CD17 | LacCer, lactosylceramide | | carbohydrate antigen |
| CD18 | β2-Integrin chain, macrophage antigen 1 (mac-1) | ITGB2 | 3869 |
| CD19 | Bgp95, B4 | CD19 | 930 |
| CD20 | B1; membrane-spanning 4-domains, subfamily A, member 1 | MS4A1 | 931 |
| CD21 | C3d receptor, CR2, gp140; EBV receptor | CR2 | 1380 |
| CD22 | Bgp135; BL-CAM, Siglec2 | CD22 | 933 |
| CD23 | Low affinity IgE receptor; FceRII; gp50-45; Blast-2 | FCER2 | 2208 |
| CD24 | heat stable antigen homologue (HSA), BA-1 | CD24 | 934 |
| CD25 | Interleukin (IL)-2 receptor a-chain; Tac-antigen | IL2RA | 3559 |
| CD26 | Dipeptidylpeptidase IV; gp120; Ta1 | DPP4 | 1803 |
| CD27 | T14, S152 | TNFRSF7 | 939 |
| CD28 | Tp44 | CD28 | 940 |
| CD29 | Integrin β1 chain; platelet GPIIa; VLA (CD49) beta-chain | ITGB1 | 3688 |
| CD30 | Ki-1 antigen, Ber-H2 antigen | TNFRSF8 | 943 |
| CD31 | PECAM-1; platelet GPIIa'; endocam | PECAM1 | 5175 |
| CD32 | Fcgamma receptor type II (FcgRII), gp40 | FCGR2A | 2212 |
| CD33 | My9, gp67, p67 | CD33 | 945 |
| CD34 | My10, gp105-120 | CD34 | 947 |
| CD35 | C3b/C4b receptor; complement receptor type 1 (CR1) | CR1 | 1378 |
| CD36 | platelet GPIV, GPIIIb, OKM-5 antigen | CD36 | 948 |
| CD37 | gp40-52 | CD37 | 951 |
| CD38 | T10; gp45, ADP-ribosyl cyclase | CD38 | 952 |
| CD39 | gp80, ectonucleoside triphosphate diphosphohydrolase 1 | ENTPD1 | 953 |
| CD40 | Bp50, TNF Receptor 5 | TNFRSF5 | 958 |
| CD41 | platelet glycoprotein GPIIb | ITGA2B | 3674 |
| CD42a | platelet glycoprotein GPIX | GP9 | 2815 |
| CD42b | platelet glycoprotein GPIb-a | GP1BA | 2811 |
| CD42c | platelet glycoprotein GPIb-β | GP1BB | 2812 |
| CD42d | platelet glycoprotein GPV | GP5 | 2814 |
| CD43 | Leukosialin; gp95; sialophorin; leukocyte sialoglycoprotein | SPN | 6693 |
| CD44 | Pgp-1; gp80-95, Hermes antigen, ECMR-III and HUTCH-I. | CD44 | 960 |
| CD44R | CD44 variant; CD44v1-10 | | 960 |

TABLE 43-continued

Human CD Antigen Differentiation Molecules (as of November 2007).
List taken from: the url: hcdm.org/CD1toCD350.htm
downloaded on Nov. 6, 2007

| MOLECULE | | Gene Name | GeneID |
|---|---|---|---|
| CD45 | LCA, B220, protein tyrosine phosphatase, receptor type, C | PTPRC | 5788 |
| CD45RA | Restricted T200; gp220; isoform of leukocyte common antigen | | see CD45 |
| CD45RO | Restricted T200; gp180; | | see CD45 |
| CD45RB | Restricted T200; isoform of leukocyte common antigen | | see CD45 |
| CD45RC | Restricted T200; isoform of leukocyte common antigen | | see CD45 |
| CD46 | Membrane cofactor potein (MCP) | MCP | 4179 |
| CD47 | Integrin-associated protein (IAP), Ovarian carcinoma antigen OA3 | CD47 | 961 |
| CD48 | BLAST-1, Hulym3, OX45, BCM1 | CD48 | 962 |
| CD49a | Integrin a1 chain, very late antigen, VLA 1a | ITGA1 | 3672 |
| CD49b | Integrin a2 chain, VLA-2-alpha chain, platelet gpIa | ITGA2 | 3673 |
| CD49c | Integrin a3 chain, VLA-3 alpha chain | ITGA3 | 3675 |
| CD49d | Integrin a4 chain,, VLA-4-alpha chain | ITGA4 | 3676 |
| CD49e | Integrin a5 chain,, VLA-5 alpha chain | ITGA5 | 3678 |
| CD49f | Integrin a6 chain,, VLA-6 alpha chain, platelet gpIc | ITGA6 | 3655 |
| CD50 | ICAM-3, intercellular adhesion molecule 3 | ICAM3 | 3385 |
| CD51 | Integrin alpha chain, Vitronectin receptor a chain | ITGAV | 3685 |
| CD52 | Campath-1, HE5 | CDW52 | 1043 |
| CD53 | MRC OX-44 | CD53 | 963 |
| CD54 | ICAM-1, intercellular adhesion molecule 1 | ICAM1 | 3383 |
| CD55 | DAF, Decay Accelerating Factor | DAF | 1604 |
| CD56 | NKHI, Neural cell adhesion molecule (NCAM) | NCAM1 | 4684 |
| CD57 | HNK1 | CD57 | 964 |
| CD58 | LFA-3, lymphocyte function associated antigen-3 | CD58 | 965 |
| CD59 | MACIF, MIRL, P-18, protectin | CD59 | 966 |
| CD60 | GD3(CD60a), 9-0-acetyl GD3 (CD60b), 7-0-acetyl GD3 (CD60c) | | carbohydrate antigen |
| CD61 | Glycoprotein IIIa, beta3 integrin | ITGB3 | 3690 |
| CD62E | E-selectin, LECAM-2, ELAM-1 | SELE | 6401 |
| CD62L | L-selectin, LAM-1, Mel-14 | SELL | 6402 |
| CD62P | P-selectin, granule membrane protein-140 (GMP-140) | SELP | 6403 |
| CD63 | LIMP, gp55, LAMP-3 neuroglandular antigen, granulophysin | CD63 | 967 |
| CD64 | FcgR1, FcgammaR1 | FCGR1A | 2209 |
| CD65 | Ceramide dodecasaccharide 4c, VIM2 | | carbohydrate antigen |
| CD65s | Sialylated-CD65, VIM2 Antigen | | carbohydrate antigen |
| CD66a | BGP, carcinoembryonic antigen-related cell adhesion molecule 1 | CEACAM1 | 634 |
| CD66b | CGM6, NCA-95 | CEACAM8 | 1088 |
| CD66c | nonspecific crossreaction antigen, NCA-50/90 | CEACAM6 | 4680 |
| CD66d | CGM1 | CEACAM3 | 1084 |
| CD66e | CEA | CEACAM5 | 1048 |
| CD66f | PSG, Sp-1, pregnancy specific (b1) glycoprotein | PSG1 | 5669 |
| CD68 | gp110, macrosialin | CD68 | 968 |
| CD69 | AIM, activation inducer molecule, MLR3, EA1, VEA | CD69 | 969 |
| CD70 | CD27 ligand, KI-24 antigen | TNFSF7 | 970 |
| CD71 | Transferrin receptor | TFRC | 7037 |
| CD72 | Lyb-2, Ly-19.2, Ly32.2 | CD72 | 971 |
| CD73 | Ecto-5'-nucleotidase | NT5E | 4907 |
| CD74 | MHC Class II associated invariant chain (Ii) | CD74 | 972 |
| CD75 | Lactosamines | | carbohydrate antigen |
| CD75s | Alpha-2,6-sialylated lactosamines (formerly CDw75 and CDw76) | | carbohydrate antigen |
| CDw76 | Since HLDA7, CDw76 has been renamed CD75s | | carbohydrate antigen |
| CD77 | Pk blood group antigen; Burkitt's lymphoma associated antigen | | carbohydrate antigen |
| CD79a | MB-1; Iga | CD79A | 973 |
| CD79b | B29; Igβ | CD79B | 974 |
| CD80 | B7-1; BB1 | CD80 | 941 |
| CD81 | Target of an antiproliferative antibody (TAPA-1); M38 | CD81 | 975 |
| CD82 | R2; 4F9; C33; IA4, kangai 1 | KAI1 | 3732 |
| CD83 | HB15 | CD83 | 9308 |
| CD84 | p75, GR6 | CD84 | 8832 |
| CD85a | ILT5; LIR3; HL9 | LILRB3 | 11025 |
| CD85d | ILT4; LIR2; MIR10 | LILRB2 | 10288 |
| CD85k | ILT3; LIR5; HM18 | LILRB4 | 11006 |
| CD85j | LIR-1, ILT2 (immunoglobulin-like transcript 2); MIR7 | LILRB1 | 10859 |
| CD86 | B7-2; B70 | CD86 | 942 |
| CD87 | Urokinase plasminogen activator-receptor (uPA-R) | PLAUR | 5329 |
| CD88 | C5a-receptor | C5R1 | 728 |
| CD89 | Fca-receptor, IgA-receptor | FCAR | 2204 |
| CD90 | Thy-1 | THY1 | 7070 |
| CD91 | a2-macroglobulin receptor (ALPHA2M) | LRP1 | 4035 |
| CD92 | p70 | CDW92 | 23446 |
| CD93 | GR11 | | 23447 |
| CD94 | kP43, killer cell lectin-like receptor subfamily D, member 1 | KLRD1 | 3824 |
| CD95 | APO-1, Fas, TNFRSF6 | TNFRSF6 | 355 |
| CD96 | TACTILE (T cell activation increased late expression) | CD96 | 10225 |
| CD97 | BL-KDD/F12 | CD97 | 976 |
| CD98 | 4F2, FRP-1 | SLC3A2 | 6520 |
| CD99 | MIC2, E2 | CD99 | 4267 |
| CD100 | SEMA4D | SEMA4D | 10507 |
| CD101 | V7, P126 | IGSF2 | 9398 |
| CD102 | ICAM-2 | ICAM2 | 3384 |
| CD103 | Integrin alpha E subunit, HML-1 | ITGAE | 3682 |
| CD104 | Integrin beta 4 subunit, TSP-1180 | ITGB4 | 3691 |
| CD105 | Endoglin | ENG | 2022 |
| CD106 | VCAM-1 (vascular cell adhesion molecule-1), INCAM-110 | VCAM1 | 7412 |
| CD107a | Lysosomal associated membrane protein (LAMP)-1 | LAMP1 | 3916 |
| CD107b | Lysosomal associated membrane protein (LAMP)-2 | LAMP2 | 3920 |
| CD108 | GPI-gp80; John-Milton-Hagen (JMH) human blood group antigen | SEMA7A | 8482 |

TABLE 43-continued

Human CD Antigen Differentiation Molecules (as of November 2007).
List taken from: the url: hcdm.org/CD1toCD350.htm
downloaded on Nov. 6, 2007

| MOLECULE | | Gene Name | GeneID |
|---|---|---|---|
| CD109 | Platelet activation factor; 8A3, E123 | | N/A |
| CD110 | Thrombopoietin receptor; c-mpl | MPL | 4352 |
| CD111 | PRR1, Nectin 1, Hve C1, poliovirus receptor related 1 protein | PVRL1 | 5818 |
| CD112 | PRR2, Nectin 2, Hve B, poliovirus receptor related 2 protein | PVRL2 | 5819 |
| CD113 | PVRL3, Nectin3 | PVRL3 | 25945 |
| CD114 | G-CSFR, HG-CSFR, CSFR3 | CSF3R | 1441 |
| CD115 | M-CSFR, CSF-1, C-fms | CSF1R | 1436 |
| CD116 | GMCSF R alpha subunit, | CSF2RA | 1438 |
| CD117 | SCFR, c-kit, stem cell factor receptor | KIT | 3815 |
| CD118 | LIFR | LIFR | 3977 |
| CD119 | IFN gamma receptor alpha chain | IFNGR1 | 3459 |
| CD120a | TNFRI; TNFRp55 | TNFRSF1A | 7132 |
| CD120b | TNFRII; TNFRp75 | TNFRSF1B | 7133 |
| CD121a | Type I IL-1 receptor | IL1R1 | 3554 |
| CD121b | Type II IL-1 receptor | IL1R2 | 7850 |
| CD122 | IL-2 receptor betachain, p75 | IL2RB | 3560 |
| CD123 | Interleukin-3 receptor alpha chain (IL-3Ra) | IL3RA | 3563 |
| CD124 | IL-4 R alpha chain | IL4R | 3566 |
| CD125 | Interleukin-5 receptor a chain | IL5RA | 3568 |
| CD126 | IL-6 receptor alpha chain | IL6R | 3570 |
| CD127 | IL-7 receptor alpha chain, p90 | IL7R | 3575 |
| (CD129) | IL-9 receptor alpha chain | IL9R | 3581 |
| CD130 | gp130 | IL6ST | 3572 |
| CD131 | Common β chain, low-affinity (granulocyte-macrophage) | CSF2RB | 1439 |
| CD132 | Common gamma chain, interleukin 2 receptor, gamma | IL2RG | 3561 |
| CD133 | AC133, PROML1, prominin 1 | PROM1 | 8842 |
| CD134 | OX 40, TNFRSF4 | TNFRSF4 | 7293 |
| CD135 | FLT3, STK-1, flk-2 | FLT3 | 2322 |
| CD136 | Macrophage stimulating protein receptor, MSP-R, RON | MST1R | 4486 |
| CD137 | 4-1BB, Induced by lymphocyte activation (ILA) | TNFRSF9 | 3604 |
| CD138 | Syndecan-1, B-B4 | SDC1 | 6382 |
| CD139 | | | 23448 |
| CD140a | a-platelet derived growth factor (PDGF) receptor | PDGFRA | 5156 |
| CD140b | b-platelet derived growth factor (PDGF) receptor | PDGFRB | 5159 |
| CD141 | Thrombomodulin (TM), fetomodulin | THBD | 7056 |
| CD142 | Tissue factor, thromboplastin, coagulation factor III | F3 | 2152 |
| CD143 | Angiotensin-converting enzyme (ACE), peptidyl dipeptidase A | ACE | 1636 |
| CD144 | VE-cadherin, cadherin-5 | CDH5 | 1003 |
| CDw145 | None | | N/A |
| CD146 | Muc 18, MCAM, Mel-CAM, s-endo | MCAM | 4162 |
| CD147 | Basigin, M6, extracellular metalloproteinase inducer (EMMPRIN) | BSG | 682 |
| CD148 | DEP-1, HPTP-n, protein tyrosine phosphatase, receptor type, J | PTPRJ | 5795 |
| CD150 | SLAM, signalling lymphocyte activation molecule, IPO-3 | SLAMF1 | 6504 |
| CD151 | Platelet-endothelial tetra-span antigen (PETA)-3 | CD151 | 977 |
| CD152 | Cytotoxic T lymphocyte antigen (CTLA)-4 | CTLA4 | 1493 |
| CD153 | CD30 Ligand | TNFSF8 | 944 |
| CD154 | CD40 Ligand; TRAP (TNF-related activation protein)-1; T-BAM | TNFSF5 | 959 |
| CD155 | Polio virus receptor (PVR) | PVR | 5817 |
| CD156a | ADAM-8, a disintegrin and metalloproteinase domain 8 | ADAM8 | 101 |
| CD156b | TACE, ADAM 17 snake venom like protease CSVP | ADAM17 | 6868 |
| CD156C | ADAM10 | ADAM10 | 102 |
| CD157 | BST-1 BP-3/IF7 Mo5 | BST1 | 683 |
| CD158e1/2 | killer cell Ig-like receptor, three domains, long cytoplasmic tail, 1 | KIR3DL1 | 3811 |
| CD158i | killer cell Ig-like receptor, two domains, short cytoplasmic tail, 4 | KIR2DS4 | 3809 |
| CD158k | killer cell Ig-like receptor, two domains, long cytoplasmic tail, 2 | KIR2DL2 | 3803 |
| CD159a | killer cell lectin-like receptor subfamily C, member 1 | KLRC1 | 3821 |
| CD159c | NKG2C | KLRC2 | 3822 |
| CD160 | BY55, NK1, NK28 | CD160 | 11126 |
| CD161 | NKR-P1A, killer cell lectin-like receptor subfamily B, member 1 | KLRB1 | 3820 |
| CD162 | P selectin glycoprotein ligand 1, PSGL-1 | SELPLG | 6404 |
| CD162R | PEN5 | | see CD162 |
| CD163 | GHI/61, D11, RM3/1, M130 | CD163 | 9332 |
| CD164 | MUC-24, MGC 24, multi-glycosylated core protein 24 | CD164 | 8763 |
| CD165 | AD2, gp 37 | | 23449 |
| CD166 | ALCAM, KG-CAM, activated leukocyte cell adhesion molecule | ALCAM | 214 |
| CD167 | Discoidin receptor DDR1 (CD 167a) and DDR2 (CD 167b) | DDR1 | 780 |
| CD168 | RHAMM (receptor for hyaluronan involved in migration & motility) | HMMR | 3161 |
| CD169 | Sialodhesin, Siglec-1 | SN | 6614 |
| CD170 | Siglec 5 (sialic acid binding Ig-like lectin 5) | SIGLEC5 | 8778 |
| CD171 | Neuronal adhesion molecule, LI | L1CAM | 3897 |
| CD172a | SIRPa, signal inhibitory regulatory protein family member | PTPNS1 | 140885 |
| CD172b | SIRPbeta | SIRPB1 | 10326 |
| CD172g | SIRPgamma | SIRPB2 | 55423 |
| CD173 | Blood Group H2 | | carbohydrate antigen |
| CD174 | Lewis Y blood group, LeY, fucosyltransferase 3 | FUT3 | 2525 |
| CD175 | Tn Antigen (T-antigen novelle) | | carbohydrate antigen |
| CD175s | Sialyl-Tn | | carbohydrate antigen |
| CD176 | Thomsen-Friedenreich antigen (TF) | | carbohydrate antigen |
| CD177 | NB 1 | | None assigned |
| CD178 | FAS ligand, CD95 ligand | TNFSF6 | 356 |
| CD179a | V pre beta | VPREB1 | 7441 |
| CD179b | Lambda 5 | IGLL1 | 3543 |
| CD180 | RP105, Bgp95 | LY64 | 4064 |
| CD181 | CXCR1, (was CDw128A) | IL8RA | 3577 |
| CD182 | CXCR2, (was CDw128B) | IL8RB | 3579 |

TABLE 43-continued

Human CD Antigen Differentiation Molecules (as of November 2007).
List taken from: the url: hcdm.org/CD1toCD350.htm
downloaded on Nov. 6, 2007

| MOLECULE | | Gene Name | GeneID |
|---|---|---|---|
| CD183 | CXCR3 chemokine receptor, G protein-coupled receptor 9 | CXCR3 | 2833 |
| CD184 | CXCR4 chemokine receptor, Fusin | CXCR4 | 7852 |
| CD185 | CXCR5 | BLR1 | 643 |
| CD186 | CXCR6 | CXCR6 | 10663 |
| CD191 | CCR1 | CCR1 | 1230 |
| CD192 | CCR2 | CCR2 | 1231 |
| CD193 | CCR3 | CCR3 | 1232 |
| CD194 | CCR4 | CCR4 | 1233 |
| CD195 | CCR5 chemokine receptor | CCR5 | 1234 |
| CD196 | CCR6 | CCR6 | 1235 |
| CD197 | CCR7 | CCR7 | 1236 |
| CDw198 | CCR8 | CCR8 | 1237 |
| CDw199 | CCR9 | CCR9 | 10803 |
| CD200 | MRC OX 2 | CD200 | 4345 |
| CD201 | Endothelial protein C receptor (EPCR) | PROCR | 10544 |
| CD202b | TIE2, TEK | TEK | 7010 |
| CD203c | E-NPP3, PDNP3, PD-1beta | ENPP3 | 5169 |
| CD204 | MSR, SRA, Macrophage scavenger receptor | MSR1 | 4481 |
| CD205 | DEC-205 | LY75 | 4065 |
| CD206 | Macrophage mannose receptor (MMR) | MRC1 | 4360 |
| CD207 | Langerin | CD207 | 50489 |
| CD208 | DC-LAMP | LAMP3 | 27074 |
| CD209 | DC-SIGN | CD209 | 30835 |
| CDw210 | IL-10 receptor | IL10RA | 3587 |
|  |  | IL10RB | 3588 |
| CD212 | IL-12 receptor beta chain | IL12RB1 | 3594 |
| CD213a1 | IL-13 receptor alpha 1 | IL13RA1 | 3597 |
| CD213a2 | IL-13 R alpha 2 | IL13RA2 | 3598 |
| CD217 | IL-17 receptor | IL17R | 23765 |
| CD218a | IL18Ralpha | IL18R1 | 8809 |
| CD218b | IL18Rbeta | IL18RAP | 8807 |
| CD220 | Insulin Receptor | INSR | 3643 |
| CD221 | IGF I Receptor, type I IGF receptor | IGF1R | 3480 |
| CD222 | Mannose-6-phosphate receptor, insulin like growth factor II R | IGF2R | 3482 |
| CD223 | LAG-3 (Lymphocyte activation gene 3) | LAG3 | 3902 |
| CD224 | Gamma-glutamyl transferase, GGT | GGT1 | 2678 |
| CD225 | Leu-13, interferon-induced transmembrane protein 1 |  | 8519 |
| CD226 | DNAM-1, DTA-1 | CD226 | 10666 |
| CD227 | MUC 1 | MUC1 | 4582 |
| CD228 | Melanotransferrin, p97 | MFI2 | 4241 |
| CD229 | Ly9 | LY9 | 4063 |
| CD230 | Prion protein, PrPI, PrP(sc) abnormal form | PRNP | 5621 |
| CD231 | TALLA-1, TM4SF2 | TM4SF2 | 7102 |
| CD232 | VESPR | PLXNC1 | 10154 |
| CD233 | Band 3, AE1, anionexchanger 1, Diego blood group antigen | SLC4A1 | 6521 |
| CD234 | DARC, Fy-glycoprotein, Duffy blood group antigen | FY | 2532 |
| CD235a | Glycophorin A | GYPA | 2993 |
| CD235b | Glycophorin B | GYPB | 2994 |
| CD236 | Glycophorin C/D | GYPC | 2995 |
| CD236R | Glycophorin C | GYPC | 2995 |
| CD238 | Kell blood group antigen | KEL | 3792 |
| CD239 | B-CAM, utheran glycoprotein | LU | 4059 |
| CD240CE | Rh blood group system, Rh30CE | RHCE | 6006 |
| CD240D | Rh blood group system, Rh30D | RHD | 6007 |
| CD240DCE | Rh30D/CE crossreactive mabs |  | CD240CE, CD240D |

TABLE 43-continued

Human CD Antigen Differentiation Molecules (as of November 2007).
List taken from: the url: hcdm.org/CD1toCD350.htm
downloaded on Nov. 6, 2007

| MOLECULE | | Gene Name | GeneID |
|---|---|---|---|
| CD241 | RhAg, Rh50, Rh associated antigen | RHAG | 6005 |
| CD242 | LW blood group, Landsteiner-Wiener blood group antigens | ICAM4 | 3386 |
| CD243 | MDR-1, P-glycoprotein, pgp 170, multidrug resistance protein I | ABCB1 | 5243 |
| CD244 | 2B4 | CD244 | 51744 |
| CD245 | p220/240, DY12, DY35 |  | N/A |
| CD246 | Anaplastic lymphoma kinase (ALK) | ALK | 238 |
| CD247 | T cell receptor zeta chain, CD3 zeta | CD3Z | 919 |
| CD248 | TEM1, Endosialin | CD164L1 | 57124 |
| CD249 | Aminopeptidase A | ENPEP | 2028 |
| CD252 | OX40L | TNFSF4 | 7292 |
| CD253 | TRAIL | TNFSF10 | 8743 |
| CD254 | TRANCE | TNFSF11 | 8600 |
| CD256 | APRIL | TNFSF13 | 8741 |
| CD257 | BLYS | TNFSF13B | 10673 |
| CD258 | LIGHT | TNFSF14 | 8740 |
| CD261 | TRAIL-R1 | TNFRSF10A | 8797 |
| CD262 | TRAIL-R2 | TNFRSF10B | 8795 |
| CD263 | TRAIL-R3 | TNFRSF10C | 8794 |
| CD264 | TRAIL-R4 | TNFRSF10D | 8793 |
| CD265 | TRANCE-R | TNFRSF11A | 8792 |
| CD266 | TWEAK-R | TNFRSF12A | 51330 |
| CD267 | TACI | TNFRSF13B | 23495 |
| CD268 | BAFFR | TNFRSF13C | 115650 |
| CD269 | BCMA | TNFRSF17 | 608 |
| CD271 | NGFR (p75) | NGFR | 4804 |
| CD272 | BTLA | BTLA | 151888 |
| CD273 | B7DC, PDL2 | PDCD1LG2 | 80380 |
| CD274 | B7H1, PDL1 | PDCD1LG1 | 29126 |
| CD275 | B7H2, ICOSL | ICOSL | 23308 |
| CD276 | B7H3 | N/A | 80381 |
| CD277 | BT3.1 | BTN3A1 | 11119 |
| CD278 | ICOS | ICOS | 29851 |
| CD279 | PD1 | PDCD1 | 5133 |
| CD280 | ENDO180 | MRC2 | 9902 |
| CD281 | TLR1 | TLR1 | 7096 |
| CD282 | TLR2 | TLR2 | 7097 |
| CD283 | TLR3 | TLR3 | 7098 |
| CD284 | TLR4 | TLR4 | 7099 |
| CD286 | TLR6 | TLR6 | 10333 |
| CD288 | TLR8 | TLR8 | 51311 |
| CD289 | TLR9 | TLR9 | 54106 |
| CD290 | TLR10 | TLR10 | 81793 |
| CD292 | BMPR1A | BMPR1A | 657 |
| CDw293 | BMPR1B | BMPR1B | 658 |
| CD294 | CRTH2 | GPR44 | 11251 |
| CD295 | LeptinR | LEPR | 3953 |
| CD296 | ART1 | ART1 | 417 |
| CD297 | ART4 | DO | 420 |
| CD298 | Na+/K+-ATPase β3 | ATP1B3 | 483 |
| CD299 | DCSIGN-related | CD209L | 10332 |
| CD300a | CMRF35H |  | 11314 |
| CD300c | CMRF35A |  | 10871 |
| CD300e | CMRF35L1 |  |  |
| CD301 | MGL, CLECSF14 | CLECSF14 | 10462 |
| CD302 | DCL1 | N/A | 9936 |
| CD303 | BDCA2 | CLECSF7 | 170482 |
| CD304 | BDCA4, Neuropilin 1 | NRP1 | 8829 |
| CD305 | LAIR1 | LAIR1 | 3903 |
| CD306 | LAIR2 | LAIR2 | 3904 |
| CD307 | IRTA2 | N/A | 83416 |
| CD309 | VEGFR2, KDR | KDR | 3791 |
| CD312 | EMR2 | EMR2 | 30817 |
| CD314 | NKG2D | KLRK1 | 22914 |
| CD315 | CD9P1 | PTGFRN | 5738 |
| CD316 | EWI2 | IGSF8 | 93185 |
| CD317 | BST2 | BST2 | 684 |
| CD318 | CDCP1 | N/A | 64866 |

TABLE 43-continued

Human CD Antigen Differentiation Molecules (as of November 2007). List taken from: the url: hcdm.org/CD1toCD350.htm downloaded on Nov. 6, 2007

| MOLECULE | | Gene Name | GeneID |
|---|---|---|---|
| CD319 | CRACC | SLAMF7 | 57823 |
| CD320 | 8D6A | N/A | 51293 |
| CD321 | JAM1 | F11R | 50848 |
| CD322 | JAM2 | JAM2 | 58494 |
| CD324 | E-Cadherin | CDH1 | 999 |
| CD325 | N-Cadherin | CDH2 | 1000 |
| CD326 | Ep-CAM | TACSTD1 | 4072 |
| CD327 | siglec6 | SIGLEC6 | 946 |
| CD328 | siglec7 | SIGLEC7 | 27036 |
| CD329 | siglec9 | SIGLEC9 | 27180 |
| CD331 | FGFR1 | FGFR1 | 2260 |
| CD332 | FGFR2 | FGFR2 | 2263 |
| CD333 | FGFR3 | FGFR3 | 2261 |
| CD334 | FGFR4 | FGFR4 | 2264 |
| CD335 | NKp46 | NCR1 | 9437 |
| CD336 | NKp44 | NCR2 | 9436 |
| CD337 | NKp30 | NCR3 | 259197 |
| CD338 | ABCG2, BCRP | ABCG2 | 9429 |
| CD339 | Jagged-1 | JAG1 | 182 |
| CD340 | Her-2 | ERBB2 | 2064 |
| CD344 | Frizzled-4 | FZD4 | 8322 |
| CD349 | Frizzled-9 | FZD9 | 8326 |
| CD350 | Frizzled-10 | FZD10 | 11211 |

TABLE 44

| sCD ANTIGEN SPECIFICITIES (1) sCD Specificities Gentel | sCD ANTIGEN NAME Name |
|---|---|
| CD14 | LPS-R (LPS Receptor) |
| CD23 | FceRII (low affinity IgE receptor) |
| CD25 | IL2-R-alpha chain, Tac antigen |
| CD26 | gp120, Ta1 |
| CD27 | T14 (Integrin beta 2), S152 |
| CD30 | Ki-1 antigen, B4, Ber-H2 antigen |
| CD32b/c | FcGRII, B1, gp40 |
| CD40 | TNF Receptor-5, Bp50 |
| CD54 | ICAM-1 (intercellular adhesion molecule 1) |
| CD62E | E-selectin (ELAM-1) |
| CD62L | L-selectin (LAM-1) |
| CD80 | B7-1, BB1 |
| CD86 | B7-2, B70 |
| CD87 | Urokinase plasminogen activator R (uPA-R) |
| CD95 | Fas, (APO-1), TNFRSF6 |
| CD102 | ICAM-2 |
| CD105 | Endoglin |
| CD106 | VCAM-1 |
| CD114 | G-CSFR |
| CD115 | M-CSFR, C-fms |
| CD117 | c-kit, stem cell factor receptor |
| CD120a | TNFR-I |
| CD120b | TNFR-II |
| CD121b | IL-1 R 2 (type II IL-1 receptor) |
| CD124 | IL-4 R alpha chain |
| CD126 | IL-6 R alpha chain |
| CD127 | IL-7 R alpha chain |
| CD130 | gp130 |
| CD132 | Il-2 R gamma |
| CD152 | |
| CD166 | ALCAM (activated leukocyte cell adhesion molecule) |
| CD170 | Siglec 5 (sialic acid binding Ig-like lectin 5) |
| CD178 | Fas ligand |
| CD213a1 | IL-13 R alpha 1 |
| CD213a2 | IL-13 R alpha 2 |
| CD221 | IGF1R (IgF1 receptor) |
| CD239 | B-CAM (utheran glycoprotein) |
| CD258 | LIGHT |
| CD263 | TRAIL-R3 |

TABLE 44-continued

| sCD ANTIGEN SPECIFICITIES (1) sCD Specificities Gentel | sCD ANTIGEN NAME Name |
|---|---|
| CD309 | VEGFR2, KDR |
| CD324 | E-Cadherin |
| CDw329 | Siglec9 |

TABLE 45

| sCD Marker ID | Identity |
|---|---|
| CD11b | Integrin α M |
| CD11c | Integrin α X |
| CD13 | Aminopeptidase N |
| CD15 | LEWIS x |
| CD33 | Siglec-3 |
| CD36 | SR-B3 |
| CD64 | Fc gamma RI |
| CD49d | Integrin α 4 |
| CD29 | Integrin β 1 |
| CD38 | CD38 |
| CD71 | Transferrin |
| CD4 | T4 |
| CD34 | gp105 |
| CD9 | p24 |
| CD41 | Integrin α 2B |
| CD43 | sialophorin |
| CD45 | LCA |
| CD4 | L3T4 |
| CD200 | OX2 |
| CD31 | sPECAM1 |
| CD55 | DAF |
| CD56 | NCAM-1 |
| CD66a | CEACAM-1 |
| CD64 | Fc gamma RI |
| CD83 | HB15 |
| CD85d | ILT4 |
| CD85j | ILT2 |
| CD97 | CD97 |
| CD147 | EMMPRIN |
| CD202b | Tie-2 |
| CD212b1 | IL-12 Rβ1 |
| CD212b2 | IL-12 Rβ2 |
| CDw217 | IL-17R |
| CD217 | IL-17 |
| CD217F | IL-17F |
| CD217E | IL-17E |
| CD217D | IL-17D |
| CD217C | IL-17C |
| CD217B/r | IL-17B R |
| CD217B | IL-17B |
| CD217rD | IL-17 RD |
| CD222 | ILF2 R |
| CD226 | DNAM-1 |
| CD244 | 2B4/SLAMF4 |
| CD235a | Glycophorin A |
| CD44 | H-Cam |
| CD90 | Thy-1 |
| CD116 | GM-CSFR |
| CD123 | IL-3Ralpha |
| CD46 | MCP |
| CD16 | FcgammaRIIIA |
| CD35 | CR1 |
| CD8 (alpha) | T8 |
| CD1c | R7 |
| CD20 | MS4A1 |
| CD19 | B4 |
| CD7 | gp40 |
| CD1a | R4 |
| CD1d | R3 |
| CD2 | T11 |
| CD10 | Neprilysin |
| CD40L | CD40L |
| CD62P | Selectin-P |
| CD110 | Thrombopoietin |

TABLE 45-continued

| sCD Marker ID | Identity |
| --- | --- |
| CD129 | CD129 |
| CD137 | 4-1BB |
| CD143 | ACE |
| CD148 | DEP-1 |
| CD156b | TACE |
| CD171 | L1CAM |
| CD195 | CCR5 |
| CD220 | Insulin Rec. |
| CD264 | TRAIL R4 |

TABLE 46

Detector Antibodies

| ID | Vendor | Description | Catalogue # |
| --- | --- | --- | --- |
| CD116 | Apollo | Human GM-CSF R alpha hcx ™, Fc Chimera | 1102H |
| CD11b | Spring Bioscience | Human CD11b, aa 936-1154 | P7868 |
| CD11c | Abnova | Human ITGAX Partial, GST Conjugated/Tagged | H00003687-Q01 |
| CD123 | R&D Systems | Recombinant Human IL-3 sR alpha, CF | 301-R3-025/CF |
| CD13 | R&D Systems | Recombinant Human Aminopeptidase N/ANPEP, CF | 3815-ZN-010 |
| CD137L | MBL | Mouse Anti-Human CD137L/41BBL Monoclonal Antibody, Unconjugated, Clone 5F4 | K0030-3 |
| CD147 | R&D Systems | Recombinant Human EMMPRIN/Fc Chimera (NS0-expressed), CF 9 | 972-EMN-050 |
| CD16 | R&D Systems | Recombinant Human Fc gamma RIIIB/CD16b, CF | 1597-FC-050/CF |
| CD19 | Novus | Human CD19 Partial, GST Conjugated/Tagged | H00000930-Q01 |
| CD195 | ProSpec | CCR5 Protein | 1112P |
| CD1a | Raybiotech | Recombinant Human CD1a | IP-03-467 |
| CD1C | Novus | Human CD1C Partial, GST Conjugated/Tagged | H00000911-Q01 |
| CD1d | Novus | CA1d Full Length Recombinant - GST/Tagged | H00000912-P01 |
| CD2 | Raybiotech | Recombinant Human CD2 | IP-03-468 |
| CD20 | Novus | Human MS4A1 Full length, GST Conjugated/Tagged | H00000931-P01 |
| CD200 | R&D Systems | Recombinant Human CD200/Fc Chimera, CF | 627-CD-100 |
| CD202b | R&D Systems | Recombinant Mouse Tie-2/Fc Chimera, CF | 313-TI-100 |
| CD212b1 | R&D Systems | Recombinant Human IL-12 R beta 1/Fc Chimera, CF | 839-B1-100 |
| CD212b2 | R&D Systems | Recombinant Human IL-12 R beta 1/Fc Chimera, CF | 1959-B2-050 |
| CD217 | R&D Systems | Recombinant Human IL-17, CF | 317-IL-050 |
| CD217B | R&D Systems | Recombinant Human IL-17B, CF | 1248-IB-025 |
| CD217B/r | R&D Systems | Recombinant Human IL-17B R/Fc Chimera, CF | 1207-BR-050 |
| CD217C | R&D Systems | Recombinant Human IL-17C, CF | 1234-IL-025 |
| CD217D | R&D Systems | Recombinant Human IL-17D, CF | 1504-IL-025 |
| CD217E | R&D Systems | Recombinant Human IL-17E, CF | 1258-IL-025 |
| CD217F | R&D Systems | Recombinant Human IL-17F, CF | 1335-IL-025 |
| CD217rD | R&D Systems | Recombinant Human IL-17 RD/SEF | 2275-IL-050 |
| CD222 | R&D Systems | Recombinant Human IGF-II R, CF | 2447-GR-050 |
| CD226 | R&D Systems | Recombinant Human DNAM-1/Fc Chimera, CF | 666-DN-050 |
| CD235a | Sigma | Glycophorin Predominantly glycophorin A from blood type MN | G5017 |
| CD235a | Sigma | Glycophorin Predominantly glycophorin A from blood type MM | G7903 |
| CD244 | R&D Systems | Recombinant Human 2B4/CD244/SLAMF4/Fc Chimera, CF | 1039-2B-050 |
| CD29 | Spring Bioscience | Human CD29, aa 579-799 from Spring Bioscience | P7892 |
| CD31 | Raybiotech | Recombinant Human CD31 | IP-03-471 |
| CD33 | R&D Systems | Recombinant Human Siglec-3/CD33/Fc Chimera, CF | 1137-SL-050 |
| CD34 | Spring Bioscience | Human CD34 Full-Length | P7122 |
| CD35 | Anaspec | Cripto-1, CR-1 | 60630 |
| CD36 | R&D Systems | Recombinant Human CD36/SR-B3/Fc Chimera, CF | 1955-CD-050 |
| CD38 | R&D Systems | Recombinant Human CD38, CF | 2404-AC-010 |
| CD4 | R&D Systems | Recombinant Human sCD4, CF | 514-CD-050/CF |
| CD41 | BACHEM | Human CD41 | H-3032.0005 |
| CD43 | Spring Bioscience | Human CD43, aa 271-401 | P7896 |
| CD44H | R&D Systems | Recombinant Human CD44/Fc Chimera, CF | 3660-CD-050 |
| CD45 | Calbiochem | Human Protein Tyrosine Phosphatase CD45 | 217614-20ug |
| CD46 | Santa Cruz | CD46 | sc4530 |
| CD49d | Novus (Abnova) | Human ITGA4 Partial, GST Conjugated/Tagged | H00003676-Q01 |
| CD55 | R&D Systems | Recombinant Human CD55/DAF, CF | 2009-CD-050 |
| CD56 | R&D Systems | Recombinant Human NCAM-1/CD56, CF | 2408-NC-050 |
| CD64 | R&D Systems | Recombinant Human Fc gamma RIA/CD64, CF | 1257-FC-050 |
| CD66a | R&D Systems | Recombinant Human CEACAM-1/CD66a, CF | 2244-CM-050 |
| CD7 | Spring | Human CD7 Full-Length | P7841 |
| CD71 | Raybiotech | Human CD71, aa 461-760 | DS-01-0048 |
| CD8 (alpha) | Santa Cruz | Human CD8alpha | sc-4265 |
| CD83 | R&D Systems | Recombinant Human CD83/Fc Chimera, CF | 2044-CD-050 |
| CD85d | R&D Systems | Recombinant Human ILT4/CD85d/Fc Chimera, CF | 2078-T4-050 |
| CD85j | R&D Systems | Recombinant Human ILT2/CD85j/Fc Chimera, CF | 2017-T2-050 |
| CD9 | Spring Bioscience | Human CD9 Full-Length | P7878 |
| CD90 | Novus | Human THY1 Full length, GST Conjugated/Tagged | H00007070-P01 |
| CD97 | R&D Systems | Recombinant Human CD97, CF | 2529-CD-050 |
| CDw217 | R&D Systems | Recombinant Human IL-17 R/Fc Chimera, CF | 177-IR-100 |

TABLE 46-continued

Detector Antibodies

| ID | Vendor | Description | Catalogue # |
|---|---|---|---|
| CD138 | Cell Sciences | Human SYNDECAN-1/CD138 ELISA Kit, DIACLONE | 850.640.096 |
| CD141 | R&D Systems | Recombinant Human Thrombomodulin/CD141, CF | 3947-PA-010 |
| CD50 | R&D Systems (Matched Set) | Recombinant Human ICAM-3/CD50/Fc Chimera, | 715-IC-050 |
| CD52 | Raybiotech | Human CD52 | IP-03-487P |
| CD70 | R&D Systems | Mouse CD27 Ligand/TNFSF7, Unconjugated | 783-CL-050 |
| CD171 | Novus | L1CAM-L1 Human Recombinant Protein | H00003897-Q01 |
| HLA A | Abnova | Human HLA-A Protein Full-Length, GST Conjugated/Tagged | H00003105-P01 |
| CD170 | R&D Systems | Recombinant Human Protein Siglec 5 | 1072-SL-050 |
| CD10 | R&D Systems | Recombinant Human Neprilysin, CF | 1182-ZN-010 |
| CD102 | R&D Systems | Recombinant Human ICAM-2/CD102/Fc Chimera, CF | 803-I2-050 |
| CD105 | R&D Systems | Recombinant Human Endoglin/CD105 | 1097-EN-025 |
| CD106 | R&D Systems | Recombinant Human VCAM-1/CD106, CF | 809-VR-050 |
| CD110 | R&D Systems | Recombinant Human Thrombopoietin R/Fc Chimera, CF | 1016-TR-050 |
| CD114 | R&D Systems | Recombinant Human G-CSF sR/CD114 | 381-GR-050/CF |
| CD115 | R&D Systems | Recombinant Human M-CSF R/Fc Chimera | 329-MR-100 |
| CD117 | R&D Systems | Recombinant Human SCF sR/c-kit | 332-SR-050 |
| CD120a | R&D Systems | Recombinant Human sTNF RI/TNFRSF1A | 636-R1-025 |
| CD120b | R&D Systems | Recombinant Human TNF RII/TNFRSF1B (aa 24-206) | 1089-R2-025 |
| CD121a | R&D Systems | Recombinant Human IL-1 sRI | 269-1R-100 |
| CD121b | R&D Systems | Recombinant Human IL-1 sRII | 263-2R-050 |
| CD124 | R&D Systems | Recombinant Human IL-4 sR | 230-4R-025/CF |
| CD125 | R&D Systems | Recombinant Human IL-5 sR alpha | 253-5R-025 |
| CD126 | R&D Systems | Recombinant Human IL-6 sR | 227-SR-025 |
| CD127 | R&D Systems | Recombinant Human IL-7 R alpha/Fc Chimera, CF | 306-IR-050 |
| CD129 | R&D Systems | Recombinant Human IL-9 sR (NS0-expressed) | 290-RNS-025 |
| CD130 | R&D Systems | Recombinant Human sgp130 | 228-GP-010 |
| CD132 | R&D Systems | Recombinant Human Common gamma Chain | 384-RG-050 |
| CD137 | R&D Systems | Recombinant Human 4-1BB/TNFRSF9/Fc Chimera, CF | 838-4B-100 |
| CD14 | R&D Systems | Recombinant Human CD14 | 383-CD-050 |
| CD143 | R&D Systems | Recombinant Human ACE, CF | 929-ZN-0101 |
| CD148 | R&D Systems | Recombinant Human DEP-1/CD148 (aa 997-1337), CF | 1934-DP-010 |
| CD152 | R&D Systems | Recombinant Human CTLA-4/Fc Chimera | 325-CT-200 |
| CD156b | R&D Systems | Recombinant Human TACE/ADAM17, CF | 930-ACB-010 |
| CD166 | R&D Systems | Recombinant Human ALCAM/Fc Chimera, CF | 656-AL-100 |
| CD171 | R&D Systems | Recombinant Human NCAM-L1/Fc Chimera, CF | 777-NC-100 |
| CD178 | R&D Systems | Recombinant Human Fas Ligand/TNFSF6 | 126-FL-010 |
| CD195 | Assay Designs | Human CCR5, N-terminus | 908-132 |
| CD1d | BD Bio | Human CD1d:Ig | 557764 |
| CD2 | Spring Bio | Human CD2, aa25-209 | P3044 |
| CD213a1 | R&D Systems | Recombinant Human IL-13 R alpha 1/Fc Chimera, CF | 146-IR-100 |
| CD213a2 | R&D Systems | Recombinant Human IL-13 R alpha 2/Fc Chimera (NS0), CF | 614-INS-100 |
| CD220 | R&D Systems | Recombinant Human Insulin R/CD220 (aa 28-956) | 1544-IR-050 |
| CD221 | R&D Systems | Recombinant Human IGF-I sR, CF | 391-GR-050 |
| CD23 | R&D Systems | Recombinant Human Fc epsilon RII/CD23, CF | 123-FE-050 |
| CD239 | R&D Systems | Recombinant Human BCAM/Fc Chimera, CF | 148-BC-100 |
| CD25 | R&D Systems | Recombinant Human IL-2 sR alpha | 223-2A-005 |
| CD258 | R&D Systems | Recombinant Human LIGHT/TNFSF14 | 664-LI-025 |
| CD26 | R&D Systems | Recombinant Human DPPIV/CD26, CF | 1180-SE-010 |
| CD263 | R&D Systems | Recombinant Human TRAIL R3/TNFRSF10C/Fc Chimera | 630-TR-100 |
| CD264 | R&D Systems | Recombinant Human TRAIL R4/TNFRSF10D/Fc Chimera, CF | 633-TR-100 |
| CD27 | R&D Systems | Recombinant Human CD27/TNFRSF7/Fc Chimera, CF | 382-CD-100 |
| CD28 | R&D Systems | Recombinant Human CD28/Fc Chimera, CF | 342-CD-200 |
| CD295 | R&D Systems | Recombinant Human Leptin R/Fc Chimera | 389-LR-100 |
| CD30 | R&D Systems | Human CD30/TNFRSF8 Recombinant Protein (Fc Chimera) (Carrier Free) | 813-CD-100 |
| CD309 | R&D Systems | Recombinant Human VEGF R2/KDR/Fc Chimera | 357-KD-050 |
| CD324 | R&D Systems | Recombinant Human E-Cadherin/Fc Chimera, CF | 648-EC-100 |
| CD32b/c | R&D Systems | Recombinant Human Fc gamma RIIB/C (CD32b/c), CF | 1875-CD-050 |
| CD33L2 | R&D Systems | Recombinant Siglec-5/Fc Chimera | 1072-SL |
| CD33L2 | R&D Systems | Recombinant Siglec-5/Fc Chimera | 1072-SL |
| CD40 | R&D Systems | Recombinant Human CD40/TNFRSF5/Fc Chimera, CF | 1493-CD-050 |
| CD40L | R&D Systems | Recombinant Human CD40 Ligand/TNFSF5 (aa 108-261) | 617-CL-050 |
| CD50 | R&D Systems | Recombinant Human ICAM-3/CD50/Fc Chimera, CF | 715-IC-050 |
| CD54 | R&D Systems | Recombinant Human ICAM-1/CD54, CF | ADP4-050 |
| CD58 | R&D Systems | Recombinant Human CD58/LFA-3 | 1689-CD-050 |
| CD6 | R&D Systems | Recombinant Human CD6/Fc Chimera, CF | 627-CD-100 |

TABLE 46-continued

Detector Antibodies

| ID | Vendor | Description | Catalogue # |
|---|---|---|---|
| CD62E | R&D Systems | Recombinant Human E-Selectin/CD62E, CF | ADP1-050 |
| CD62L | R&D Systems | Recombinant Human L-Selectin/CD62L, CF | ADP2-050 |
| CD62P | R&D Systems | Recombinant Human P-Selectin/CD62P, CF | ADP3-050 |
| CD80 | R&D Systems | Recombinant Human B7-1/CD80/Fc Chimera, CF | 140-B1-100 |
| CD84 | R&D Systems | Recombinant Human CD84/SLAMF5 | 1855-CD-050 |
| CD86 | R&D Systems | Recombinant Human B7-2/CD86/Fc Chimera, CF | 141-B2-100 |
| CD87 | R&D Systems | Recombinant Human uPAR | 807-UK-100 |
| CD95 | R&D Systems | Recombinant Human Fas/TNFRSF6/Fc Chimera | 326-FS-050 |
| CDw329 | R&D Systems | Recombinant Human Siglec-9/Fc Chimera, CF | 1139-SL-050 |

TABLE 47

Capture Antibodies

| CD Marker ID | Vendor | Full Identity | Catalogue # |
|---|---|---|---|
| CD10 | R&D Systems | Human Neprilysin DuoSet | DY1182 |
| CD110 | Upstate | Rabbit Anti-TPO R/c-Mpl Polyclonal Antibody, Unconjugated | 06-944 |
| CD116 | R&D Systems | Human GM-CSF R alpha MAb (Clone 31916) | MAB706 |
| CD116 | Beckman | Purified anti-human CD116 | 305901 |
| CD11b | R&D Systems | Human Integrin alpha M/CD11b MAb (Clone 238439) | MAB16992 |
| CD11b | R&D Systems | Human Integrin alpha M/CD11b MAb (Clone 238446) | MAB16991 |
| CD11b | R&D Systems | Human Integrin alpha M/CD11b MAb (Clone ICRF44) | MAB1699 |
| CD11c | R&D Systems | Human Integrin alpha X/CD11c MAb (Clone ICRF 3.9) | MAB1777 |
| CD11c | BD | Mouse Anti-CD11c Monoclonal Antibody, Unconjugated, Clone B-ly6 | 555391 |
| CD123 | R&D Systems | Human IL-3 R alpha MAb (Clone 32703) | MAB301 |
| CD123 | Abcam | Mouse Anti-IL3RA Monoclonal Antibody, Unconjugated, Clone 6H6 | ab21562 |
| CD13 | Abcam | Mouse Anti-CD13 Monoclonal Antibody, Unconjugated, Clone 22A5 | ab20136 |
| CD13 | BD | Mouse Anti-CD13 Monoclonal Antibody, Unconjugated, Clone WM15 | 555393 |
| CD137 | R&D Systems | Human 4-1BB/TNFRSF9 DuoSet | DY838 |
| CD143 | R&D Systems | Human ACE DuoSet | DY929 |
| CD147 | R&D Systems | Human EMMPRIN MAb (Clone 109403) | MAB972 |
| CD147 | BD | Mouse Anti-CD147 Monoclonal Antibody, Unconjugated, Clone HIM6 | 555961 |
| CD156b | R&D Systems | Human TACE/ADAM17 DuoSet | DY930 |

TABLE 47-continued

Capture Antibodies

| CD Marker ID | Vendor | Full Identity | Catalogue # |
|---|---|---|---|
| CD16 | R&D Systems | Human Fc gamma RIIIA/B (CD16a/b) MAb (Clone 245536) | MAB2546 |
| CD16 | BD | Mouse Anti-CD16 Monoclonal Antibody, Unconjugated, Clone 3G8 | 556617 |
| CD171 | Abcam | Mouse Anti-L1CAM Monoclonal Antibody, Unconjugated, Clone UJ127.11 | ab20148 |
| CD171 | Abcam | Mouse Anti-L1CAM Monoclonal Antibody, Unconjugated, Clone UJ181.4 | ab20149 |
| CD171 | BD | Mouse Anti-CD171 Monoclonal Antibody, Unconjugated, Clone 5G3 | 554273 |
| CD19 | Abcam | Mouse Anti-CD19 Monoclonal Antibody, Unconjugated, Clone LT19 | ab212 |
| CD19 | Abcam | Mouse Anti-CD19 Monoclonal Antibody, Unconjugated, Clone MB19 | ab25177 |
| CD1A | Abcam | Mouse Anti-CD1 Monoclonal Antibody, Unconjugated, Clone NA1/34 | ab24055 |
| CD1A | Abcam | Mouse Anti-CD1 Monoclonal Antibody, Unconjugated, Clone RIV12 | ab23607 |
| CD1c | Abcam | Mouse Anti-CD1 Monoclonal Antibody, Unconjugated, Clone NA1/34 | ab24055 |
| CD1c | Abcam | Mouse Anti-CD1c Monoclonal Antibody, Unconjugated, Clone M241 | ab18216 |
| CD1d | Abcam | Mouse Anti-CD1d Monoclonal Antibody, Unconjugated, Clone NOR3.2 (NOR3.2/13.17) | ab11076 |
| CD1d | BD | Rat Anti-CD1d Monoclonal Antibody, Unconjugated, Clone 1B1 | 559438 |
| CD20 | R&D Systems | Human MS4A1/CD20 MAb (Clone 396444) | MAB4225 |
| CD20 | Abcam | Mouse Anti-CD20 Azide free Monoclonal Antibody, Unconjugated, Clone MEM-97 | ab46701 |
| CD200 | R&D Systems | Human CD200 MAb (Clone 325520) | MAB627 |
| CD200 | R&D Systems | Human CD200 MAb (Clone 325516) | MAB27241 |
| CD202b | R&D Systems | Human Tie-2 MAb (Clone 83711) | MAB313 |
| CD202b | R&D Systems | Human Tie-2 MAb (Clone 83715) | MAB3131 |
| CD212b1 | R&D Systems | Human IL-12 R beta 1 MAb (Clone 69310) | MAB839 |
| CD212b2 | R&D Systems | Human IL-12 R beta 1 MAb (Clone 69310) | MAB1959 |
| CD217 | R&D Systems | Human IL-17 DuoSet | DY317 |
| CD217B | R&D Systems | Human IL-17B MAb (Clone 174113) | MAB1248 |
| CD217B | R&D Systems | Goat Anti-Human IL-17B Polyclonal Antibody, Unconjugated | AF1248 |
| CD217B/r | R&D Systems | Human IL-17B R DuoSet | DY1207 |
| CD217C | R&D Systems | Human IL-17C MAb (Clone 177114) | MAB1234 |

TABLE 47-continued

Capture Antibodies

| CD Marker ID | Vendor | Full Identity | Catalogue # |
|---|---|---|---|
| CD217D | R&D Systems | Human IL-17D MAb (Clone 246002) | MAB1504 |
| CD217D | R&D Systems | Human IL-17D MAb (Clone 246018) | MAB15041 |
| CD217E | R&D Systems | Human IL-17E MAb (Clone 182203) | MAB1258 |
| CD217E | Cell Sciences | Rabbit Anti-Human IL-17E Antibody, Unconjugated | PA0694 |
| CD217F | R&D Systems | Human IL-17F MAb (Clone 197315) | MAB1335 |
| CD217F | Abcam | Rabbit Anti-Human IL-17F Polyclonal Antibody, Unconjugated | ab46000 |
| CD217rD | R&D Systems | Human IL-17 RD/SEF MAb (Clone 309539) | MAB2275 |
| CD220 | R&D Systems | Human Total Insulin R DuoSet IC, 2 Plate | DYC1544-2 |
| CD222 | R&D Systems | Human IGF-II R Affinity Purified Polyclonal Ab | AF2447 |
| CD222 | Abcam | Mouse Anti-IGF2 Receptor Monoclonal Antibody, Unconjugated, Clone MEM-238 | ab8093 |
| CD226 | R&D Systems | Human DNAM-1 MAb (Clone 102511) | MAB666 |
| CD226 | Abcam | Mouse Anti-CD226 Monoclonal Antibody, Unconjugated, Clone DX11 | ab24041 |
| CD235a | R&D Systems | Human Glycophorin A MAb (Clone R10) | MAB1228 |
| CD235a | Abcam | Mouse Anti-Human Glycophorin A Monoclonal Antibody, Unconjugated, Clone BRIC 256 | ab35760 |
| CD235a | Abcam | Mouse Anti-Glycophorin A Monoclonal Antibody, Unconjugated, Clone O.N.312 | ab14486 |
| CD244 | R&D Systems | Human 2B4/CD244/SLAMF4 MAb (Clone 146510) | MAB1039 |
| CD244 | BD | Mouse Anti-CD244 Monoclonal Antibody, Unconjugated, Clone 2-69 | 550814 |
| CD264 | R&D Systems | Human TRAIL sR4/TNFRSF10D DuoSet | DY633 |
| CD29 | R&D Systems | Human Integrin beta 1/CD29 MAb (Clone 4B7R) | MAB1778 |
| CD29 | R&D Systems | Human Integrin beta 1/CD29 MAb (Clone P4G11) | MAB17782 |
| CD31 | R&D Systems | Human CD31/PECAM-1 MAb (Clone 9G11) | BBA7 |
| CD31 | R&D Systems | Human CD31/PECAM-1 Affinity Purified Polyclonal Ab | AF806 |
| CD33 | R&D Systems | Human Siglec-3/CD33 MAb (Clone 6C5/2) | MAB1137 |
| CD34 | Abcam | Mouse Anti-CD34 Monoclonal Antibody, Unconjugated, Clone BI-3C5 | ab6330 |
| CD34 | BD | Mouse Anti-CD34 Monoclonal Antibody, Unconjugated, Clone 581 | 555820 |
| CD35 | Abcam | Mouse Anti-CD35 Monoclonal Antibody, Unconjugated, Clone E11 | ab25 |
| CD35 | Exalpha | Mouse Anti-CD35 | 351 |
| CD35 | Abcam | Mouse Anti-CD35 Monoclonal Antibody, Unconjugated, Clone E11 | ab25 |
| CD36 | R&D Systems | Human CD36/SR-B3 MAb (Clone 255606) | MAB19551 |
| CD36 | R&D Systems | Human CD36/SR-B3 MAb (Clone 255619) | MAB1955 |
| CD38 | R&D Systems | Human CD38 MAb (Clone 240726) | MAB24041 |
| CD38 | R&D Systems | Human CD38 MAb (Clone 240742) | MAB2404 |
| CD4 | R&D Systems | Human CD4 MAb (Clone 34930) | MAB379 |
| CD4 | R&D Systems | Human CD4 MAb (Clone 34915) | MAB3791 |
| CD40L | R&D Systems | Human CD40 Ligand/TNFSF5 DuoSet | DY617 |
| CD41 | Abcam | Mouse Anti-Human Integrin alpha 2b/beta 3 Monoclonal Antibody, Unconjugated, Clone CRC64 | ab38431 |
| CD41 | Abcam | Mouse Anti-Integrin alpha 2 beta, Integrin beta 3 Monoclonal Antibody, Unconjugated, Clone 237 | ab662 |
| CD41 | Abcam | Mouse Anti-Integrin alpha 2b/beta 3 Monoclonal Antibody, Unconjugated, Clone F11 | ab19775 |
| CD43 | R&D Systems | Human CD43 MAb (Clone 290111) | MAB2038 |
| CD43 | Abcam | Mouse Anti-CD43 Monoclonal Antibody, Unconjugated, Clone MEM-59 | ab9088 |
| CD44H | R&D Systems | Human CD44H MAb (Clone 2C5) | BBA10 |
| CD44H | Abcam | Mouse Anti-CD44 Monoclonal Antibody, Unconjugated, Clone A3D8 | ab6337 |
| CD44H | Abcam | Mouse Anti-CD44 Monoclonal Antibody, Unconjugated, Clone J-173 | ab19657 |
| CD45 | R&D Systems | Human CD45 MAb (Clone 2D1) | MAB1430 |
| CD45 | Abcam | Mouse Anti-Human CD45 Azide free Monoclonal Antibody, Unconjugated, Clone B-A11 | ab34316 |
| CD46 | R&D Systems | Human CD46 MAb (Clone 344519) | MAB2005 |
| CD46 | Abcam | Mouse Anti-CD46 Monoclonal Antibody, Unconjugated, Clone J4.48 | ab19739 |
| CD49d | R&D Systems | Human Integrin alpha 4/CD49d MAb (Clone 7.2R) | MAB1354 |
| CD49d | R&D Systems | Human Integrin alpha 4/VLA-4/CD49d MAb (Clone 2B4) | BBA37 |
| CD55 | R&D Systems | Human CD55/DAF MAb (Clone 278803) | MAB2009 |
| CD55 | R&D Systems | Human CD55/DAF MAb (Clone 278810) | MAB20091 |
| CD56 | R&D Systems | Human NCAM-1/CD56 MAb (Clone 301040) | MAB2408 |

TABLE 47-continued

Capture Antibodies

| CD Marker ID | Vendor | Full Identity | Catalogue # |
| --- | --- | --- | --- |
| CD56 | R&D Systems | Human NCAM-1/CD56 MAb (Clone 301021) | MAB24081 |
| CD62P | R&D Systems | Human P-Selectin/CD62P DuoSet | DY137 |
| CD64 | R&D Systems | Human Fc gamma RI/CD64 MAb (Clone 10.1) | MAB1257 |
| CD64 | R&D Systems | Human Fc gamma RI/CD64 MAb (Clone 276426) | MAB12571 |
| CD66a | R&D Systems | Human CEACAM-1 MAb (Clone 283340) | MAB2244 |
| CD66a | R&D Systems | Human CEACAM-1 MAb (Clone 283324) | MAB22441 |
| CD7 | Abcam | Mouse Anti-CD7 Monoclonal Antibody, Unconjugated, Clone MEM-186 | ab8236 |
| CD7 | BD | Mouse Anti-CD7 Monoclonal Antibody, Unconjugated, Clone M-T701 | 555359 |
| CD71 | R&D Systems | Human TfR MAb (Clone 29806) | MAB2474 |
| CD71 | Abcam | Chicken Anti-Human Transferrin Receptor Polyclonal Antibody, Unconjugated | ab37632 |
| CD71 | Abcam | Mouse Anti-Human Transferrin Receptor Azide free Monoclonal Antibody, Unconjugated, Clone B-G24 | ab47094 |
| CD8 (alpha) | R&D Systems | Human CD8 alpha MAb (Clone 37006) | MAB1509 |
| CD8 (alpha) | Abcam | Mouse Anti-CD8 Monoclonal Antibody, Unconjugated, Clone 14 | ab20133 |
| CD83 | R&D Systems | Human CD83 MAb (Clone HB15e) | MAB1774 |
| CD83 | BD | Mouse Anti-CD83 Monoclonal Antibody, Unconjugated, Clone HB15e | 556854 |
| CD85d | R&D Systems | Human ILT4/CD85d MAb (Clone 287219) | MAB2078 |
| CD85d | R&D Systems | Human ILT4/CD85d Affinity Purified Polyclonal Ab | AF2078 |
| CD85j | R&D Systems | Human ILT2/CD85j MAb (Clone 292303) | MAB2017 |
| CD85j | R&D Systems | Human ILT2/CD85j MAb (Clone 292305) | MAB20171 |
| CD9 | R&D Systems | Human CD9 MAb (Clone 209306) | MAB1880 |
| CD9 | BioLegend | Mouse Anti-Human CD9 Monoclonal Antibody, Unconjugated, Clone HI9a | 312102 |
| CD9 | BD | Mouse Anti-CD9 Monoclonal Antibody, Unconjugated, Clone M-L13 | 555370 |
| CD90 | R&D Systems | Human CD90/Thy1 MAb (Clone Thy-1A1) | MAB2067 |
| CD90 | Abcam | Mouse Anti-CD90/Thy1 Monoclonal Antibody, Unconjugated, Clone AF-9 | ab23894 |
| CD90 | Abcam | Mouse Anti-CD90/Thy1 Monoclonal Antibody, Unconjugated, Clone aTHy-1A1 | ab20147 |
| CD97 | R&D Systems | Human CD97 MAb (Clone 380903) | AF2529 |
| CD97 | BD | Mouse Anti-CD97 Monoclonal Antibody, Unconjugated, Clone VIM3b | 555772 |
| CDw217 | R&D Systems | Human IL-17 R DuoSet | DY177 |
| CD138 | Abcam | Mouse Anti-Human Syndecan Monoclonal Antibody, Unconjugated, Clone B-A38 | ab34164 |
| CD138 | BD | Mouse Anti-CD138 Monoclonal Antibody, Unconjugated, Clone DL-101 | 550804 |
| CD138 | R&D Systems | Human Syndecan-1 MAb (Clone 359103) | MAB2780 |
| CD141 | Abcam | Mouse Anti-Human Thrombomodulin Monoclonal Antibody, Unconjugated, Clone B-A35 | ab27393 |
| CD141 | BD | Mouse Anti-CD141 Monoclonal Antibody, Unconjugated, Clone 1A4 | 559780 |
| CD50 | R&D Systems (Matched Set) | Human ICAM-3/CD50 MAb (Clone ICAM-3.3) | BBA15 |
| CD52 | Abcam | Mouse Anti-CD52 Monoclonal Antibody, Unconjugated, Clone HI186 | ab2576 |
| CD52 | BD | Mouse Anti-CD52 Monoclonal Antibody, Unconjugated, Clone H24-930 | 558211 |
| CD70 | BD | Mouse Anti-CD70 Monoclonal Antibody, Unconjugated, Clone Ki-24 | 555833 |
| CD70 | R&D Systems | Human CD27 Ligand/TNFSF7 MAb (Clone 301731) | MAB2738 |
| CD10 | R&D Systems | Duoset | 842131 |
| CD116 | R&D Systems | Human GM-CSF R alpha Biotinylated Affinity Purified PAb | BAF706 |
| CD11b | R&D Systems | Human Integrin alpha M/CD11b Biotinylated MAb (Clone ICRF44) | BAM1699 |
| CD11c | Biolegend | Mouse Anti-Human CD11c Monoclonal Antibody, Biotin Conjugated, Clone 3.9 | 301612 |
| CD123 | R&D Systems | Human IL-3 R alpha Biotinylated Affinity Purified PAb | BAF841 |
| CD129 | Biolegend | Biotin anti-human IL-9 Receptor | 310409 |
| CD13 | Abcam | Mouse Anti-CD13 Monoclonal Antibody, Biotin Conjugated, Clone 22A5 | ab25723 |
| CD137 | R&D Systems | Duoset | 840975 |
| CD143 | R&D Systems | Duoset | 841366 |
| CD147 | R&D Systems | Human EMMPRIN Biotinylated Affinity Purified PAb | BAF972 |

TABLE 47-continued

Capture Antibodies

| CD Marker ID | Vendor | Full Identity | Catalogue # |
|---|---|---|---|
| CD15 | Abcam | Mouse Anti-CD15 Monoclonal Antibody, Biotin Conjugated, Clone TG1 | ab25725 |
| CD152 | BD | CD152/Biotin | 555852 |
| CD156b | R&D Systems | Duoset | 847976 |
| CD16 | Abcam | Mouse Anti-Human CD16 Monoclonal Antibody, Biotin Conjugated, Clone MEM-154 | ab28091 |
| CD16 | Abcam | Mouse Anti-CD16 Monoclonal Antibody, Biotin Conjugated, Clone LNK16 | ab6998 |
| CD19 | Abcam | Mouse Anti-CD19 Monoclonal Antibody, Biotin Conjugated, Clone SJ25- | ab19665 |
| CD19 | Abcam | Rat Anti-CD19 Monoclonal Antibody, Biotin Conjugated, Clone 6D5 | ab22477 |
| CD1a | Biolegend | Biotin anti-human CD1a | 300112 |
| CD20 | Abcam | Mouse Anti-CD20 Monoclonal Antibody, Biotin Conjugated, Clone 2H7 | ab27729 |
| CD200 | R&D Systems | Human CD200 Biotinylated Affinity Purified Pab | BAF627 |
| CD202b | R&D Systems | Human/Mouse Tie-2 Biotinylated Affinity Purified Pab | BAF313 |
| CD202b | Abcam | Mouse Anti-TIE2 Monoclonal Antibody, Biotin Conjugated, Clone 16 | ab27852 |
| CD212b1 | R&D Systems | Human IL-12 R beta1 Biotinylated Affinity Purified Pab | BAF839 |
| CD212b2 | R&D Systems | Human IL-12 R beta1 Biotinylated Affinity Purified Pab | BAF1959 |
| CD217 | R&D Systems | Duoset | 840714 |
| CD217B | R&D Systems | Mouse Anti-Human IL-17B Monoclonal Antibodies, Biotin Conjugated, 174106 | BAM12481 |
| CD217B | R&D Systems | Goat Anti-Human IL-17B Polyclonal Antibody, Biotin Conjugated | BAF1248 |
| CD217B R | R&D Systems | Duoset | 842060 |
| CD217C | R&D Systems | Human IL-17C Biotinylated Affinity Purified Pab | BAF1234 |
| CD217D | R&D Systems | Human IL-17D Biotinylated Affinity Purified Pab | BAF1504 |
| CD217E | R&D Systems | Human IL-17E Biotinylated Affinity Purified PAb | BAF1258 |
| CD217F | R&D Systems | Human IL-17F Biotinylated Affinity Purified PAb | BAF1335 |
| CD217R | R&D Systems | Duoset | 842045 |
| CD217R | R&D Systems | Duoset | 842045 |
| CD217rD | R&D Systems | Human IL-17 RD/SEF Biotinylated Affinity Purified Pab | BAF2275 |
| CD220 | R&D Systems | Duoset | 841873 |
| CD222 | R&D Systems | Human IGE-II R Biotinylated Affinity Purified Pab | BAF2447 |
| CD226 | R&D Systems | Human DNAM-1 Biotinylated Affinity Purified Pab | BAF666 |
| CD235a | R&D Systems | Human Glycophorin A Biotinylated MAb (Clone R10) | BAM12281 |
| CD244 | R&D Systems | Human 2B4/CD244/SLAMF4 Biotinylated Affinity Purified Pab | BAF1039 |
| CD264 | R&D Systems | Duoset | 840944 |
| CD29 | R&D Systems | Human Integrin beta 1/CD29 Biotin Affinity Purified Pab | BAF1778 |
| CD31 | Abcam | Mouse Anti-CD31 Monoclonal Antibody, Biotin Conjugated, Clone WM59 | ab7385 |
| CD33 | Abcam | Mouse Anti-Human CD33 Monoclonal Antibody, Biotin Conjugated, Clone WM53 Company Abcam | ab30373 |
| CD33 | Abcam | Mouse Anti-CD33 Monoclonal Antibody, Biotin Conjugated, Clone HIM3-4 | ab21892 |
| CD34 | Abcam | Mouse Anti-CD34 Monoclonal Antibody, Biotin Conjugated, Clone 4H11[APG] | ab21893 |
| CD35 | Exalpha | Anti-CR1/Biotin | 353 |
| CD36 | R&D Systems | Human CD36/SR-B3 Affinity Purified Polyclonal Ab | AF1955 |
| CD36 | Abcam | Rabbit Anti-Human CD36 Polyclonal Antibody, Biotin Conjugated | ab36978 |
| CD38 | Abcam | Mouse Anti-Human CD38 Monoclonal Antibody, Biotin Conjugated, Clone AT13/5 | ab30418 |
| CD4 | R&D Systems | Human CD4 Biotinylated Affinity Purified Pab | BAF379 |
| CD4 | Abcam | Mouse Anti-CD41/Integrin alpha 2b Monoclonal Antibody, Biotin Conjugated, Clone PM6/248 | ab30434 |
| CD40L | R&D Systems | Duoset | 841131 |
| CD41 | Abcam | Mouse Anti-CD41/Integrin alpha 2b Monoclonal Antibody, Biotin Conjugated, Clone M148 | ab19699 |
| CD43 | R&D Systems | Human CD43 Biotinylated Affinity Purified Pab | BAF2038 |
| CD44H | Abcam | Mouse Anti-CD44 Monoclonal Antibody, Biotin Conjugated, Clone F10-44-2 | ab30404 |
| CD44H | Abcam | Mouse Anti-Human CD44 Monoclonal Antibody, Biotin Conjugated, Clone MEM-85 | ab28105 |

TABLE 47-continued

Capture Antibodies

| CD Marker ID | Vendor | Full Identity | Catalogue # |
|---|---|---|---|
| CD45 | Abcam | Mouse Anti-Human CD45 Monoclonal Antibody, Biotin Conjugated, Clone F10-89-4 | ab30468 |
| CD46 | R&D Systems | Human CD46 Biotinylated Affinity Purified PAb | BAF2005 |
| CD49d | R&D Systems | Human Integrin alpha 4/CD49d Biotinylated MAb (Clone 7.2R) | BAM1354 |
| CD55 | R&D Systems | Human CD55/DAF Biotinylated Affinity Purified Pab | BAF2009 |
| CD56 | R&D Systems | Human NCAM-1/CD56 Biotinylated Affinity Purified Pab | BAF2408 |
| CD6 | Abcam | CD6/Biotin | |
| CD62P | R&D Systems | Duoset | 841155 |
| CD64 | R&D Systems | Human Fc gamma RI/CD64 Biotinylated Affinity Purified PAb | BAF1257 |
| CD66a | R&D Systems | Human CEACAM-1 Biotinylated Affinity Purified Pab | BAF2244 |
| CD7 | Abcam | Mouse Anti-Human CD7 Monoclonal Antibody, Biotin Conjugated, Clone LT7 | ab34293 |
| CD71 | R&D Systems | Human TfR Biotinylated Affinity Purified Pab | BAF2474 |
| CD71 | Abcam | Mouse Anti-Human Transferrin Receptor Monoclonal Antibody, Biotin Conjugated, Clone MEM-75 | ab28116 |
| CD8 (alpha) | Abcam | Mouse Anti-Human CD8 Monoclonal Antibody, Biotin Conjugated, Clone MEM-31 | ab28090 |
| CD8 (alpha) | Abcam | Mouse Anti-CD8 Monoclonal Antibody, Biotin Conjugated, Clone LT8 | ab34282 |
| CD83 | R&D Systems | Human CD83 Biotinylated Affinity Purified Pab | BAF2044 |
| CD85d | R&D Systems | Human ILT4/CD85d Biotinylated Affinity Purified Pab | BAF2078 |
| CD85j | R&D Systems | Human ILT2/CD85j Biotinylated Affinity Purified Pab | BAF2017 |
| CD9 | Abcam | Mouse Anti-Human CD9 Monoclonal Antibody, Biotin Conjugated, Clone MEM-61 | ab28094 |
| CD90 | BD | Mouse Anti-CD90 Monoclonal Antibody, Biotin Conjugated, Clone 5E10 | 555594 |
| CD90 | Abcam | Mouse Anti-CD90/Thy 1 Monoclonal Antibody, Biotin Conjugated, Clone F15-42-1 | ab11154 |
| CD97 | R&D Systems | Human CD97 Biotinylated Affinity Purified PAb | BAF2529 |
| CD138 | R&D Systems | Human Syndecan-1 Biotinylated Affinity Purified PAb | BAF2780 |
| CD141 | R&D Systems | Anti-Mouse Thrombomodulin/CD141 Affinity Purified Polyclonal Antibody, Unconjugated | AF3894 |
| CD50 | R&D Systems (Matched Set) | Human ICAM-3/CD50 Biotinylated Affinity Purified PAb | BAF813 |
| CD52 | Santa Cruz | Rabbit Anti-Human CD52 (FL-61) Polyclonal Antibody, Unconjugated | sc-25838 |
| CD70 | Genetex | Goat Anti-CD27 Polyclonal Antibody, Unconjugated | GTX10952 |
| HLA A | Abcam | Mouse Anti-HLA ABC Monoclonal Antibody, Biotin Conjugated, Clone W6/32 | ab21148 |
| CD10 | R&D Systems | Human Neprilysin Ectodomain MAb (Clone 212504) | MAB1182 |
| CD102 | R&D Systems | Human ICAM-2/CD102 MAb (Clone 86911) | MAB244 |
| CD105 | R&D Systems | Human Endoglin/CD105 MAb (Clone 166713) | MAB10972 |
| CD106 | R&D Systems | Human VCAM-1/CD106 MAb (Clone HAE-2Z) | MAB809 |
| CD110 | R&D Systems | Human Thrombopoietin R MAb (Clone 167639) | MAB1016 |
| CD110 | R&D Systems | Human Thrombopoietin R MAb (Clone 167620) | MAB10161 |
| CD114 | R&D Systems | Human G-CSF R/CD114 MAb (Clone 38660) | MAB381 |
| CD115 | R&D Systems | Human M-CSF R MAb (Clone 61715) | MAB3292 |
| CD117 | R&D Systems | Human SCF R/c-kit MAb (Clone 47233) | MAB332 |
| CD120a | R&D Systems | Human TNF RI/TNRSF1A MAb (Clone 16805) | MAB625 |
| CD120b | R&D Systems | Human TNF RII/TNFRSF1B MAb (Clone 22210) | MAB726 |
| CD121a | R&D Systems | Human IL-1 RI MAb (Clone 35730) | MAB269 |
| CD121b | R&D Systems | Human IL-1 RII MAb (Clone 34141) | MAB663 |
| CD124 | R&D Systems | Human IL-4 R MAb (Clone 25463) | MAB230 |
| CD125 | R&D Systems | Human IL-5 R alpha MAb (Clone 26815) | MAB253 |
| CD126 | R&D Systems | Human IL-6 R MAb (Clone 17506) | MAB227 |
| CD127 | R&D Systems | Human IL-7 R alpha MAb (Clone 40131) | MAB306 |
| CD129 | R&D Systems | Human IL-9 R MAb (Clone 33423) | MAB290 |
| CD129 | R&D Systems | Human IL-9 R MAb (Clone 33401) | MAB2902 |
| CD129 | R&D Systems | Human IL-9 R MAb (Clone 33449) | MAB2901 |
| CD130 | R&D Systems | Human gp130 MAb (Clone 28105) | MAB628 |
| CD132 | R&D Systems | Human Common gamma Chain MAb (Clone 31134) | MAB2841 |

TABLE 47-continued

Capture Antibodies

| CD Marker ID | Vendor | Full Identity | Catalogue # |
|---|---|---|---|
| CD132 | R&D Systems | Human Common gamma Chain MAb (Clone 38024) | MAB284 |
| CD137 | R&D Systems | Human 4-1BB/ TNFRSF9 Affinity Purified Polyclonal Ab | AF838 |
| CD14 | R&D Systems | Human CD14 MAb (Clone 50040) | MAB3833 |
| CD143 | R&D Systems | Human ACE MAb (Clone 171417) | MAB929 |
| CD143 | R&D Systems | Huan ACE Mab (Clone 171409) | MAB9291 |
| CD148 | R&D Systems | Human DEP-1/ CD148 MAb (Clone 143-41) | MAB1934 |
| CD148 | R&D Systems | Human DEP-1/ CD148 MAb (Clone 261922) | MAB19341 |
| CD152 | R&D Systems | Human CTLA-4 MAb (Clone 48815) | MAB325 |
| CD156b | R&D Systems | Human TACE/ADAM17 Cytosolic MAb (Clone 136133) | MAB21291 |
| CD156b | R&D Systems | Human TACE/ADAM17 Ectodomain MAb (Clone 111623) | MAB9302 |
| CD156b | R&D Systems | Human TACE/ADAM17 Cytosolic MAb (Clone 136121) | MAB2129 |
| CD156b | R&D Systems | Human TACE/ADAM17 Ectodomain MAb (Clone 111633) | MAB9301 |
| CD156b | R&D Systems | Human TACE/ADAM17 Ectodomain MAb (Clone 111636) | MAB930 |
| CD166 | R&D Systems | Human ALCAM MAb (Clone 105902) | MAB6561 |
| CD170 | R&D Systems | Human Siglec-5 MAb (Clone 194128) | MAB10721 |
| CD171 | R&D Systems | Human NCAM-L1 MAb (Clone 84321) | MAB777 |
| CD178 | R&D Systems | Human Fas Ligand/ TNFSF6 MAb (Clone 100419) | MAB126 |
| CD195 | R&D Systems | Human CCR5 MAb (Clone 45502) | MAB180 |
| CD195 | R&D Systems | Human CCR5 MAb (Clone CTC8) | MAB1801 |
| CD195 | R&D Systems | Human CCR5 MAb (Clone 45549) | MAB183 |
| CD195 | R&D Systems | Human CCR5 MAb (Clone 45529) | MAB184 |
| CD195 | R&D Systems | Human CCR5 MAb (Clone 45523) | MAB181 |
| CD195 | R&D Systems | Human CCR5 MAb (Clone 45531) | MAB182 |
| CD195 | R&D Systems | Human CCR5 MAb (Clone CTC5) | MAB1802 |
| CD1d | BD Bio | Mouse Anti-CD1d Monoclonal Antibody, Unconjugated, Clone CD1d42 | 550254 |
| CD2 | R&D Systems | Mouse Anti-Human CD2 Monoclonal Antibody, Unconjugated, Clone 299813 | MAB1856 |
| CD2 | R&D Systems | Human CD2 MAb (Clone 299813) | MAB18561 |
| CD213a1 | R&D Systems | Human IL-13 R alpha 1 MAb (Clone 116730) | MAB146 |
| CD213a2 | R&D Systems | Human IL-13 R alpha 2 MAb (Clone 83807) | MAB6141 |
| CD220 | R&D Systems | Human Insulin R/CD220 MAb (Clone 243524) | MAB1544 |
| CD220 | R&D Systems | Human Insulin R/CD220 MAb (Clone 243523) | MAB15441 |
| CD221 | R&D Systems | Human IGF-I R MAb (Clone 33255) | MAB391 |
| CD23 | R&D Systems | Human Fc epsilon RII/ CD23 MAb (Clone 138628) | MAB123 |
| CD239 | R&D Systems | Human BCAM MAb (Clone 87207) | MAB1481 |
| CD25 | R&D Systems | Human IL-2 R alpha MAb (Clone 22722) | MAB223 |
| CD25 | R&D Systems | Human IL-2 R alpha MAb (Clone 24204) | MAB623 |
| CD258 | R&D Systems | Human LIGHT/ TNFSF14 MAb (Clone 115520) | MAB664 |
| CD26 | R&D Systems | Human DPPIV/CD26 MAb (Clone 222113) | MAB1180 |
| CD263 | R&D Systems | Human TRAIL R3/ TNFRSF10C MAb (Clone 90905) | MAB6301 |
| CD264 | R&D Systems | Human TRAIL R4/ TNFRSF10D MAb (Clone 104918) | MAB633 |
| CD27 | R&D Systems | Human CD27/ TNFRSF7 MAb (Clone 57703) | MAB382 |
| CD28 | R&D Systems | Human CD28 MAb (Clone 37407) | MAB342 |
| CD295 | R&D Systems | Human Leptin R MAb (Clone 52208) | MAB389 |
| CD295 | R&D Systems | Human Leptin R MAb (Clone 52263) | MAB867 |
| CD30 | R&D Systems | Human CD30/TNFRSF8 MAb (Clone 81337) | MAB229 |
| CD30 | R&D Systems | Mouse Anti-Human CD30/TNFRSF8 Monoclonal Antibody, Unconjugated, Clone 81316 | MAB2291 |
| CD309 | R&D Systems | Human VEGF R/ KDR2 MAb (Clone 89109) | MAB3573 |
| CD324 | R&D Systems | Human E-Cadherin MAb (Clone 77308) | MAB18382 |
| CD32b/c | R&D Systems | Human Fc gamma RIIB/C MAb (Clone 190710) | MAB18751 |
| CD33L2 | R&D Systems | Human Siglec-5 MAb (Clone 194117) | MAB1072 |
| CD40 | R&D Systems | Human CD40/TNFRSF5 MAb (Clone 82102) | MAB6322 |
| CD40 | R&D Systems | Human CD40/TNFRSF5 MAb (Clone 82105) | MAB632 |
| CD40 | R&D Systems | Human CD40/TNFRSF5 MAb (Clone 82111) | MAB6321 |
| CD40L | R&D Systems | Human CD40 Ligand/ TNFSF5 MAb (Clone 40804) | MAB617 |
| CD50 | R&D Systems | Human ICAM-3/CD50 MAb (Clone Cal 3.10) | BBA29 |
| CD50 | R&D Systems | Human ICAM-3/CD50 MAb (Clone Cal 3.34) | BBA28 |
| CD50 | R&D Systems | Human ICAM-3/CD50 MAb (Clone ICAM-3.3) | BBA15 |
| CD54 | R&D Systems | Human ICAM-1/CD54 MAb (Clone BBIG-I1) | BBA3 |
| CD54 | R&D Systems | Human ICAM-1/CD54 MAb (Clone 14C11) | MAB720 |
| CD58 | R&D Systems | Human CD58/LFA-3 MAb (Clone 248310) | MAB1689 |

TABLE 47-continued

Capture Antibodies

| CD Marker ID | Vendor | Full Identity | Catalogue # |
|---|---|---|---|
| CD6 | R&D Systems | Human CD6 MAb (Clone 123119) | MAB627 |
| CD62E | R&D Systems | Human E-Selectin/CD62E MAb (Clone BBIG-E4) | BBA16 |
| CD62L | R&D Systems | Human L-Selectin/CD62L MAb (CL 4G8) | BBA24 |
| CD62P | R&D Systems | Human P-Selectin/CD62P MAb (CI 9E1) | BBA30 |
| CD80 | R&D Systems | Human B7-1/CD80 MAb (Clone 37711) | MAB140 |
| CD84 | R&D Systems | Human CD84/SLAMF5 MAb (Clone 273508) | MAB1855 |
| CD86 | R&D Systems | Human B7-2/CD86 MAb (Clone 37301) | MAB141 |
| CD87 | R&D Systems | Human uPAR MAb (Clone 62022) | MAB807 |
| CD95 | R&D Systems | Human Fas/TNFRSF6 MAb (Clone 50830) | MAB144 |
| CDw329 | R&D Systems | Human Siglec-9 MAb (Clone 191240) | MAB1139 |
| CD10 | R&D Systems | Human Neprilysin Biotinylated Affinity Purified PAb | BAF1182 |
| CD102 | R&D Systems | Human ICAM-2/CD102 Biotinylated Affinity Purified PAb | BAF244 |
| CD105 | R&D Systems | Human Endoglin/CD105 Biotinylated Affinity Purified PAb | BAF1097 |
| CD106 | R&D Systems | Human VCAM-1/CD106 Biotinylated Affinity Purified PAb | BAF809 |
| CD110 | R&D Systems | Human Thrombopoietin R Biotinylated Affinity Purified PAb | BAF1016 |
| CD114 | R&D Systems | Human G-CSF R/CD114 Affinity Purified Polyclonal Ab | AF-381-PB |
| CD115 | R&D Systems | Human M-CSF R Biotinylated Affinity Purified PAb | BAF329 |
| CD117 | R&D Systems | Human SCF R/c-kit Biotinylated Affinity Purified PAb | BAF332 |
| CD120a | R&D Systems | Human TNF RI/TNFRSF1A Biotinylated Affinity Purified PAb | BAF225 |
| CD120b | R&D Systems | Human TNF RII/TNFRSF1B Biotinylated Affinity Purified PAb | BAF726 |
| CD121a | R&D Systems | Human IL-1 RI Biotinylated Affinity Purified PAb | BAF269 |
| CD121b | R&D Systems | Human IL-1 RII Biotinylated Affinity Purified PAb | BAF263 |
| CD124 | R&D Systems | Human IL-4 R Biotinylated Affinity Purified PAb | BAF230 |
| CD125 | R&D Systems | Human IL-5 R alpha Biotinylated Affinity Purified PAb | BAF253 |
| CD126 | R&D Systems | Human IL-6 R Biotinylated Affinity Purified PAb | BAF227 |
| CD127 | R&D Systems | Human IL-7 R alpha Biotinylated Affinity Purified PAb | BAF306 |
| CD129 | R&D Systems | Human IL-9 R Biotinylated Affinity Purified Ab | BAF290 |
| CD130 | R&D Systems | Human gp130 Biotinylated Affinity Purified PAb | BAF228 |
| CD132 | R&D Systems | Human Common gamma Chain Biotinylated Affinity Purified PAb | BAF284 |
| CD137 | R&D Systems | Human 4-1BB/TNFRSF9 Biotinylated Affinity Purified PAb | BAF838 |
| CD137 | R&D Systems | Human 4-1BB/TNFRSF9 Affinity Purified Polyclonal Ab | AF838 |
| CD14 | R&D Systems | Human CD14 Biotinylated Affinity Purified PAb | BAF383 |
| CD143 | R&D Systems | Human ACE Bitotinylated Mab (171417) | BAM929 |
| CD148 | R&D Systems | Human/Mouse/Rat DEP-1/CD148 Affinity Purified Polyclonal Ab | AF1934 |
| CD152 | R&D Systems | Human CTLA-4 Biotinylated Affinity Purified PAb | BAF386 |
| CD156b | R&D Systems | Human TACE/ADAM17 Ecto Biotinylated Affinity Purified PAb | BAF930 |
| CD166 | R&D Systems | Human ALCAM Biotinylated Affinity Purified PAb | BAF656 |
| CD170 | R&D Systems | Human Siglec-5 Biotinylated MAb (Clone 194111) | BAM10722 |
| CD171 | R&D Systems | Human NCAM-L1 Biotinylated Affinity Purified PAb | BAF277 |
| CD178 | R&D Systems | Human Fas Ligand/TNFSF6 Biotinylated Affinity Purified PAb | BAF126 |
| CD195 | R&D Systems | Human CCR5 Biotinylated MAb (Clone 45531) | FAB182B |
| CD195 | R&D Systems | Human CCR5 Biotinylated MAb (Clone 45523) | FAB181B |
| CD195 | R&D Systems | Human CCR5 Biotinylated MAb (Clone 455049) | FAB183B |
| CD195 | R&D Systems | Human CCR5 Biotinylated MAb (Clone 45502) | FAB180B |
| CD1d | BD Bio | Rat Anti-CD1d Monoclonal Antibody, Biotin Conjugated, Clone 1B1 | 553844 |
| CD2 | R&D Systems | Goat Anti-Human CD2 Polyclonal Antibody, Biotin Conjugated | BAF1856 |
| CD213a1 | R&D Systems | Human IL-13 R alpha 1 Biotinylated Affinity Purified PAb | BAF152 |
| CD213a2 | R&D Systems | Human IL-13 R alpha 2 Biotinylated Affinity Purified PAb | BAF614 |
| CD220 | R&D Systems | Human Insulin R/CD220 Biotinylated MAb (Clone 243524) | BAM1544 |
| CD221 | R&D Systems | Human IGF-I R Biotinylated Affinity Purified PAb | BAF391 |
| CD23 | R&D Systems | Human Fc epsilon RII/CD23 Biotinylated Affinity Purified PAb | BAF123 |

TABLE 47-continued

Capture Antibodies

| CD Marker ID | Vendor | Full Identity | Catalogue # |
|---|---|---|---|
| CD239 | R&D Systems | Human BCAM Biotinylated Affinity Purified PAb | BAF148 |
| CD25 | R&D Systems | Human IL-2 R alpha Biotinylated Affinity Purified PAb | BAF223 |
| CD258 | R&D Systems | Human LIGHT/TNFSF14 Biotinylated Affinity Purified PAb | BAF664 |
| CD26 | R&D Systems | Human DPPIV/CD26 Biotinylated Affinity Purified PAb | BAF1180 |
| CD263 | R&D Systems | Human TRAIL R3/TNFRSF10C Biotinylated Affinity Purified PAb | BAF630 |
| CD264 | R&D Systems | Human TRAIL R4/TNFRSF10D Biotinylated Affinity Purified PAb | BAF633 |
| CD27 | R&D Systems | Human CD27/TNFRSF7 Biotinylated Affinity Purified PAb | BAF382 |
| CD28 | R&D Systems | Human CD28 Biotinylated Affinity Purified PAb | BAF342 |
| CD295 | R&D Systems | Human Leptin R Biotinylated Affinity Purified PAb | BAF389 |
| CD30 | R&D Systems | Goat Anti-Human CD30/TNFRSF8 Polyclonal Antibody, Biotin Conjugated | BAF229 |
| CD309 | R&D Systems | Human VEGF R2/KDR Biotinylated Affinity Purified PAb | BAF357 |
| CD324 | R&D Systems | Human E-Cadherin Biotinylated Affinity Purified PAb | BAF648 |
| CD32b/c | R&D Systems | Human Fc gamma RIIB/CD32b Biotinylated Affinity Purified Pab | BAF1330 |
| CD32b/c | R&D Systems | Human Fc gamma RIIB/C Biotinylated MAb (Clone 190703) | BAM1875 |
| CD40 | R&D Systems | Human CD40/TNFRSF5 Biotinylated Affinity Purified PAb | BAF632 |
| CD40L | R&D Systems | Human CD40 Ligand/TNFSF5 Biotinylated Affinity Purified PAb | BAF617 |
| CD50 | R&D Systems | Human ICAM-3/CD50 Biotinylated Affinity Purified PAb | BAF813 |
| CD50 | R&D Systems | Human ICAM-3/CD50 Biotinylated Affinity Purified PAb | BAF715 |
| CD54 | R&D Systems | Human ICAM-1/CD54 Biotinylated Affinity Purified PAb | BAF720 |
| CD58 | R&D Systems | Human CD58/LFA-3 Biotinylated Affinity Purified PAb | BAF1689 |
| CD6 | R&D Systems | Human CD6 Biotinylated Affinity Purified PAb | BAF627 |
| CD62E | R&D Systems | Human E-Selectin/CD62E Biotinylated MAb (Clone BBIG-E5) | BBA8 |
| CD62L | R&D Systems | Human L-Selectin/CD62L Biotinylated Affinity Purified PAb | BAF728 |
| CD62P | R&D Systems | Human P-Selectin/CD62P Biotinylated Affinity Purified PAb | BAF137 |
| CD80 | R&D Systems | Human B7-1/CD80 Biotinylated MAb (Clone 37721) | BAM1402 |
| CD84 | R&D Systems | Human CD84/SLAMF5 Biotinylated Affinity Purified PAb | BAF1855 |
| CD86 | R&D Systems | Human B7-2/CD86 Biotinylated Affinity Purified PAb | BAF141 |
| CD87 | R&D Systems | Human uPAR Biotinylated Affinity Purified PAb | BAF607 |
| CD95 | R&D Systems | Human Fas/TNFRSF6 Biotinylated Affinity Purified PAb | BAF326 |
| CDw329 | R&D Systems | Human Siglec-9 Biotinylated Affinity Purified Pab | BAF1139 |

The invention claimed is:

1. A method of detecting or prognosing acute myeloid leukemia (AML) in a test individual, said method comprising, for each of a plurality of sCD antigens, wherein at least one sCD antigen is selected from the group consisting of: sCD14, sCD30, sCD54, sCD117 and sCD130,
   (a) quantifying a level of expression of said sCD antigen in a serum, plasma or other body fluid sample of said test individual, and
   (b) comparing said level of sCD antigen quantified in step (a) to a quantified level of control sCD antigen in serum, plasma or other body fluid samples of control subjects classified as healthy (normal) subjects; and/or
   (c) comparing said level of sCD antigen quantified in step (a) to a quantified level of control sCD antigen in serum, plasma or other body fluid samples of control subjects classified as having AML;

wherein a determination from step (b) that said level of step (a) is statistically different from said level in step (b) in said serum, plasma or other body fluid samples of control subjects classified as healthy (normal) samples of said subjects classified as healthy subjects, results in a classification of said sCD antigen expression in said test individual with that of said subjects classified as having AML;

wherein a determination from steps (b) and (c) that said level of step (a) is statistically different from said level in step (c) in said serum, plasma or other body fluid samples of said subjects classified as having AML and is statistically similar to said level in step (b) in said serum, plasma or other body fluid samples of said subjects classified as healthy subjects, results in a classification of said sCD antigen expression in said test individual with that of said subjects who classified as healthy subjects, and
   wherein a determination from steps (b) and (c) that said level of step (a) is statistically similar to said level in step (c) in said serum, plasma or other body fluid samples of said subjects classified as having AML, and is statistically different from said level in step (b) in said serum, plasma or other body fluid samples of said subjects classified as healthy subjects, results in a classification of said sCD antigen expression in said test individual with that of said subjects classified as having AML.

2. The method of claim 1, wherein said plurality of sCD antigens comprises one or more sCD antigens selected from the group consisting of: sCD14, sCD30, sCD54, sCD117 and sCD130, and wherein said plurality of sCD antigens comprises one or more sCD antigens selected from the group of soluble (secreted or shed) isoforms of the CD antigens listed in Table 43.

3. The method of claim 1, wherein said plurality of sCD antigens comprises sCD antigens and MHC Class I antigens, wherein said sCD antigens comprises one or more sCD antigens selected from the group consisting of: sCD14, sCD30, sCD54, sCD117 and sCD130.

4. The method of claim 3, wherein said sCD antigens comprises one or more sCD antigens selected from the group consisting of: sCD14, sCD30, sCD54, sCD117 and sCD130, and one or more sCD antigens selected from the group of soluble isoforms of the CD antigens listed in Table 43.

5. The method of claim 1, wherein said method detects remission of acute myeloid leukemia (AML) in a test individual suspected of being in remission of acute leukemia
wherein a determination from steps (b) and (c) that said level of step (a) is statistically different from said level in step (c) in said serum samples of said subjects classified as having AML and is statistically similar to said level in step (b) in said serum samples of said subjects classified as healthy subjects, is indicative of said test individual's being in full remission,
and
wherein a determination from steps (b) and (c) that said level of step (a) is statistically similar to said level in step (c) in said serum samples of said subjects classified as having AML, and is statistically different from said level in step (b) in said serum samples of said subjects classified as healthy subjects, results in a classification of said sCD antigen expression in said test individual with that of said subjects classified as having AML.

6. The method of claim 1, wherein said method detects relapse of acute myeloid leukemia (AML)
wherein a determination from steps (b) and (c) that said level of step (a) is statistically different from said level in step (c) in said serum samples of said subjects classified as having AML and is statistically similar to said level in step (b) in said serum samples of said subjects classified as healthy subjects, results in a classification of said sCD antigen expression in said test individual with that of said subjects classified as not having AML, and
wherein a determination from steps (b) and (c) that said level of step (a) is statistically similar to said level in step (c) in said serum samples of said subjects classified as having AML, and is statistically different from said level in step (b) in said serum samples of said subjects classified as healthy subjects, is indicative of said test individual's having a relapse of AML.

7. The method of claim 1 wherein a first soluble CD (sCD) antigen is sCD117.

8. The method of claim 1 wherein a first soluble CD (sCD) antigen is sCD117 and a second soluble CD antigen is selected from the group consisting of: sCD14, sCD30, sCD54 and sCD130.

9. The method of claim 1 wherein a first soluble CD (sCD) antigen is sCD117, and a second and third soluble CD antigen is selected from the group consisting of: sCD14, sCD30, sCD54 and sCD130.

10. The method of claim 1 wherein a first soluble CD (sCD) antigen is sCD117, and a second, third and fourth soluble CD antigen is selected from the group consisting of: sCD14, sCD30, sCD54 and sCD130.

11. The method of claim 1 wherein a first soluble CD (sCD) antigen is sCD117, and a second, third, fourth and fifth soluble CD antigen is selected from the group consisting of: sCD14, sCD30, sCD54 and sCD130.

12. The method of claim 1 wherein said plurality of sCD antigens consists of sCD117, sCD14, sCD30, sCD54 and sCD130 and sCD35.

13. The method of claim 1 wherein said plurality of sCD antigens consists of sCD117, sCD14, sCD30, sCD54 and sCD130 and sCD44.

14. The method of claim 1 wherein said plurality of sCD antigens consists of two or more soluble CD (sCD) antigens selected from the group consisting of: sCD117, sCD14, sCD30, sCD54 and sCD130.

15. The method of claim 1 wherein said plurality of sCD antigens consists of three or more soluble CD (sCD) antigens selected from the group consisting of: sCD117, sCD14, sCD30, sCD54 and sCD130.

16. The method of claim 1 wherein said plurality of sCD antigens consists of four or more soluble CD (sCD) antigens selected from the group consisting of: sCD117, sCD14, sCD30, sCD54 and sCD130.

17. The method of claim 1 wherein said method of diagnosing AML has a sensitivity greater than 70% when at least one of said sCD antigens quantified in step (a) is sCD117.

18. The method of claim 1 wherein said method of diagnosing AML has a sensitivity greater than 83% when at least one of said sCD antigens quantified in step (a) is sCD117.

19. The method of claim 1 wherein said method of diagnosing AML has a specificity greater than 95% when at least one of said sCD antigens quantified in step (a) is sCD117.

20. The method of claim 1 wherein said method of diagnosing AML has a specificity of 99% when at least one of said sCD antigens quantified in step (a) is sCD117.

21. The method of claim 1 wherein determining the level of each of said sCD antigens in said sample comprises contacting said sample with one or more ligands, wherein each of said ligands is specific for one of said sCD antigens, and measuring the level of each said sCD antigen.

22. The method of claim 1 wherein one or more of said sCD antigens is detected using an antibody and said antibody is selected from the group consisting of: a polyclonal antibody, a monoclonal antibody, fv, scfv, dab, fab, and F(ab')$_2$.

23. The method of claim 1 wherein the level of each sCD antigen in said sample is quantified comprising the following steps:
 i) contacting the sample with said plurality of ligands, wherein each of said ligands specifically binds a sCD antigen in said sample,
 ii) detecting the binding of each said ligand to said sCD antigen,
 iii) quantifying the level of said sCD antigen.

24. The method of claim 23, wherein said plurality of ligands is fixed to a solid support.

25. The method of claim 24, wherein said solid support is selected from the group consisting of a plurality of beads, a chip, a glass surface, nitrocellulose, and an ELISA plate.

26. The method of claim 1, wherein said one or more sCD is detected using one or more ligand wherein each said ligand comprises the heavy and light chain antibody CDRs for an anti-sCD antibody and said CDRs are in a non-immunoglobulin scaffold.

27. The method of claim 26, wherein said non-immunoglobulin scaffold is synthetic.

28. The method of claim 26, where said scaffold is selected from the group consisting of CTLA4, fibronectin, lipocallin, Rbp, Bbp ApoD, a natural bacterial receptor, staphyloccocus A protein (SpA), GroEL, transferrin, tetranectin, human C-lectin, an AVIMER™ and an AFFIBODY™ scaffold.

29. The method claim 1 further comprising a comparison between said sample of said test subject and that of said healthy (normal) control with respect to a gene expression signature and/or a micro-RNA expression signature.

* * * * *